(12) United States Patent
Prous et al.

(10) Patent No.: US 9,980,928 B2
(45) Date of Patent: *May 29, 2018

(54) HYDROXY ALIPHATIC SUBSTITUTED PHENYL AMINOALKYL ETHER DERIVATIVES

(71) Applicant: PROUS INSTITUTE FOR BIOMEDICAL RESEARCH, S.A., Barcelona (ES)

(72) Inventors: Josep R. Prous, Barcelona (ES); Neus Serradell, Barcelona (ES); Ramon Flores, Barcelona (ES); Noemi Garcia-Delgado, Barcelona (ES); Marcel-li Carbo Banus, Barcelona (ES)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/489,186

(22) Filed: Apr. 17, 2017

(65) Prior Publication Data
US 2017/0239197 A1 Aug. 24, 2017

Related U.S. Application Data

(62) Division of application No. 14/654,661, filed as application No. PCT/EP2013/077731 on Dec. 20, 2013, now Pat. No. 9,624,158.

(30) Foreign Application Priority Data

Dec. 21, 2012 (EP) .................................. 12382527

(51) Int. Cl.
| | |
|---|---|
| *A61K 31/7028* | (2006.01) |
| *A61K 31/138* | (2006.01) |
| *A61K 31/192* | (2006.01) |
| *A61K 31/4015* | (2006.01) |
| *A61K 31/165* | (2006.01) |
| *A61K 31/381* | (2006.01) |
| *A61K 31/5375* | (2006.01) |
| *A61K 31/7034* | (2006.01) |
| *A61K 31/451* | (2006.01) |
| *A61K 31/4045* | (2006.01) |
| *A61K 31/385* | (2006.01) |

(52) U.S. Cl.
CPC .......... *A61K 31/138* (2013.01); *A61K 31/165* (2013.01); *A61K 31/381* (2013.01); *A61K 31/385* (2013.01); *A61K 31/4015* (2013.01); *A61K 31/4045* (2013.01); *A61K 31/451* (2013.01); *A61K 31/5375* (2013.01); *A61K 31/7034* (2013.01)

(58) Field of Classification Search
CPC ... C07C 217/04; C07C 59/68; C07D 207/267; C07D 307/62; C07D 339/04; C07D 265/30; A61K 31/7004; A61K 45/06; A61K 31/4015; A61K 31/138; A61K 31/375; A61K 31/192; A61K 31/385; A61K 31/5375; C07H 15/22

USPC ......................................................... 514/25
See application file for complete search history.

(56) References Cited

FOREIGN PATENT DOCUMENTS

| | | |
|---|---|---|
| CN | 101012175 A1 | 8/2007 |
| JP | 2007-535529 A | 12/2007 |
| JP | 2007-535530 A | 12/2007 |
| WO | 2005/105100 A1 | 11/2005 |
| WO | 2005/105763 A1 | 11/2005 |
| WO | 2007/085930 A1 | 8/2007 |
| WO | 2011/150347 A2 | 12/2011 |

OTHER PUBLICATIONS

Brookmeyer, et al., "Forecasting the global burden of Alzheimer's disease", Alzheimer's & Dementia 3 (2007) 186-191.
Brookmeyer, "National estimates of the prevalence of Alzheimer's disease in the United States", Alzheimers Dement. 7(1), pp. 61-73 (2011).
Brookmeyer, et al., "Projections of Alzheimer's Disease in the United States and the Public Health Impact of Delaying Disease Onset", American Journal of Public Health, vol. 88:9 (1998) pp. 1337-1342.
Bu, et al., "Neuroprotective effect of tyrosol on transient focal cerebral ischemia in rats", Neuroscience Letters 414 (2007) pp. 218-221.
Coley, et al., "Dementia Prevention: Methodological Explanations for Inconsistent Result", Epidemiol. Rev. 30: 3, pp. 34-66 (2008).
Cramer, et al., "Harnessing neuroplasticity for clinical applications", Brain 2011: 134; 1591-160.
Darbinyan, et al., "Rhodiola rosea in stress induced fatigue—A double blind cross-over study of a standarized extract SHR-5 with a repeated low-dose regimen on the mental performance of healthy physicians during night duty", Phytomedicine, vol. 7(5), pp. 365-371 (2000).
Huse, et al., "Burden of Illness in Parkinson's Disease", Movement Disorders, vol. 20, No. 11, pp. 1449-1454 (2005).

(Continued)

*Primary Examiner* — Shaojia Anna Jiang
*Assistant Examiner* — Michael C Henry
(74) *Attorney, Agent, or Firm* — Kramer Amado, P.C.

(57) ABSTRACT

Hydroxy aliphatic substituted phenyl aminoalkyl ether compounds of formula (I), and compositions thereof, are useful as a medicament in the treatment of nervous system diseases and/or the treatment of developmental, behavioral and/or mental disorders associated with cognitive deficits.

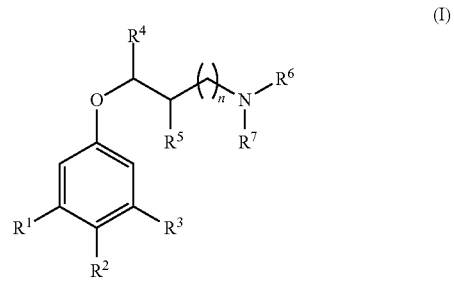

(I)

15 Claims, 4 Drawing Sheets

(56) References Cited

OTHER PUBLICATIONS

Kanupriya, et al., "Cytoprotective and antioxidant activity of Rhodiola imbricata against tert-butyl hydroperoxide induced oxidative injury in U-937 human macrophages", Molecular and Cellular Biochemistry 275, 1-6 (2005).

Li, et al., "Chemoenzymatic Route to S-Betaxolol", Synthetic Communications, 41:2468-2474 (2011).

Li, et al., "Salidroside attenuates hypoxia-induced abnormal processing of amyloid precursor protein by decreasing BACE1 expression in SH-SY5Y cells", Neuroscience Letters 481: 154-158 (2010).

Mao, et al., "Protective Role of Salidroside against Aging in a Mouse Model Induced by D-galactose", Biomedical and Environmental Sciences 23, 161-166 (2010).

Mount, et al., "Alzheimer disease: progress or profit?", Nature Medicine vol. 12, No. 7, pp. 780-784 (Jul. 2006).

Pringsheim, et al., "The Incidence and Prevalence of Huntington's Disease: A Systematic Review and Meta-analysis", Movement Disorders, vol. 27, No. 9 (2012), pp. 1083-1091.

Rao, et al., "Parkinson's Disease: Diagnosis and Treatment", American Family Physician Web site at www.aafp.org/afp 2006.

Thies, "Alzheimer's Association Report—2011 Alzheimer's disease facts and figures", Alzheimer's & Dementia 7 (2011) 208-244.

Wimo, "Alzheimer's Disease International World Alzheimer Report 2010—The Global Economic Impact of Dementia", World Alzheimer Report 2010.

Yu, "Neuroprotective effets of salidroside against beta-amyloid-induced oxidative stress in SH-SY5Y human neuroblastoma cells", Cell Mol Neurobiol DOI 10.1007/s10571-008-9284-z, 12 pages.

Zhang, et al., "Application of Kinetic Redolution Using HCS as Chiral Auxiliary: Novel Synthesis of beta-blockers (s)-Betaxolol and (S)-Metoprolol", Chirality 21: 745-750 (2009).

Zhang, "Neuroprotective effets of salidroside against beta-amyloid-induced oxidative stress in SH-SY5Y human neuroblastoma cells", Neurochemistry International 57 (2010) 547-555.

Zhang, "Non-enzymatic kinetic resolution of Beta-amino alcohols using C-12 higher carbon sugar as a chiral auxiiary", Tetrahedron: Asymmetry 19 (2008) 512-517.

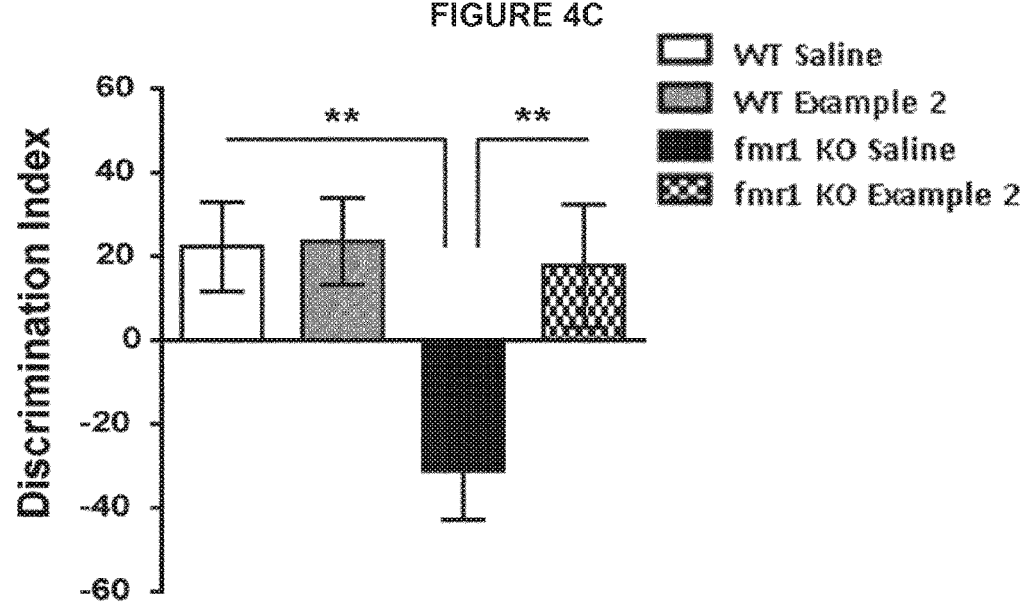

HYDROXY ALIPHATIC SUBSTITUTED PHENYL AMINOALKYL ETHER DERIVATIVES

This is a divisional application of U.S. patent application Ser. No. 14/654,661, filed Jun. 22, 2015, which is a national stage application based on International Application PCT/EP2013/077731, filed on Dec. 20, 2013, which claims the benefit of EP Application No. 12382527.5, filed Dec. 21, 2012. The entire disclosure of each prior application is incorporated by reference herein in its entirety.

FIELD OF THE INVENTION

The present invention relates to hydroxy aliphatic substituted phenyl aminoalkyl ether compounds and their use in the preparation of pharmaceutical compositions to promote neuroplasticity, learning and memory in nervous system diseases, and developmental, behavioral and mental disorders.

BACKGROUND OF THE INVENTION

Neuroplasticity is the ability of the nervous system to respond to intrinsic or extrinsic stimuli by reorganizing its structure, function and connections. Neuroplasticity is one of the most important areas in contemporary neuroscience. It is widely considered to be a cellular mechanism underlying learning and memory (Harnessing neuroplasticity for clinical applications. Cramer, S. C. et al. Brain. 2011; 134(Pt. 6): 1591-609).

Neuroplastic changes have been observed in a large variety of diseases, such as Alzheimer's disease; amyotrophic lateral sclerosis; Angelman syndrome; Asperger syndrome; autistic disorders; bipolar disorder; brain injury; Creutzfeldt-Jakob disease; depression; Down syndrome; epilepsy; fragile X syndrome; Friedrich's ataxia; frontotemporal dementia; frontotemporal lobar degeneration; Huntington's disease; Lewy body disease; multiple sclerosis; multiple system atrophy; Parkinson's disease; Pick's disease; post-traumatic stress disorders; prion disorders; Rett syndrome; schizophrenia; spinal and bulbar muscular atrophy; spinal cord injuries; spinocerebellar ataxias; stroke; supranuclear palsy; progressive and tuberous sclerosis.

The scientific challenge to alleviate human suffering in these diseases is enormous.

Neurodegenerative Diseases

The 21st century is facing an epidemic of neurodegenerative diseases. Alzheimer's disease, Huntington's disease and Parkinson's disease are highly prevalent all over the world and have a high social and economic impact.

The Johns Hopkins Bloomberg School of Public Health has estimated the prevalence of Alzheimer's disease at 26.6 million people worldwide, with an estimated 5.4 million in the U.S. alone. By 2050, these figures are expected to have risen to 106 million and 16 million, respectively (Brookmeyer, R. et al. Alzheimers Dement 2007, 3(3): 186-91; Alzheimers Dement 2011, 7(2): 208-44. Parkinson's disease affects around 0.3% of the population in general, with 1% of those over 60 years of age affected and 4-5% of those over 85 years of age (Rao, S. S. et al. Am Fam Physician 2006, 74(12): 2046-54).

Huntington's disease has a worldwide prevalence of 5.7 per 100,000 inhabitants (Pringsheim, T. et al. Mov Disord 2012, 27(9): 1083-91).

The costs associated with these conditions are very high. In 2010, the overall cost of dementia reached USD 604 billion (World Alzheimer Report 2010: The global economic impact of dementia; Alzheimer's Disease International, 2010) and the cost of Alzheimer's disease is likely to rise to USD 1.1 trillion by 2050 (2011 Alzheimer's disease facts and figures; Alzheimer's Association, March 2011). Similarly, Parkinson's disease is estimated to cause yearly costs of approximately USD 23 million (Huse, D. M. et al. Mov Disord 2005, 20(11): 1449-54).

Given the social and economic impact of neurodegenerative diseases, better, more effective treatments are urgently needed. The Alzheimer's Association argues that were a treatment to be discovered that could delay the onset of the disease by 5 years, the number of patients in the U.S. with dementia would fall by nearly 2 million (Brookmeyer, R. et al. Am J Publ Health 1998, 88(9): 1337-; Coley, N. et al. Epidemiol Rev 2008, 30: 35-66) resulting in a yearly saving in health care costs of USD 50 billion (Mount, C. and Downton, C. Nat Med 2006, 12(7): 780-4).

Pharmacotherapies to increase neuroplasticity through molecular manipulation of different cellular and synaptic pathways are needed, since at present only modest or small benefits have been achieved in the treatment of the above-mentioned diseases.

Thus, there is a need to discover new drugs which are able to promote neuroplasticity in the context of nervous system diseases and developmental, behavioral and mental disorders where cognitive deficits—particularly in learning and memory—are associated with illness.

The role of herbal medicines in the treatment of some of these diseases has become well established, with clinical evidence for phytotherapeutic preparations using plants. We have reviewed different plants and their components as a source of active agents that may serve as leads and scaffolds for the development of efficacious drugs for a multitude of CNS diseases, as well as developmental, behavioral and mental disorders.

Salidroside is one of the most potent compounds in *Rhodiola rosea* L. It is well known as an adaptogen in tradition Chinese medicine and has been reported to show diverse pharmacological activities, including antioxidant (Prasad, D. et al. Mol Cell Biochem 2005, 275(1-2); 1-6), antiaging (Mao, G.maoX. Biomed. Environ. Sci. 2010, 23(2): 161-6) and anti-fatigue (Darbinyan, V. Phytomedicine 2000, 7(5): 365-71). Many reports and reviews reveal that salidroside exhibits potent neuroprotective activity (Zhang, L. Neurochem Int 2010, 57(5): 547-55; Li, Q. Y. et al. Neurosci Lett 2010, 481(3): 154-8. Yu, S. et al. Cell Mol. Neurobiol. 2008, 28(8): 1067-8). We selected tyrosol, the aglycone of salidroside, as a starting material to design new compounds for the treatment of neurological disorders.

After intense investigations the present inventors found that the compounds of formula (I) have utility as neuroplasticity promoters and are useful in the enhancement of memory consolidation and learning and in CNS diseases and/or mental disorders associated with cognitive deficits. Additionally, the compounds show pleiotropic effects which can be explained mechanistically by their actions on different targets, i.e., binding to receptors and inhibition of enzymes. These effects may allow the use of the compounds in the treatment of a variety of other diseases, including pain and depression. In particular, the compounds of formula (I) have been shown to be highly active in animal models of memory consolidation after acute administration, with long-lasting effects, as well as in models of pain and depression.

These characteristics surprisingly differentiate compounds of formula (I) from those described in the literature.

BRIEF DESCRIPTION OF THE FIGURES

FIG. 4 shows the results of the social behavior test. FIG. 4C plots the Discrimination index (time exploring the novel stimulus−time exploring the familiar stimulus/total time of exploration×100). N=10-12 mice per group. Mice had received an acute i.p. injection of saline (WT $1^{st}$ bar, fmr1 KO $3^{rd}$ bar) or 30 mg/kg Example 2 (Wild Type $2^{nd}$ bar, fmr1 KO $4^{th}$ bar) 24 h before the session. Data are expressed as mean±S.E.M. Two way ANOVA Treatment effect Φ $p<0.05$, Genotype x Treatment interaction $p<0.05$, Bonferroni as post hoc *$p<0.001$, $p<0.01$, *$p<0.05$.

DESCRIPTION OF THE INVENTION

Figure 1:
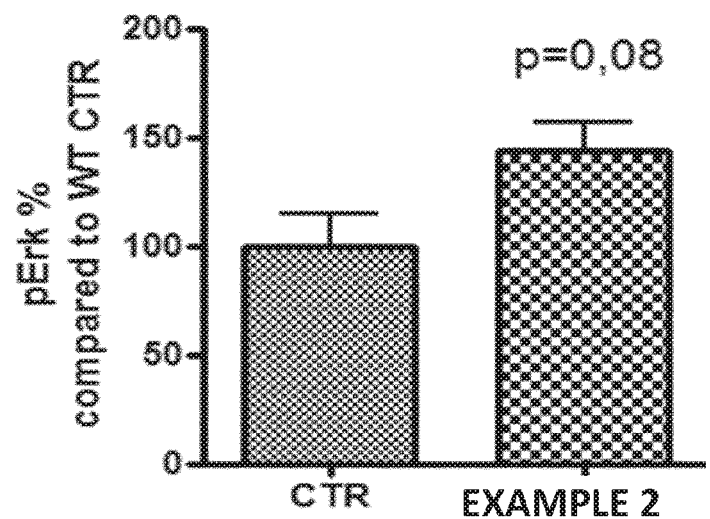
FIG. 1 shows the levels of p-ERK at the hippocampus of test mice after intraperitoneal administration of the compound of Example 2 at a dose of 30 mg/kg compared to a control wherein the level of the control mice have been taken as reference value (100% p-ERK phosphorylation).

The inventors have obtained new hydroxy aliphatic substituted phenyl aminoalkyl ether derivatives capable of increasing the phosphorylation of ERK and/or Akt kinases. This activity makes them promising candidates as neuroplasticity promoters useful in the enhancement of memory consolidation and learning and in CNS diseases and/or mental disorders associated with cognitive deficits. Advantageously, these new drugs also have the capacity of inhibiting serotonin reuptake (making them candidates for the treatment of pain) and/or the ability to inhibit the reuptake of norepinephrine and/or serotonin (making them potential candidates for the treatment of depression).

In one aspect, the present invention provides compounds having formula (I)

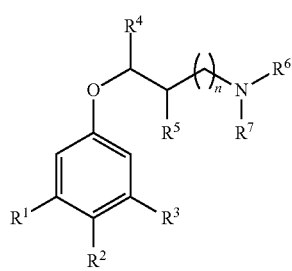

(I)

wherein,
$R^1$, $R^2$ and $R^3$ are independently selected from the group consisting of H and A-OR$^8$;
wherein A is a biradical selected from the group consisting of $C_1$-$C_5$ alkylene and $C_2$-$C_6$ alkenylene;
with the proviso that
when $R^2$ is A-OR$^8$, then $R^1$ and $R^3$ must be H;
when $R^2$ is H, then $R^1$ and $R^3$ must be A-OR$^8$;
$R^4$ is selected from the group consisting of H; $C_5$-$C_7$ cycloalkyl; $C_6$-$C_{10}$ aryl and a 5- or 6-membered monocyclic heteroaryl group which contains 1 or 2 heteroatoms in the ring independently selected from the group consisting of N, O and S; all of them optionally substituted by one or more groups selected from the group consisting of halogen; —OH; $C_1$-$C_8$ alkyl; $C_1$-$C_8$ alkoxy; —CN; —NO$_2$; —COOH and —NH$_2$;
and either:
a) $R^5$ is selected from the group consisting of H and an 8-, 9- or 10-membered bicyclic heteroaryl group which contains 1 or 2 heteroatoms independently selected from the group consisting of N, O and S; all of them optionally substituted by one or more groups selected from the group consisting of halogen; —OH; $C_1$-$C_8$ alkyl; $C_1$-$C_8$ alkoxy; —CN; —NO$_2$: —COOH and —NH$_2$; $R^6$ is selected from the group consisting of H; $C_1$-$C_3$ alkyl and $C_1$-$C_8$ acyl; and $R^7$ is selected from the group consisting of H and $C_1$-$C_3$ alkyl;
b) $R^5$ and $R^6$ taken together form a group selected from the group consisting of —O—CH$_2$—CH$_2$— and —CH(R$^{11}$)—CH$_2$—CH$_2$—; and $R^7$ is H; or
c) $R^5$ is H; and $R^6$ and $R^7$ taken together form a group —(CH$_2$)$_m$—CO—;
$R^8$ is selected from H; glycosyl; acetyl; valproyl and lipoyl;
$R^{11}$ is a phenyl group optionally substituted by one or more substituents selected from the group consisting of halogen; —OH and —NH$_2$;
n is an integer selected from 0, 1 and 2;
m is an integer selected from 2, 3 and 4;
with the proviso that when $R^4$ and $R^5$ are both H, then $R^6$ and $R^7$ taken together form a group —(CH$_2$)$_m$—CO—;
or a pharmaceutically acceptable salt or stereoisomer thereof.

In one embodiment, the present invention provides a compound of formula (I) wherein $R^1$, $R^2$ and $R^3$ are independently selected from the group consisting of H and A-OR$^8$;
wherein A is a biradical selected from the group consisting of $C_1$-$C_6$ alkylene and $C_2$-$C_5$ alkenylene;
with the proviso that
when $R^2$ is A-OR$^8$, then $R^1$ and $R^3$ must be H;
when $R^2$ is H, then $R^1$ and $R^3$ must be A-OR$^8$;
$R^4$ is selected from the group consisting of H; $C_{5-7}$ cycloalkyl; a $C_6$-$C_{10}$ aryl and a 5- or 6-membered monocyclic heteroaryl group which contains 1 or 2 heteroatoms in the ring independently selected from the group consisting of N, O and S; all of them optionally substituted by one or more groups selected from halogen; —OH; $C_1$-$C_8$ alkyl; $C_1$-$C_8$ alkoxy; —CN; —NO$_2$; —COOH and —NH$_2$; and either:
a) $R^5$ is selected from the group consisting of H and an 8-, 9- or 10-membered bicyclic heteroaryl group which contains 1 or 2 heteroatoms independently selected from the group consisting of N, O and S optionally substituted by one or more groups selected from the group consisting of halogen; —OH; $C_1$-$C_6$ alkyl; $C_1$—C alkoxy; —CN; —NO$_2$; —COOH and —NH$_2$, $R^6$ is selected from the group consisting of H; $C_1$-$C_3$ alkyl and $C_1$-$C_8$ acyl; and $R^7$ is selected from the group consisting of H and $C_1$-$C_3$ alkyl;
b) $R^5$ and $R^6$ taken together form a group selected from the group consisting of —O—$CH_2$—$CH_2$— and —CH($R^{11}$)—$CH_2$—$CH_2$—; and $R^7$ is H; or
c) $R^5$ is H; and $R^6$ and $R^7$ taken together form a group —$(CH_2)_m$—CO—;
$R^8$ is selected from the group consisting of H; glycosyl; acetyl; valproyl and lipoyl;
$R^{11}$ is a phenyl group optionally substituted by halogen; —OH and —$NH_2$;
n is an integer selected from 0, 1 and 2;
m is an integer selected from 2, 3 and 4;
with the proviso that when $R^4$ and $R^5$ are both H, then $R^6$ and $R^7$ taken together form a group —$(CH_2)_m$—CO—;
or a pharmaceutically acceptable salt or stereoisomer thereof.

In another embodiment, the present invention provides a compound of formula (I) wherein,
$R^1$, $R^2$ and $R^3$ are independently selected from the group consisting of H and A-$OR^8$;
wherein A is a biradical selected from the group consisting of $C_1$-$C_6$ alkylene; with the proviso that
when $R^2$ is A-$OR^8$, then $R^1$ and $R^3$ must be H;
when $R^2$ is H, then $R^1$ and $R^3$ must be A-$OR^8$;
$R^4$ is selected from the group consisting of H; $C_{5-7}$ cycloalkyl; a $C_6$-$C_{10}$ aryl and a 5- or 6-membered monocyclic heteroaryl group which contains 1 or 2 heteroatoms in the ring independently selected from the group consisting of N, O and S; all of them optionally substituted by one or more groups selected from the group consisting of halogen; —OH; $C_1$-$C_8$ alkyl; $C_1$-$C_8$ alkoxy; —CN; —$NO_2$; —COOH and —$NH_2$;
and either:
a) $R^5$ is selected from the group consisting of H and an 8-, 9- or 10-membered bicyclic heteroaryl group which contains 1 or 2 heteroatoms independently selected from the group consisting of N, O and S optionally substituted by one or more groups selected from the group consisting of halogen; —OH and $C_1$-$C_8$ alkyl; $R^6$ is selected from the group consisting of H; $C_1$-$C_3$ alkyl and $C_1$-$C_8$ acyl; and $R^7$ is selected from the group consisting of H and $C_1$-$C_3$ alkyl;
b) $R^5$ and $R^6$ taken together form a group selected from the group consisting of —O—$CH_2$—$CH_2$— and —CH($R^{11}$)—$CH_2$—$CH_2$—; and $R^7$ is H; or
c) $R^5$ is H; and $R^6$ and $R^7$ taken together form a group —$(CH_2)_m$—CO—;
$R^8$ is selected from the group consisting of H; glycosyl; acetyl; valproyl and lipoyl;
$R^{11}$ is a phenyl group optionally substituted by halogen; —OH and —$NH_2$;
n is an integer selected from 0, 1 and 2;
m is an integer selected from 2, 3 and 4;
with the proviso that when $R^4$ and $R^5$ are both H, then $R^6$ and $R^7$ taken together form a group —$(CH_2)_m$—CO—;
or a pharmaceutically acceptable salt or stereoisomer thereof.

In another embodiment, the present invention provides a compound of formula (I) wherein,
$R^1$, $R^2$ and $R^3$ are independently selected from the group consisting of H and A-$OR^8$;
wherein A is a biradical selected from the group consisting of $C_1$-$C_6$ alkylene; with the proviso that
when $R^2$ is A-$OR^8$, then $R^1$ and $R^3$ must be H;
when $R^2$ is H, then $R^1$ and $R^3$ must be A-$OR^8$;
$R^4$ is selected from the group consisting of H; a $C_6$-$C_{10}$ aryl and a 5- or 6-membered monocyclic heteroaryl group which contains 1 or 2 heteroatoms in the ring independently selected from the group consisting of N, O and S; all of them optionally substituted by one or more groups selected from the group consisting of halogen; —OH and $C_1$-$C_8$ alkyl;
and either:
a) $R^5$ is selected from the group consisting of H and an 8-, 9- or 10-membered bicyclic heteroaryl group which contains 1 or 2 heteroatoms independently selected from the group consisting of N, O and S optionally substituted by one or more groups selected from the group consisting of halogen; —OH and $C_1$-$C_8$ alkyl; $R^6$ is selected from the group consisting of H and $C_1$-$C_3$ alkyl; and $R^7$ is selected from the group consisting of H and $C_1$-$C_3$ alkyl;
b) $R^5$ and $R^6$ taken together form a group selected from the group consisting of —O—$CH_2$—$CH_2$— and —CH($R^{11}$)—$CH_2$—$CH_2$—; and $R^7$ is H; or
c) $R^5$ is H; and $R^6$ and $R^7$ taken together form a group —$(CH_2)_m$—CO—;
$R^8$ is selected from the group consisting of H; acetyl; valproyl and lipoyl;
$R^{11}$ is a phenyl group optionally substituted by halogen and —OH;
n is an integer selected from 0, 1 and 2;
m is an integer from 3 and 4;
with the proviso that when $R^4$ and $R^5$ are both H, then $R^6$ and $R^7$ taken together form a group —$(CH_2)_m$—CO—;
or a pharmaceutically acceptable salt or stereoisomer thereof.

In yet another embodiment, the present invention provides a compound of formula (I) wherein,
$R^1$ and $R^3$ represent hydrogen atoms;
$R^2$ is a group A-$OR^8$; wherein A represents $C_1$-$C_6$ alkylene biradical;
$R^4$ is selected from the group consisting of H; a $C_6$-$C_{10}$ aryl and a 5- or 6-membered monocyclic heteroaryl group which contains 1 or 2 heteroatoms in the ring independently selected from the group consisting of N, O and S; and either:
a) $R^5$ is H; $R^6$ is selected from the group consisting of H and $C_1$-$C_3$ alkyl; and $R^7$ is H;
b) $R^5$ and $R^6$ taken together form a group selected from the group consisting of —O—$CH_2$—$CH_2$— and —CH($R^{11}$)—$CH_2$—$CH_2$—; and $R^7$ is H; or
c) $R^5$ is H; and $R^6$ and $R^7$ taken together form a group —$(CH_2)_m$—CO—; $R^8$ is H;
$R^{11}$ is a phenyl group optionally substituted by halogen;
n is an integer selected from 0, 1 and 2;
m is an integer from 3 and 4;
with the proviso that when $R^4$ and $R^5$ are both H, then $R^6$ and $R^7$ taken together form a group —$(CH_2)_m$—CO—;
or a pharmaceutically acceptable salt or stereoisomer thereof.

In another embodiment, the present invention provides a compound of formula (I) in the form of a salt with an acid selected from the group consisting of ascorbic acid, caffeic acid, ferulic acid, lipoic acid and valproic acid.

In yet another embodiment, the present invention provides a compound of formula (I) selected from the group consisting of:
1-[2-[4-(2-Hydroxyethyl)phenoxy]ethyl]pyrrolidin-2-one;
2-[4-[3-(Methylamino)-1-phenylpropoxy]phenyl]ethanol hydrochloride;

(R)-2-[4-[3-(Methylamino)-1-phenylpropoxy]phenyl]ethanol hydrochloride;
(S)-2-[4-[3-(Methylamino)-1-phenylpropoxy]phenyl]ethanol hydrochloride;
2-[4-[3-(Methylamino)-1-phenylpropoxy]phenyl]ethanol L-ascorbic acid salt;
2-[4-[3-(Methylamino)-1-phenylpropoxy]phenyl]ethanol ferulic acid salt;
2-[4-[3-(Methylamino)-1-phenylpropoxy]phenyl]ethanol caffeic acid salt;
2-[4-[3-(Methylamino)-1-phenylpropoxy]phenyl]ethanol valproic acid salt;
2-[4-[3-(Methylamino)-1-phenylpropoxy]phenyl]ethanol (R)-lipoic acid salt;
4-[3-(Methylamino)-1-phenylpropoxy]phenethyl acetate hydrochloride;
N-[3-[4-(2-Hydroxyethyl)phenoxy]-3-phenylpropyl]-N-methyl-2-propylpentanamide;
2-[4-(3-Amino-1-phenylpropoxy)phenyl]ethanol hydrochloride;
(R)-2-[4-[3-(Methylamino)-1-(thiophen-2-yl)propoxy]phenyl]ethanol;
4-[4-[3-(Methylamino)-1-phenylpropoxy]phenyl]butan-1-ol hydrochloride;
(E)-tert-Butyl[3-[4-(3-hydroxyprop-1-enyl)phenoxy]-3-phenylpropyl](methyl)carbamate;
3-[4-[3-(Methylamino)-1-phenylpropoxy]phenyl]propan-1-ol hydrochloride;
[4-[3-(Methylamino)-1-phenylpropoxy]phenyl]methanol hydrochloride;
2-[4-(Morpholin-2-ylmethoxy)phenyl]ethanol hydrochloride;
[5-[3-(Methylamino)-1-phenylpropoxy]-1,3-phenylene]dimethanol hydrochloride;
2,2'-[5-[3-(Methylamino)-1-phenylpropoxy]-1,3-phenylene]diethanol;
3,3'-[5-[3-(Methylamino)-1-phenylpropoxy]-1,3-phenylene]dipropan-1-ol;
4,4'-[5-[3-(Methylamino)-1-phenylpropoxy]-1,3-phenylene]dibutan-1-ol;
(2R,3S,4S,5R,6R)-2-(Hydroxymethyl)-6-[4-[3-(methylamino)-1-phenylpropoxy]phenethoxy]tetrahydro-2H-pyran-3,4,5-triol;
2-[4-(3-Dimethylamino-1-phenylpropoxy)phenyl]ethanol;
4-[4-(3-Methylamino-1-phenylpropoxy)phenyl]but-2-en-1-ol;
6-[4-(3-Methylamino-1-phenylpropoxy)phenyl]hexan-1-ol;
6-[4-(3-Methylamino-1-phenylpropoxy)phenyl]hex-5-en-1-ol;
(S)2-[4-(3-Methylamino-1-thiophen-2-ylpropoxy)phenyl]ethanol;
2-[4-(Morpholin-2-yl(phenyl)methoxy)phenyl]ethanol;
2-[4-[[(3S,4R)-4-(4-Fluorophenyl)piperidin-3-yl]methoxy]phenyl]ethanol;
2-[2-Dimethylamino-1-[4-(2-hydroxyethyl)phenoxy]ethyl]cyclohexanol;
1-[2-Dimethylamino-1-[4-(2-hydroxyethyl)phenoxy]-ethyl]-cyclohexanol;
2-[4-[2-(4-Fluoroindol-1-yl)-4-methylaminobutoxy]phenyl]ethanol;
2-Propylpentanoic acid 2-[4-(3-methylamino-1-phenylpropoxy)phenyl]ethyl ester;
5(R)-[1,2]-Dithiolan-3-ylpentanoic acid 2-[4-(3-methylamino-1-phenylpropoxy)phenyl]ethyl ester.

In another aspect, the present invention provides pharmaceutical compositions comprising a compound as defined above and one or more pharmaceutically acceptable carriers.

In another aspect, the present invention provides a compound as defined above for use as a medicament, in particular for use in the treatment of nervous system diseases and/or the treatment of developmental, behavioral and/or mental disorders associated with cognitive deficits, particularly learning and memory disorders. Non-limiting examples of such diseases and/or disorders are Down syndrome, Angelman syndrome, Rett syndrome, autistic disorders, fragile X disorder Asperger syndrome, depression, bipolar disorder, schizophrenia, cerebral dementias post traumatic stress disorders, Pick's disease and sleep disorders, amyotrophic lateral sclerosis, fronto temporal dementia and Friedrich's ataxia, neuropathic, Alzheimer's disease, Parkinson's disease, Huntington's disease, autistic disorders, Down syndrome, fragile X syndrome and Rett syndrome.

In another aspect, the present invention provides a compound as defined above for use as a medicament, in particular for use in the treatment of depression.

In another aspect, the present invention provides a compound as defined above for use as a medicament, in particular for use in the treatment of pain.

In another aspect, the present invention provides comprising a compound of formula (I) as defined above and another agent selected from the group consisting of acetylcholinesterase inhibitors such as rivastigmine, donepezil, galantamine and huperzine A; NMDA antagonists such as memantine and latrepirdine; histamine $H_3$ receptor antagonists such as pitolisant, SAR-110894, ABT-288, S-38093 and AZD-5213; beta-secretase 1 (BACE1) inhibitors such as resveratrol, HPP-854, LY-2886721, E-2609 and MK-8931; antiamyloidogenic agents such as (−)-epigallocatechin gallate, (+)-phenserine and AAD-2004; 5-$HT_6$ receptor antagonists such as Lu-AE-58054, AVN-322, GSK-215083, GSK-742457; 5-$HT_4$ receptor agonists such as SL-65.0102 and BIMU-1; MAO-B inhibitors such as rasagiline, ladostigil and RG-1577; GABA(A) receptor modulators such as etazolate and RG-1662 muscarinic $M_1$ receptor agonists such as sabcomeline and MCD-386; and gamma-secretase inhibitors such as pinitol.

In another aspect, the present invention provides the use of a compound as defined above for the manufacture of a medicament.

In another aspect, the present invention provides the use of a compound as defined above for the manufacture of a medicament for the treatment of nervous system diseases and/or the treatment of developmental, behavioral and/or mental disorders associated with cognitive deficits.

In another aspect, the present invention provides the use of a compound as defined above for the manufacture of a medicament for the treatment of nervous system diseases and/or developmental, behavioral and/or mental disorders associated with learning deficits or with memory deficits.

In another aspect, the present invention provides the use of a compound as defined above for the manufacture of a medicament for the treatment of developmental disorders associated with cognitive deficits selected from the group consisting of Down syndrome, Angelman syndrome, Rett syndrome, autistic disorders, fragile X disorder and Asperger syndrome.

In another aspect, the present invention provides the use of a compound as defined above for the manufacture of a medicament for the treatment of behavioural and/or mental disorders associated with cognitive deficits selected from the group consisting of depression, bipolar disorder, schizophrenia, cerebral dementias, post traumatic stress disorders, Pick's disease and sleep disorders.

In another aspect, the present invention provides the use of a compound as defined above for the manufacture of a medicament for the treatment of neurodegenerative disorders associated with cognitive deficits selected from the group consisting of Alzheimer's disease, Parkinson's disease, Huntington's disease, amyotrophic lateral sclerosis, fronto temporal dementia and Friedrich's ataxia.

In another aspect, the present invention provides the use of a compound as defined above for the manufacture of a medicament for the treatment of a condition selected from the group consisting of neuropathic pain, fibromyalgia, epilepsy and stroke.

In another aspect, the present invention provides a method of treatment or prevention of nervous system diseases and/or the treatment of developmental, behavioral and/or mental disorders associated with cognitive deficits by administering a compound as defined above.

In another aspect, the present invention provides a method of treatment or prevention of nervous system diseases and/or developmental, behavioral and/or mental disorders associated with learning deficits or with memory deficits by administering a compound as defined above.

In another aspect, the present invention provides a method of treatment or prevention of developmental disorders associated with cognitive deficits selected from the group consisting of Down syndrome, Angelman syndrome, Rett syndrome, autistic disorders, fragile X disorder and Asperger syndrome by administering a compound as defined above.

In another aspect, the present invention provides a method of treatment or prevention of behavioural and/or mental disorders associated with cognitive deficits selected from the group consisting of depression, bipolar disorder, schizophrenia and cerebral dementias by administering a compound as defined above.

In another aspect, the present invention provides a method of treatment or prevention of neurodegenerative disorders associated with cognitive deficits selected from the group consisting of Alzheimer's disease, Parkinson's disease, Huntington's disease and amyotrophic lateral sclerosis by administering a compound as defined above.

In another aspect, the present invention provides a method of treatment or prevention of neuropathic pain or fibromyalgia by administering a compound as defined above.

Pharmacological Activity

Neuroplasticity is the process that underlies neurogenesis and plays a pivotal role in learning and memory processes. Studies have been performed on the molecular and cellular mechanisms underlying neural plasticity responses in learning and memory, as well as anxiety, depression, allodynia, neuropathic pain and drug abuse, some of the most exciting areas of research in neuroscience (Enciu, A. M. et al. BMC Neurology 2011, 11: 75; Caroni, P. et al. Nat Rev Neurosci 2012, 13(7): 478-90; Carlson, P. J. et al. NeuroRx 2006, 3(1): 22-41; Disner, S. G. et al. Nat Rev Neurosci 2011, 12(8): 467-77; Latremoliere, A. and Woolf, C. J. J Pain 2009, 10(9): 895-26; Madsen, H. B. et al. Front Mol Neurosci 2012, 5: 99).

Two brain structures, the amygdala and the hippocampus, play key roles in interpreting what is stressful and determining appropriate responses. The hippocampus, a key structure for memories of events and contexts, expresses receptors that enable it to respond to different effectors. It undergoes atrophy in a number of psychiatric disorders (Atmaca, M. and Yildirim, H. Depress Res Treat 2012, 2012: 485249; Echdvarri, C. et al. Brain Struct Funct. 2011, 215(3-4): 265-71) and responds to stressors with changes in excitability, decreased dendritic branching and reduction in the number of neurons in the dentate gyrus (deToledo-Morrell, L. et al. Prog Brain Res 2007, 163: 741-53). The amygdala, which is important for "emotional memories", becomes hyperactive in posttraumatic stress disorder (Lakshminarasimhan, H. and Chattarji, S. PLoS ONE 2012, 7(1): e30481) and depressive illness (Luking, K. R. et al. Am Acad Child Adolesc Psychiatry. 2011, 50(10): 1027-41).

The molecular changes that regulate the cellular mechanism of neuroplasticity involve the activation of the neurotransmitter system and cell signaling pathways that regulate and control gene expression and subsequent protein synthesis.

Significant overlap exists between the molecular mechanisms of induction of neuroplasticity and enlargement and stabilization of spines in the neurons. Calcium/calmodulin-dependent protein kinase type II (CAMK II) contributes to the enlargement of neuron spines (Yamagata, Y. et al. J Neurosci 2009, 29(23): 7607-18; Lisman, J. et al. Nat Rev Neurosci 2012, 13(3): 169-82), whereas the local regulation of protein synthesis involving the signaling cascade AMPK/ ERK or phosphoinositide 3-kinase (PI3K/Akt) pathways downstream of the growth factor receptor Trk-B activated, the mammalian target of rapamycin (mTOR) signaling complex and the translation of mRNAs that encode proteins such as activity-regulated cytoskeleton-related protein (ARC) or CAMK II have been related with stabilization of the spine (Caroni, P. et al. Nat Rev Neurosci 2012, 13(7): 478-90) It has been described that PKC contributes both to enlargement and stabilization of spines and is thus implicated in long-term potentiation maintenance and behavioral learning (Sacktor, T. C. Nat Rev Neurosci 2911, 12(1):9-15).

Compounds of formula (I) are active in the following mechanisms of action which are involved in neuroplasticity, learning and memory: norepinephrine (NE) transporter inhibition, serotonin (5-HT) transporter inhibition, and Akt and ERK phosphorylation.

Antidepressant activity can be related to norepinephrine, serotonin and dopamine reuptake inhibitors.

Analgesic activity can be related to norepinephrine and serotonin reuptake inhibitors.

In vivo, compounds of formula (I) surprisingly were shown to improve learning and memory after oral administration, demonstrating a long-lasting effect. This behavior contrasts with that of other NE/5-HT transporter inhibitors and MAO-B inhibitors (such as rasagiline), which are only active after prolonged administration (30-40 days).

Compounds of formula (I) may be administered for human or veterinary use orally, parenterally, subcutaneously, rectally, topically, by inhalation and locally.

The present invention also provides for compounds of formula (I), pharmaceutical compositions employing such compounds and methods of using such compounds alone or in combination with other therapeutic agents for treating, preventing or delaying the progression of the above-mentioned diseases.

The compounds of formula (I) of the invention can be prepared as shown in the following reaction schemes and the description thereof wherein temperatures are expressed in degrees Celsius.

The compounds of formula (I) of the present invention can be prepared as shown in the following reaction schemes and the description thereof. All the stereoisomers of the compounds depicted in these schemes, unless otherwise specified, are also encompassed within the scope of this invention.

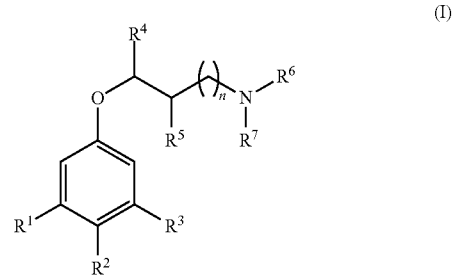

(I)

Exemplary reagents and procedures for these reactions appear hereinafter and in the working examples. Protection and deprotection, in the schemes below, may be carried out by general procedures (see, for example, Greene, T. W. and Wuts, P. G. M. Protecting Groups in Organic Synthesis (Third Edition), J. Wiley & Sons, 1999).

Scheme 1 shows the synthesis of compounds of formula (I) wherein $R^1$ and $R^3$ are hydrogen atoms and $R^2$ is $A\text{-}OR^8$ as hereinabove defined, i.e. compounds of formula (Ia). These compounds of formula (Ia) may be prepared starting from the corresponding hydroxalkyl-, hydroxylalkenyl- or hydroxyalkynyl-phenol (II), which is commercially available or may be prepared according to general procedures. Selective protection of the phenol (II) with a phenol protecting group (PG1) such as benzyl, benzoyl, acetate and the like leads to the hydroxy derivative (III) which is at its turn reacted with an orthogonal hydroxyl protecting group (PG2) such as tert-butyldimethylsilyl, tert-butyldiphenyl, tri-isopropylsilyl, and the like to afford compound (IV). Then, selective cleavage of PG1 leads to key intermediate (V). Reaction of (V), under suitable conditions such as those of Mitsunobu reaction, with alcohols of formula (VI), wherein $R^4$, $R^5$, $R^6$ and $R^7$ are as described hereinbefore, leads to ethers of formula (VII). Deprotection of (VII) yields a compound of formula (Ib) according to the invention, wherein $R^1$ and $R^3$ are hydrogen atoms and $R^2$ is A-OH. This compound of formula (Ib) may also be converted into a compound of formula (Ia) wherein $R^8$ is different from hydrogen by the introduction of a suitable substituent $R^8$. In the particular case that $R^6$ is an acyl group it is possible to obtain the above mentioned compounds of formula (Ia) by acylation of the corresponding compound wherein $R^6$ is a hydrogen atom (i.e. by conversion of the amine group —$NR^6R^7$ wherein $R^6$ is hydrogen to the corresponding amide wherein $R^6$ is an acyl group).

Scheme 1

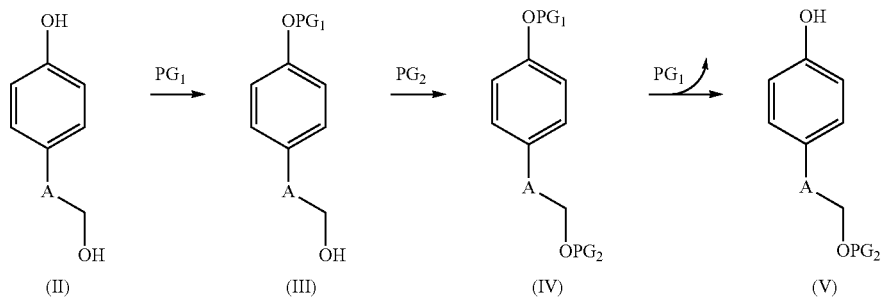

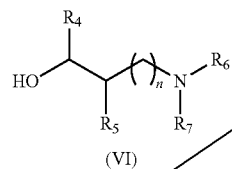

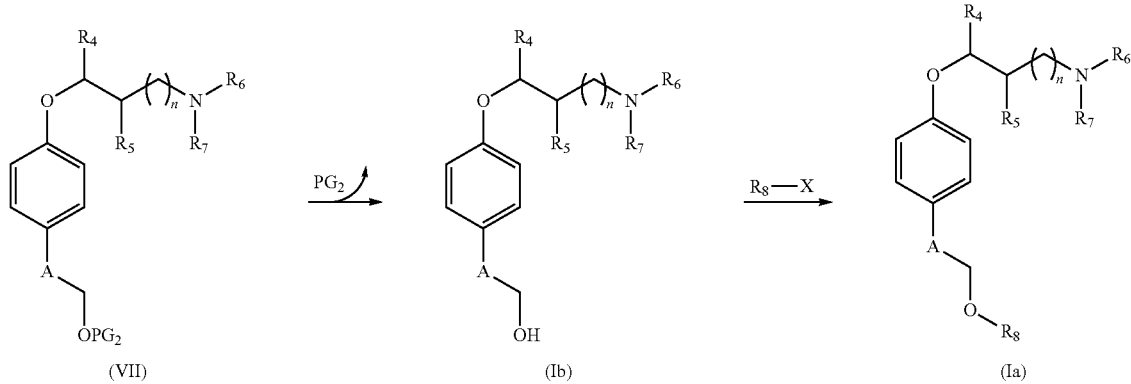

In an alternative synthetic route, shown in Scheme 2, the key intermediate (V) is reacted with compounds of formula (IX), wherein LG is a leaving group such as halogen, methylsulfonyl, p-toluenesulfonyl, trifluoromethylsulfonyl and the like, in the presence of a base such as sodium hydride, sodium methoxide and the like, to yield intermediate (VII). The latter may be converted into compounds of formula (Ia) as described hereinabove.

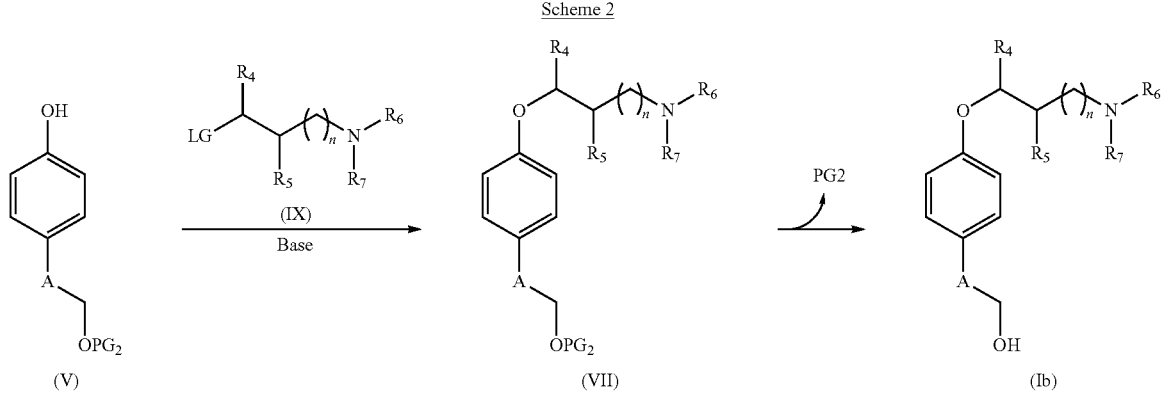

Scheme 2

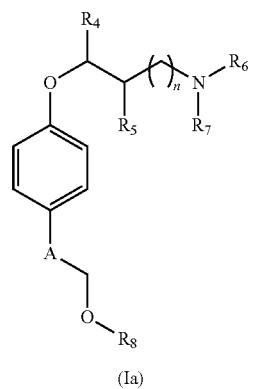

In another alternative synthetic route, shown in Scheme 3, compounds of formula (Ia) of the present invention may be also prepared starting from the corresponding esters (X), wherein $R^{12}$ is an alkyl or aryl group. Esters (X), which are commercially available or may be prepared according to general procedures, are reacted under suitable conditions such as those of Mitsunobu reaction, with alcohols of formula (VI) to yield compounds of formula (XI), wherein $R^4$, $R^5$, $R^6$ and $R^7$ are as described hereinbefore. Reduction of the ester moiety using a suitable hydride source such as lithium aluminum hydride, sodium borohydride and the like, leads to a compound of formula (Ib). The latter may be converted into compounds of formula (Ia) as described hereinabove.

Scheme 4 shows the synthesis of compounds of formula (I) wherein $R^2$ is H and both $R^1$ and $R^3$ are $A$-$OR^8$ groups as hereinabove defined, i.e., compounds of formula (Ic). These compounds (Ic) may be prepared starting from the corresponding dihydroxalkyl-, dihydroxylalkenyl- or dihydroxyalkynyl-phenol (XII), which are commercially available or may be prepared according to general procedures. Selective protection of the phenol (XII) with a phenol protecting group (PG1) such as benzyl, benzoyl, acetate and the like lead to the dihydroxy derivative (XIII) which may be at its turn reacted with an orthogonal hydroxyl protecting group (PG2) such as tert-butyldimethylsilyl, tert-butyldiphenyl, tri-iso-propylsilyl and the like to afford compound (XIV). Then, selective cleavage of PG1 leads to key intermediate

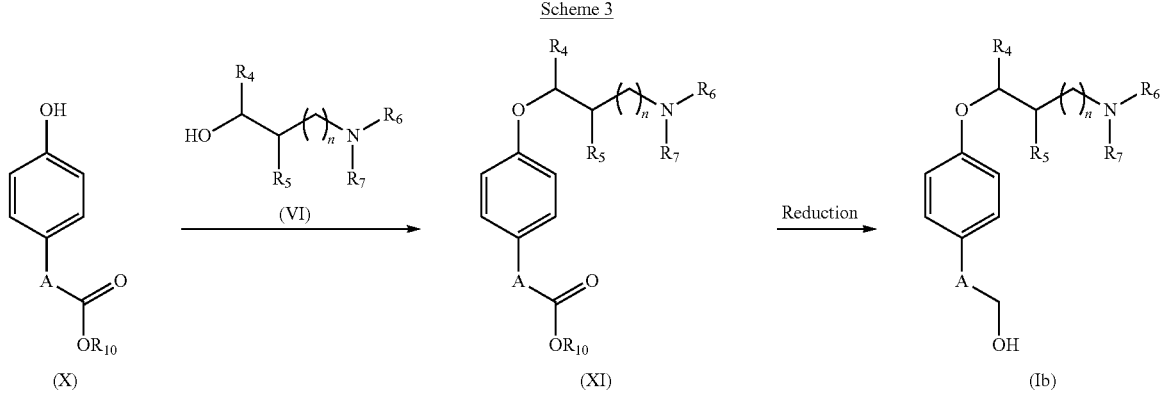

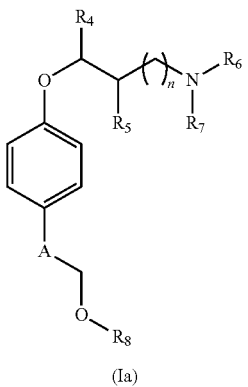

(XV). Reaction of (XV), under suitable conditions such as those of Mitsunobu reaction, with alcohols of formula (VI) leads to ethers of formula (XVI), wherein $R^4$, $R^5$, $R^6$ and $R^7$ are as described hereinbefore. Deprotection of (XVI) yields a compound of formula (Id) according to the invention, wherein $R^2$ is H and both $R^1$ and $R^3$ are A-OH groups. This compounds of formula (Ib) may also be converted into a compound of formula (Ic) wherein $R^8$ is different from hydrogen by the introduction of a suitable substituent $R^8$. In the particular case that $R^6$ is an acyl group it is possible to obtain the above mentioned compounds of formula (Ic) by acylation of the corresponding compound wherein $R^6$ is a hydrogen atom (i.e., by conversion of the amine group $-NR^6R^7$ wherein $R^8$ is hydrogen to the corresponding amide wherein $R^6$ is an acyl group).

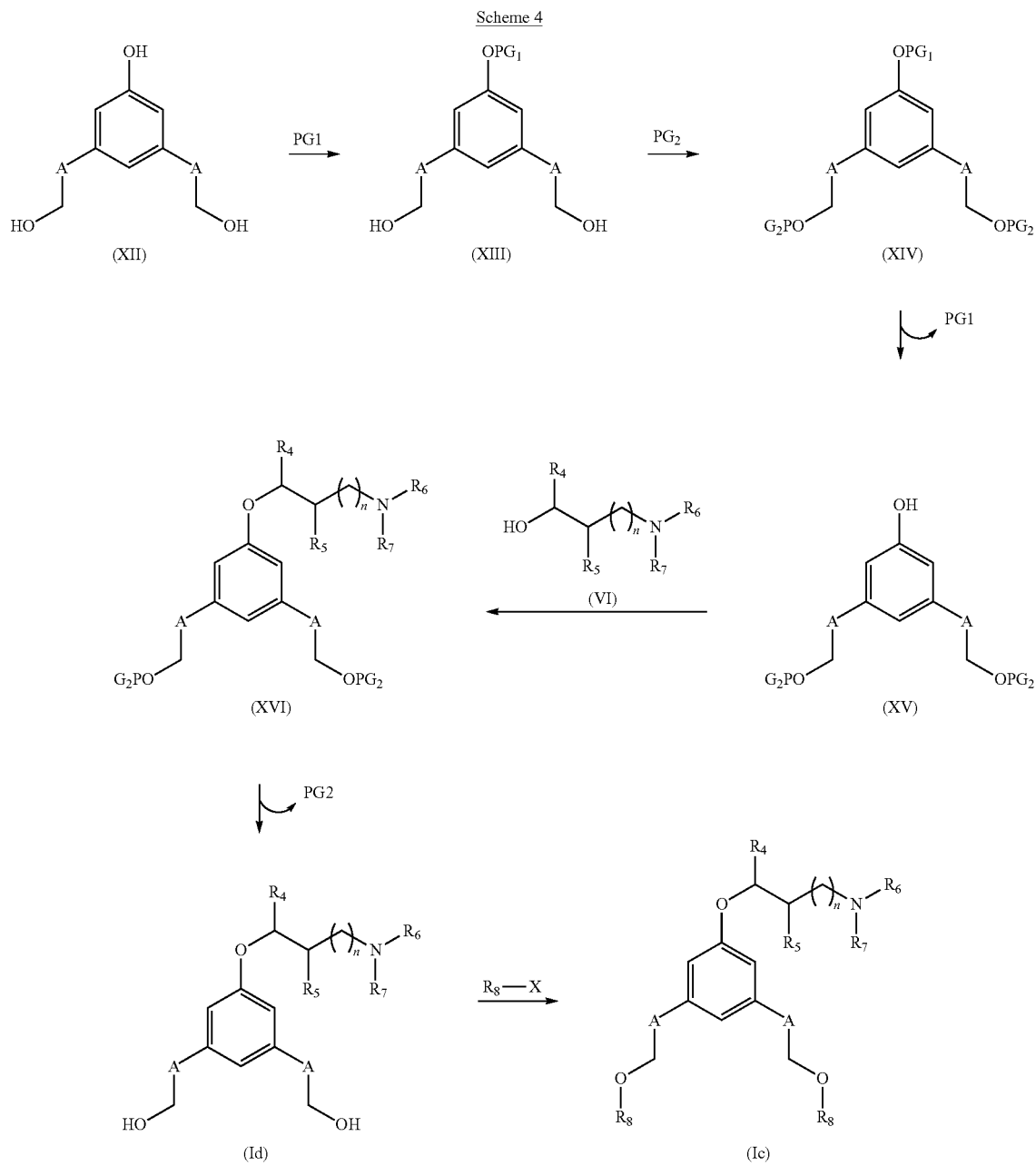

Scheme 4

In an alternative synthetic route, shown in Scheme 5, the key intermediate (XV) are reacted with compounds of formula (IX), wherein LG is a leaving group such as halogen, methylsulfonyl, p-toluenesulfonyl, trifluoromethylsulfonyl and the like, in the presence of a base such as sodium hydride, sodium methoxide and the like, to yield intermediate (XVI). The latter may be converted into compounds of formula (Ic) as described hereinabove.

Scheme 5

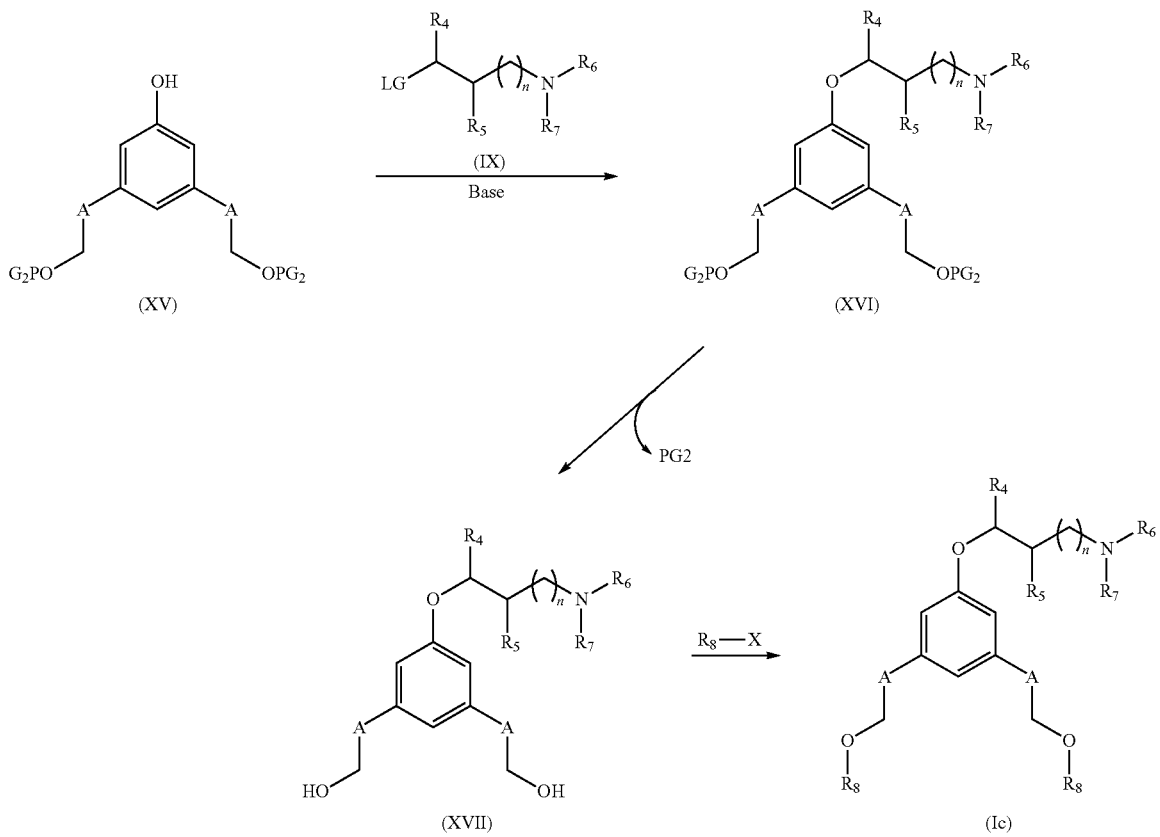

In another alternative synthetic route, shown in Scheme 6, compounds of formula (Ic) of the present invention may be also prepared starting from the corresponding diesters (VIII), wherein $R^{12}$ is an alkyl or aryl group. Diesters (VIII), which are commercially available or may be prepared according to general procedures, are reacted under suitable conditions such as those of Mitsunobu reaction, with alcohols of formula (VI) to yield compounds of formula (X), wherein $R^4$, $R^5$, $R^6$ and $R^7$ are as described hereinbefore. Reduction of both ester moieties using a suitable hydride source such as lithium aluminum hydride, sodium borohydride and the like, leads to a compound of formula (Id). The latter may be converted into compounds of formula (Ic) as described hereinabove.

Scheme 6

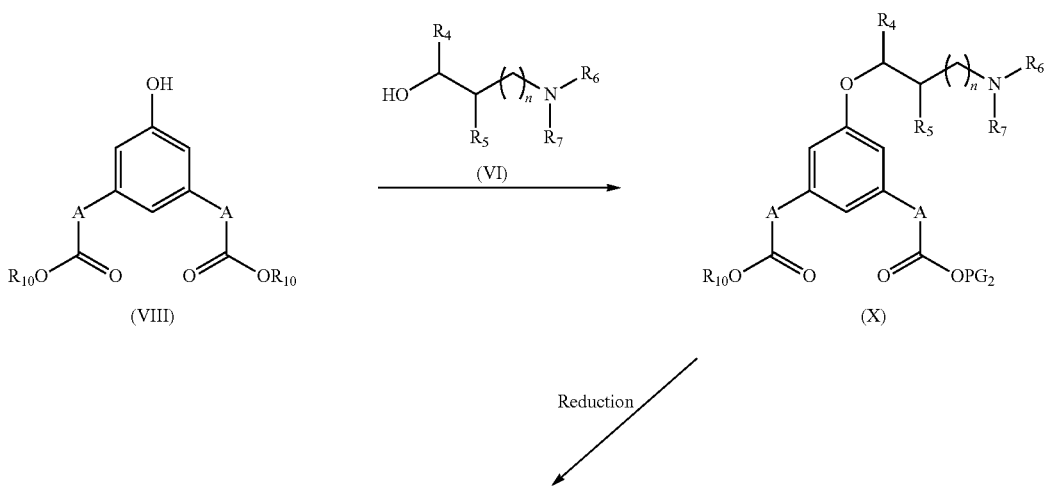

-continued (Id)

(Ic)

Compounds of formula (II), (VI), (VIII), (IX), (X) and (XII) are either commercially available or readily prepared by general methods.

The following abbreviations are employed herein:
5-HT: 5-Hydroxytryptamine or serotonin
ACN: acetonitrile
Akt (kinase): Protein Kinase B (PKB)
AMPK: AMP-activated protein kinase
ANOVA: Analysis of variance
ARC: Activity-regulated cytoskeleton-related protein
Boc2O: di-tert-butyl dicarbonate
C57BL/6 mice: C57 black 6 mice
CAMK II: Calcium/calmodulin-dependent protein kinase type II
CHO: Chinese hamster ovary
CNS: Central nervous system
DAT: Dopamine transporter
DCM: dichloromethane
DEAD: diethyl azodicarboxylate
DIBALH: diisobutylaluminium hydride
DMF: dimethylformamide
DMSO: Dimethyl sulfoxide
EGTA: ethylene glycol tetraacetic acid
ERK (kinase): Extracellular signal-regulated kinase
EtN3: triethylamine
EtOAc: ethyl acetate
EtOH: ethanol
Et2O: diethyl ether
g: gram(s)
GABA: gamma-Aminobutyric acid
h: hour(s)
MAO-B: Monoamine oxidase B
MeOH: methanol
MeONa: sodium methoxide
mg: milligram(s)
min: minute(s)
mL: milliliter
mmol: millimole(s)
mol: mole(s)
m.p.: melting point
MTT: 3-(4,5-dimethylthiazol-2-yl)-2,5-diphenyltetrazolium bromide
mTOR: Mammalian target of rapamycin
NE: Norepinephrine
NMDA: N-Methyl-D-aspartic acid
NMR: Nuclear Magnetic Resonance
Pd/C: palladium on charcoal
PI3K: Phosphatidylinositide 3-kinase
PKC: Protein kinase C
PLC: Phospholipase C
PLC-γ1: Isozyme form γ1 of Phospholipase C
rt: room temperature
TBAF: tetrabutylammonium fluoride
TBSCI: tert-butyl-dimethylsilyl chloride
TFA: trifluoroacetic acid
THF: tetrahydrofuran
SDS: Sodium dodecyl sulphate
TBS: TRIS buffered saline
TRIS: tris(hydroxymethyl)aminomethane
Trk-B: Tropomyosin receptor kinase B The term "alkyl" as employed herein alone or as part of another group designates both straight- and branched-chain saturated hydrocarbons containing 1 to 20 carbons, preferably 1 to 10 carbons, and more preferably 1 to 8 carbons. Examples of alkyl groups are methyl, ethyl, n-propyl, isopropyl, n-butyl, isobutyl, tert-butyl, pentyl, hexyl, isohexyl, heptyl, 4,4-dimethylpentyl, octyl, 2,2,4-trimethylpentyl, nonyl, decyl, undecyl, dodecyl, and the various branched-chain isomers thereof.

The term "alkylene" as employed herein alone or as part of another group refers to a divalent radical of an alkyl group as described above, containing 1 to 20 carbons, preferably 1 to 10 carbons, and more preferably 1 to 8 carbons. Examples of alkylene groups are methylene, ethylene, trimethylene, tetramethylene, pentamethylene, hexamethylene, heptamethylene, octamethylene, and the various branched-chain isomers thereof.

The term "alkenyl" as employed herein alone or as part of another group includes both straight- and branched-chain hydrocarbons containing 2 to 20 carbons, preferably 2 to 12 carbons, and more preferably 2 to 8 carbons, and includes 1 to 6 double bonds. Examples of alkenyl groups are vinyl, 2-propenyl, 2-butenyl, 3-butenyl, 3-pentenyl, 4-pentenyl, 2-hexenyl, 3-hexenyl, 2-heptenyl, 4-heptenyl, 3-octenyl, 3-nonenyl, 4-decenyl, 3-undecenyl, and 4,8,12-tetradecatrienyl.

The term "alkenylene" as employed herein alone or as part of another group refers to a divalent radical of an alkenyl group as described above, containing 2 to 20 carbons, preferably 2 to 12 carbons, and more preferably 2 to 8 carbons. Examples of alkenylene groups are vinylene, 2-propenylene, 2-butenylene, 3-butenylene, 3-pentenylene, 4-pentenylene, 2-hexenylene, 3-hexenylene, 2-heptenylene, 4-heptenylene, 3-octenylene.

The term "alkynyl" as employed herein alone or as part of another group includes both straight- and branched-chain hydrocarbons containing from 2 to carbons, preferably 2 to 12 carbons, and more preferably 2 to 8 carbons, and includes 1 to 6 triple bonds and optionally 1 to 3 double bonds. Examples of alkynyl groups are 2-propynyl, 3-butynyl, 4-pentynyl, 2-hexynyl, 4-heptynyl, 3-octynyl, 3-nonynyl, 4-decynyl, 3-undecynyl and 4-dodecynyl.

The term "alkinylene" as employed herein alone or as part of another group refers to a divalent radical of an alkinyl group as described above, containing 2 to 20 carbons, preferably 2 to 12 carbons, and more preferably 2 to 8 carbons. Examples of alkinylene groups are 2-propynylene, 3-butynylene, 4-pentynylene, 2-hexynylene, 4-heptynylene, 3-octynylene, 3-nonynylene, 4-decynylene, 3-undecynylene and 4-dodecynylene.

The term "alkanoyl" or "acyl" as indistinctively used herein alone or as part of another group refers to an alkyl group attached to a carbonyl group. In the context of the present invention, the terms "alkanoyl" and "acyl" have the same meaning. Thus, a $C_n$ alkanoyl or acyl groups is a $C_{n-1}$ alkyl group attached to a carbonyl group. Examples of alkanoyl or acyl groups are acetyl, propionyl and butyroyl.

The term "alkoxy" as employed herein alone or as part of another group designates an alkyl group containing 1 to 20 carbons, preferably 1 to 10 carbons, and more preferably 1 to 8 carbons linked to an oxygen atom. Examples of alkoxy groups are methoxy, ethoxy, n-propoxy, isopropoxy, n-butoxy, isobutoxy, tert-butoxy, pentoxy, hexyloxy, isohexyloxy, heptyloxy, 4,4-dimethylpentoxy, octyloxy, 2,2,4-trimethylpentoxy, nonyloxy, decyloxyl, undecyloxy, dodecyloxy, and the various branched-chain isomers thereof.

The term "cycloalkyl" as employed herein alone or as part of another group includes saturated cyclic hydrocarbon groups containing 1 to 3 rings, including monocyclic alkyl, bicyclic alkyl and tricyclic alkyl systems and containing a total of 3 to 20 carbon atoms, preferably 3 to 10 carbons, forming part of the ring system. Examples of cycloalkyl groups are cyclopropyl, cyclobutyl, cyclopentyl, cyclohexyl, cycloheptyl, cyclooctyl, cyclodecyl, cyclododecyl, adamantyl and bicyclo[3.3.3]undecanyl.

The term "cycloalkenyl" as employed herein alone or as part of another group includes partially unsaturated cyclic hydrocarbon groups containing 1 or 2 double bonds and having 1 to 3 rings, including monocyclic alkyl, bicyclic alkyl and tricyclic alkyl systems, containing a total of 4 to 12 carbons, preferably 5 to carbons, as part of the ring system. Examples of cycloalkenyl groups include, but are not limited to, cyclobutenyl, cyclopentenyl, cyclohexenyl, cycloheptenyl, cyclooctenyl, cyclohexanediyl and cycloheptanediyl.

The term "aryl" as employed herein alone or as part of another group refers to monocyclic or bicyclic aromatic groups containing 6 to 10 carbons in the ring portion, such as phenyl or naphthyl (including 1-naphthyl and 2-naphthyl), and may optionally include 1 to 3 additional fused carbocyclic rings, such as cycloalkyl. Examples of aryl groups are phenyl, 1-naphthyl, 2-naphthyl and tetrahydronaphthyl.

The terms "arylalkyl", "arylalkenyl" and "arylalkynyl" as used alone or as part of another group refer to alkyl, alkenyl, or alkynyl groups as described above having an aryl substituent. Examples of arylalkyl groups are benzyl and phenethyl.

The term "halogen" as used herein alone or as part of another group refers to chlorine, bromine, fluorine and iodine.

The term "heterocyclyl" as employed herein alone or as part of another group refers to a 5-, 6-, or 7-membered saturated or partially unsaturated ring which includes 1 to 2 heteroatoms, selected from the group consisting of nitrogen, oxygen and/or sulfur, and such rings optionally fused to an aryl, cycloalkyl, heteroaryl or heterocyclyl ring. The heterocyclyl group is linked through a carbon atom or a heteroatom.

The term "heteroaryl" as employed herein alone or as part of another group refers to a 5- or 6-membered aromatic ring which includes 1, 2, 3 or 4 heteroatoms, selected from the groups consisting of nitrogen, oxygen or sulfur, and such rings optionally fused to an aryl, cycloalkyl, heteroaryl or heterocyclyl ring. When an heteroaryl group is fused to and aryl it is called a "bicyclic heteroaryl".

The term "heterocyclylalkyl" as employed herein alone or as part of another group refers to a heterocyclyl group as defined above linked through a C atom or heteroatom to an alkyl group as defined above.

The term "heteroarylalkenyl" as employed herein alone or as part of another group refers to a heteroaryl group as defined above linked through a C atom or heteroatom to an alkenyl group as defined above.

The term "heteroarylalkyl" as employed herein alone or as part of another group refers to a heteroaryl group as defined above linked through a C atom or heteroatom to an alkyl group as defined above.

The term "glycosyl" as employed herein refers to 1-O-β-D-galactopyranosyl (galactose), 1-O-β-D-glucopyranosyl (glucose) and 1-O-α-D-glucopyranosyl-α-D-glucopyranosyl (trehalose).

In the context of the present invention, when a group is said to be substituted by one or more substituents it is to be understood that one or more hydrogen atoms in said group are replaced by said one or more substituents.

Where the compounds of formula (I) are in acid form they may form a pharmaceutically acceptable salt such as hydrochloride, L-ascorbate, ferulate, caffeate, valproate, lipoate, tartrate, etc.

As used herein, the term "pharmaceutically acceptable salt" embraces salts with a pharmaceutically acceptable acid or base. Pharmaceutically acceptable acids include both inorganic acids, for example hydrochloric, sulfuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulfonic, ethanesulfonic, benzenesulfonic, ferulic, caffeic, valproic, lipoic or p-toluenesulfonic acid. Pharmaceutical acceptable bases include alkali metal (e.g., sodium or potassium) and alkali earth metal (e.g. calcium or magnesium) hydroxides and organic bases, such as alkyl amines, arylalkyl amines and heterocyclic amines.

All stereoisomers of the compounds of this invention are contemplated either alone or as mixtures thereof. The process of preparation can utilize racemates, enantiomers, or diastereomers as starting materials. When diastereomeric or enantiomeric products are prepared, they can be separated by conventional methods, for example chromatographic or functional crystallization.

The term treatment is used to designate the administration of a pharmaceutically active compound or a composition thereof to control disease progression before or after the clinical signs have appeared. By control of the disease progression it is meant to designate beneficial or desired clinical results including, but not limited to, reduction of symptoms, reduction of the length of the disease, stabilization of the pathological state (specifically avoidance of further deterioration), delay in the disease progression, improvement of the pathological state and remission (both partial and total). Control of disease progression can also entail prolonged survival, compared to the expected survival if the treatment is not applied. In a particular embodiment of the invention, the compounds and compositions of the invention may be used to control the disease progression once at least one of the clinical signs of the disease has appeared.

As a consequence of their pharmacological properties, the compounds of formula (I) may be used to promote neuroplasticity in the context of nervous system diseases and developmental, behavioral and mental disorders where cognitive deficits—particularly in learning and memory—are associated with illness.

Thus, in an aspect of the present invention the compounds of formula (I) are useful as a medicament.

In an embodiment of the present invention the compounds of formula (I) are useful in the treatment of a condition selected from the group consisting of neuropathic pain, fibromyalgia, epilepsy and stroke.

In another embodiment of the present invention the compounds of formula (I) are useful in the treatment of nervous system diseases and/or the treatment of developmental, behavioral and/or mental disorders associated with cognitive deficits.

In another embodiment of the present invention the compounds of formula (I) are useful in the treatment of nervous system diseases and/or developmental, behavioral and/or mental disorders which are associated with learning deficits or with memory deficits.

In another embodiment of the present invention the compounds of formula (I) are useful in the treatment of developmental disorders associated with cognitive deficits selected from the group consisting of Down syndrome, Angelman syndrome, Rett syndrome, autistic disorders, fragile X disorder and Asperger syndrome In another embodiment of the present invention the compounds of formula (I) are useful in the treatment of behavioral and/or mental disorders associated with cognitive deficits selected from the group consisting of depression, bipolar disorder, schizophrenia, cerebral dementias, post traumatic stress disorders, Pick's disease and sleep disorders.

In another embodiment of the present invention the compounds of formula (I) are useful in the treatment of neurodegenerative disorders associated with cognitive deficits selected from the group consisting of Alzheimer's disease, Parkinson's disease, Huntington's disease, amyotrophic lateral sclerosis, fronto temporal dementia and Friedrich's ataxia.

The use of compounds of formula (I) together or in combination with other drugs may prove to be effective in the enhancement of memory consolidation and learning and in the treatment of CNS diseases and/or mental disorders associated with cognitive deficits. Where desired, the compounds of formula (I) may be used in combination with one or more other therapeutic agents which may be administered orally in the same dosage form, in a separate oral dosage form, or by injection.

Combination therapy includes the use of two or more compounds of the invention and the use of one compound of the invention in combination with other drugs selected from the group consisting of acetylcholinesterase inhibitors such as rivastigmine, donepezil, galantamine and huperzine A; NMDA antagonists such as memantine and latrepirdine; histamine $H_3$ receptor antagonists such as pitolisant, SAR-110894, ABT-288, S-38093 and AZD-5213; beta-secretase 1 (BACE1) inhibitors such as resveratrol, HPP-854, LY-2886721, E-2609 and MK-8931; antiamyloidogenic agents such as (−)-epigallocatechin gallate, (+)-phenserine and AAD-2004; 5-$HT_6$ receptor antagonists such as Lu-AE-58054, AVN-322, GSK-215083, GSK-742457; 5-$HT_4$ receptor agonists such as SL-65.0102 and BIMU-1; MAOB inhibitors such as rasagiline, ladostigil and RG-1577; GABA(A) receptor modulators such as etazolate and RG-1662; muscarinic $M_1$ receptor agonists such as sabcomeline and MCD-386; and gamma-secretase inhibitors such as pinitol.

Drugs of the present invention may be administered orally, parenterally, subcutaneously, rectally, topically, by inhalation and locally. Any administration method commonly used for drugs, such as tablets, coated tablets, capsules, solution (including nanoemulsion), syrup, powder, suppository, cream and ointment, may be used. The pharmaceutical composition can be formulated employing conventional liquid or solid vehicles or diluents and pharmaceutical additives according to the desired mode of administration.

EXAMPLES

The following examples represent specific embodiments of the present invention.

Example 1

1-[2-[4-(2-Hydroxyethyl)phenoxy]ethyl]pyrrolidin-2-one

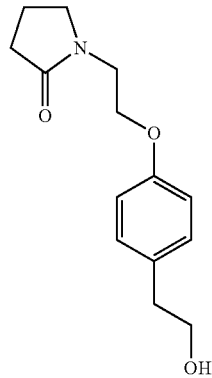 [SMILES: O=C1CCCN1CCOc1ccc(CCO)cc1]

2-[4-(Benzyloxy)phenyl]ethanol

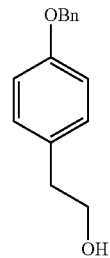 [SMILES: OCCc1ccc(OCc2ccccc2)cc1]

4-(2-Hydroxyethyl)phenol (7.0 g, 50.7 mmol) was dissolved in acetone (75 mL) and cooled to 0° C. Potassium carbonate (9.1 g, 65.9 mmol) was added portionwise and the resulting white suspension was vigorously stirred for 10 min at room temperature and cooled again to 0° C. Benzyl bromide was added dropwise (7.2 mL, 60.8 mmol) and the reaction mixture was refluxed for 22 h. The suspension was then cooled to room temperature, filtered and evaporated to dryness. The resulting white solid was dissolved in Et$_2$O and successively washed with 2% aqueous solution of NaOH (3×), brine (3×), dried over anhydrous MgSO$_4$ and evaporated to dryness to afford 11.4 g of a white solid which was used in the following step without further purification.

[4-(Benzyloxy)phenethoxy](tert-butyl)dimethylsilane

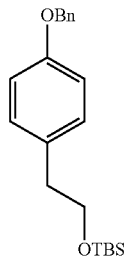 [SMILES: CC(C)(C)[Si](C)(C)OCCc1ccc(OCc2ccccc2)cc1]

2-[4-(Benzyloxy)phenyl]ethanol (11.4 g, 50.7 mmol) was dissolved in 100 mL of DCM and cooled to 0° C. Imidazole (4.2 g, 61.2 mmol) and TBSCI (8.5 g, 56.0 mmol) were successively added portionwise and the resulting white suspension was warmed to room temperature and stirred for 21 h. Then, the reaction was quenched with MeOH (15 mL), vigorously stirred for 5 min and evaporated to dryness under vacuum. The resulting white solid was dissolved with EtOAc (5×) and the resulting organic phase was successively washed with sat. aq. solution of NH$_4$Cl (3×), 10% aq. NaHCO$_3$ (3×) and brine (2×). The organic layer was dried over anhydrous MgSO$_4$ and evaporated to dryness under vacuum to afford 17.1 g of a white solid which was used in the next step without further purification.

4-[2-(tert-Butyldimethylsilyloxy)ethyl]phenol

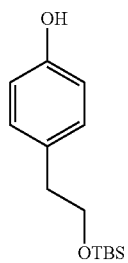 [SMILES: CC(C)(C)[Si](C)(C)OCCc1ccc(O)cc1]

[4-(Benzyloxy)phenethoxy](tert-butyl)dimethylsilane (17.1 g, 50.0 mmol) was dissolved in EtOAc (120 mL) in a pressure reactor and Pd/C (1.7 g) was added. The black suspension was vigorously stirred under a hydrogen atmosphere (5.5 bar) at room temperature for 4 h and more H$_2$ was introduced to reach the initial pressure. After additional 20 h, the operation was repeated. Finally, after 46 h of reaction, the reaction mixture was filtered through a Celite pad and evaporated to dryness under vacuum to afford 11.4 g (45.1 mmol, 89% yield for the last three steps) of a white solid identified by $^1$H-NMR as 4-[2-(tert-butyldimethylsilyloxy)ethyl]phenol which was used in the following step without further purification.

$^1$H NMR (400 MHz, CDCl$_3$) δ 7.07 (ddd, J=8.8, 2.8, 2.0 Hz, 2H), 6.75 (ddd, J=8.8, 2.8, 2.2 Hz, 2H), 3.76 (t, J=7.1 Hz, 2H), 2.75 (t, J=7.1 Hz, 2H).

1-[2-[4-(2-Hydroxyethyl)phenoxy]ethyl]pyrrolidin-2-one

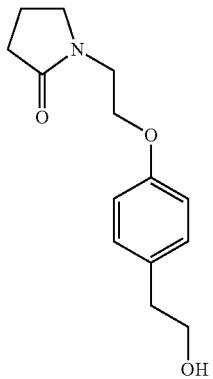 [SMILES: O=C1CCCN1CCOc1ccc(CCO)cc1]

Triphenylphosphine (0.75 g, 2.85 mmol), 4-[2-(tert-butyldimethylsilyl-oxy) ethyl]phenol (0.40 g, 1.58 mmol) and 1-(2-hydroxyethyl)pyrrolidin-2-one (215 µL, 1.90 mmol) were dissolved in toluene (20 mL) at room temperature. A solution of DEAD (~40% in toluene, 1.3 mL, 2.9 mmol) was added dropwise and the mixture was stirred for 21 h at room temperature. The crude was then diluted with EtOAc, treated with 10% aq. HCl for 1 h and washed with 10% aq. HCl (×3). The combined organic fractions were dried (MgSO$_4$), filtered and evaporated to dryness under vacuum. The resulting syrup was purified by column chromatography (SiO$_2$, from 40% EtOAc in hexane to 100% EtOAc, and to 20% MeOH in EtOAc) to afford 158 mg (0.63 mmol, 40% yield) of a colorless oil identified as 1-[2-[4-(2-hydroxyethyl)phenoxy]ethyl]pyrrolidin-2-one 5 $^1$H NMR (400 MHz, CD$_3$OD) δ 7.14 (ddd, J=8.4, 3.2, 1.8 Hz, 2H), 6.84 (ddd, J=8.4, 3.2, 2.0 Hz, 2H), 4.10 (t, J=5.1 Hz, 2H), 3.83 (t, J=6.5 Hz, 2H), 3.67 (t, J=5.1 Hz, 2H), 3.58 (t, J=7.2 Hz, 2H), 2.81 (t, J=6.5 Hz, 2H), 2.39 (t, J=8.1 Hz, 2H), 2.06-1.97 (m, 2H).

$^{13}$C NMR (101 MHz, CD$_3$OD) δ 175.40, 156.73, 131.10, 129.80, 114.26, 66.23, 63.40, 48.71, 42.21, 38.06, 30.60, 17.90.

Example 2

2-[4-[3-(Methylamino)-1-phenylpropoxy]phenyl]ethanol hydrochloride

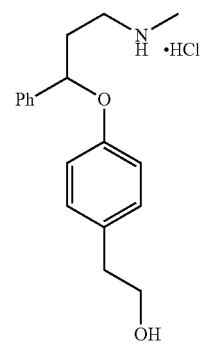

Method A:

3-[4-[2-(tert-Butyldimethylsilyloxy)ethyl]phenoxy]-N-methyl-3-phenylpropan-1-amine

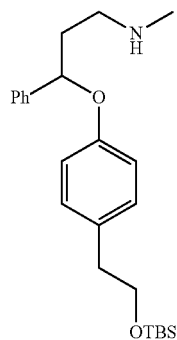

Triphenylphosphine (3.0 g, 11.4 mmol), 4-[2-(tert-butyldimethylsilyloxy)ethyl]phenol (2.40 g, 9.52 mmol) and 3-(methylamino)-1-phenylpropan-1-ol (1.88 g, 11.40 mmol) were dissolved in toluene (55 mL). A solution of DEAD (~40% in toluene, 5.2 mL, 11.4 mmol) was added dropwise at room temperature and the mixture was stirred for 16 h. Then, additional triphenylphosphine (1.5 g, 5.7 mmol) and DEAD (~40% in toluene, 2.6 mL, 5.7 mmol) were consecutively added and the mixture was stirred for additional 8 h. A third addition of triphenylphosphine (0.75 g, 2.9 mmol) and DEAD (~40% in toluene, 1.3 mL, 2.9 mmol) was performed and the mixture was stirred for additional 16 h. The crude was then evaporated to dryness under vacuum and purified by flash chromatography (SiO$_2$, from 100% EtOAc to 25% MeOH in EtOAc) to afford 2.03 g of a pale yellow oil. $^1$H-NMR analysis allowed the identification of 3-[4-[2-(tert-butyldimethylsilyloxy)ethyl]phenoxy]-N-methyl-3-phenylpropan-1-amine despite the presence of some minor impurities.

$^1$H NMR (400 MHz, CD$_3$OD) δ 7.38-7.19 (m, 5H), 6.99 (ddd, J=8.8, 2.8, 2.0 Hz, 2H), 6.77 (ddd, J=8.8, 3.0, 1.8 Hz, 2H), 5.27 (dd, J=8.1, 4.8 Hz, 1H), 3.72 (t, J=7.1 Hz, 2H), 2.79-2.61 (m, 5H), 2.36 (s, 3H), 2.21-2.10 (m, 1H), 2.06-1.95 (m, 1H), 0.82 (s, 9H), −0.10 (s, 3H), −0.12 (s, 3H).

2-[4-[3-(Methylamino)-1-phenylpropoxy]phenyl]ethanol hydrochloride

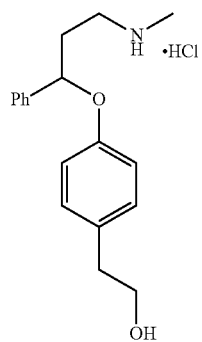 [SMILES: CNCCC(Oc1ccc(CCO)cc1)c1ccccc1 ; Cl]

Not completely pure 3-[4-[2-(tert-butyldimethylsilyloxy)ethyl]phenoxy]-N-methyl-3-phenylpropan-1-amine (2.03 g) was dissolved in EtOH (20 mL), cooled to 0° C. and treated with conc. HCl (1.0 mL, 12.2 mmol) for 80 min. Afterwards, it was evaporated to dryness under vacuum to afford a crude which was purified by flash chromatography (SiO$_2$, from 100% EtOAc to 30% MeOH in EtOAc) to afford 1.40 g (4.35 mmol, 46% yield for the last two steps) of a paste that, once lyophilized, turned into an amorphous off-white solid identified as 2-[4-[3-(methylamino)-1-phenylpropoxy]phenyl]ethanol hydrochloride.

$^1$H NMR (400 MHz, CD$_3$OD) δ 7.43-7.22 (m, 5H), 7.04 (ddd, J=8.8, 2.8, 1.8 Hz, 2H), 6.81 (ddd, J=8.8, 3.0, 2.0 Hz, 2H), 5.39 (dd, J=8.4, 4.1 Hz, 1H), 3.64 (t, J=7.0 Hz, 2H), 3.28-3.14 (m, 2H), 2.72 (s, 3H), 2.69 (t, J=7.0 Hz, 2H), 2.37-2.18 (m, 2H). $^{13}$C NMR (101 MHz, CD$_3$OD) δ 157.21, 141.92, 133.08, 130.80, 129.80, 129.06, 127.11, 117.07, 78.42, 64.24, 47.64, 39.24, 36.00, 33.85.

Method B:

tert-Butyl 3-hydroxy-3-phenylpropyl(methyl)carbamate

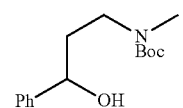

3-(Methylamino)-1-phenylpropan-1-ol (5.0 g, 30.3 mmol) was dissolved in 80 mL of THF and cooled to 0° C. Et$_3$N (5.0 mL, 36.4 mmol) and Boc$_2$O (7.3 g, 33.3 mmol) were successively added and the mixture was stirred at room temperature for 20 h. Then, the reaction mixture was diluted in EtOAc and successively washed with sat. aq. NH$_4$Cl solution (3×) and brine (3×). The organic layer was dried over anhydrous MgSO$_4$ and evaporated to dryness under vacuum to afford 7.9 g (29.78 mmol, 98% yield) of a colorless oil identified by $^1$H-NMR as tert-butyl 3-hydroxy-3-phenylpropyl(methyl)carbamate which was used in the next step without further purification.

Methyl 2-[4-[3-[tert-butoxycarbonyl(methyl)amino]-1-phenylpropoxy]phenyl]acetate

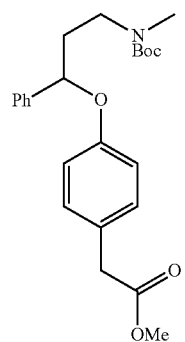

Triphenylphosphine (865 mg, 3.3 mmol), methyl 2-(4-hydroxy-phenyl)acetate (365 mg, 2.2 mmol) and tert-butyl 3-hydroxy-3-phenylpropyl(methyl)carbamate (700 mg, 2.6 mmol) were dissolved in toluene (13 mL). A solution of DEAD (~40% in toluene, 1.5 mL, 3.3 mmol) was added dropwise at room temperature.

The mixture was stirred at 80° C. for 21 h. Then, it was cooled to room temperature, diluted with EtOAc and washed with 10% HCl (3×), dried over anhydrous MgSO$_4$ and concentrated under vacuum. The resulting crude was purified by flash chromatography (SiO$_2$, from 100% hexane to 50% EtOAc in hexane) to afford 640 mg (1.55 mmol, 70% yield) of a colorless oil identified by $^1$H-NMR as methyl 2-[4-[3-[tert-butoxycarbonyl(methyl)amino]-1-phenylpropoxy]phenyl]acetate.

$^1$H NMR (400 MHz, CDCl$_3$) δ 7.35-7.29 (m, 4H), 7.26-7.22 (m, 1H), 7.07 (d, J=8.6 Hz, 2H), 6.77 (d, J=8.6 Hz, 2H), 5.11-5.04 (m, 1H), 3.65 (s, 3H), 3.49 (s, 2H), 3.47-3.30 (m, 2H), 2.84 (s, 3H), 2.19-2.05 (m, 2H), 1.39 (s, 9H).

tert-Butyl 3-[4-(2-hydroxyethyl)phenoxy]-3-phenylpropyl(methyl)carbamate

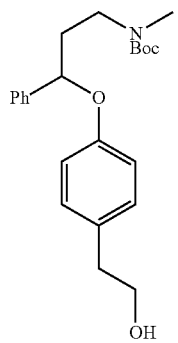 [SMILES: CN(CCC(Oc1ccc(CCO)cc1)c1ccccc1)C(=O)OC(C)(C)C]

Methyl 2-[4-[3-[tert-butoxycarbonyl(methyl)amino]-1-phenylpropoxy]phenyl]acetate (1.08 g, 2.61 mmol) was dissolved in dry THF (30 mL) under nitrogen and cooled to 0° C. Lithium aluminum hydride (500 mg, 13.2 mmol) was added portionwise and the resulting suspension was vigorously stirred at 0° C. for 45 min and at room temperature for 2 h. Then, it was cooled to 0° C. and carefully quenched with ice and 0.5 mL of 10% NaOH solution, diluted with EtOAc and stirred for 20 min at 0° C. The suspension was filtered through a Celite pad and concentrated under vacuum to afford 0.93 g (2.41 mmol, 92% yield) of a colorless oil identified as tert-butyl 3-[4-(2-hydroxyethyl)phenoxy]-3-phenylpropyl(methyl)carbamate that was employed in the next reaction without further purification.

2-[4-[3-(Methylamino)-1-phenylpropoxy]phenyl]ethanol

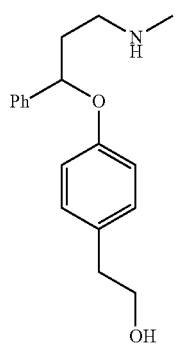 [SMILES: CNCCC(Oc1ccc(CCO)cc1)c1ccccc1]

tert-Butyl 3-[4-(2-hydroxyethyl)phenoxy]-3-phenylpropyl(methyl)carbamate (200 mg, 0.52 mmol) was dissolved in DCM (3 mL) and cooled to 0° C. TFA (385 μL, 5.2 mmol) was added dropwise and the mixture was stirred for 45 min at room temperature. Then, the solution was cooled again and quenched by the dropwise addition of a 5% NaOH aqueous solution. The organic layer was consecutively washed with 5% NaOH (3×) and brine (2×). The combined aqueous layers were extracted with DCM (4×). The combined organic layers were dried over anhydrous MgSO$_4$ and evaporated to dryness under vacuum to furnish 141 mg (0.49 mmol, 95% yield) of 2-[4-[3-(methylamino)-1-phenylpropoxy]phenyl]ethanol as a colorless paste that was used in the next step without further purification.

$^1$H NMR (400 MHz, CDCl$_3$) δ 7.38-7.29 (m, 4H), 7.28-7.22 (m, 1H), 7.03 (ddd, J=8.4, 3.2, 1.6 Hz, 2H), 6.80 (ddd, J=8.4, 3.2, 2.0 Hz, 2H), 5.21 (dd, J=8.4, 4.6 Hz, 1H), 3.78 (t, J=6.5 Hz, 2H), 2.75 (t, J=6.5 Hz, 2H), 2.43 (s, 3H), 2.22-2.12 (m, 1H), 2.04-1.95 (m, 1H).

2-[4-[3-(Methylamino)-1-phenylpropoxy]phenyl]ethanol hydrochloride

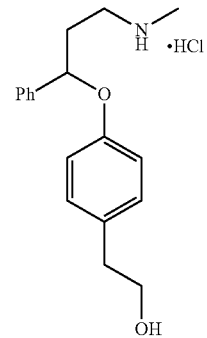

2-[4-[3-(Methylamino)-1-phenylpropoxy]phenyl]ethanol (141 mg, 0.49 mmol) was treated with 4M HCl in dioxane (1 mL) at room temperature for 30 min.

Then, EtOAc was added until the formation of a white solid. The suspension was cooled to 0° C. and filtered. The solid was then digested in refluxing EtOAc for 1 h and filtered again to afford 89 mg (0.28 mmol, 56% yield) of 2-[4-[3-(methylamino)-1-phenylpropoxy]phenyl]ethanol hydrochloride as a white powder (m.p.: 145-147° C.).

Example 3

(R)-2-[4-[3-(Methylamino)-1-phenylpropoxy]phenyl]ethanol hydrochloride

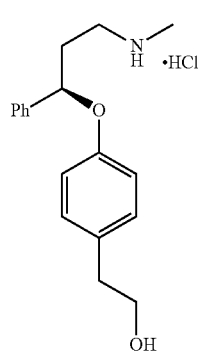 [SMILES: CNCC[C@@H](Oc1ccc(CCO)cc1)c1ccccc1 ; Cl]

(S)-3-Iodo-1-phenylpropan-1-ol [Robertson, D. W. et al. *J. Med. Chem.* 1988, 31 (7), 1412-1417]

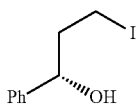

(S)-3-Chloro-1-phenylpropan-1-ol (2.2 g, 12.9 mmol) was dissolved in a saturated solution of NaI in acetone (150 mL) and refluxed for 17 h. Once cooled to room temperature, it was filtered and concentrated under vacuum. The residue was dissolved in EtOAc and washed with brine (×3), dried over anhydrous MgSO₄ and evaporated to dryness under vacuum to afford 3.2 g of an orange solid that was used in the following step without further purification.

(S)-3-(Methylamino)-1-phenylpropan-1-ol [Robertson, D. W. et al. *J. Med. Chem.* 1988, 31 (7), 1412-1417]]

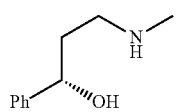

(S)-3-Iodo-1-phenylpropan-1-ol (3.2 g) was dissolved in THF (5 mL) and treated with a 40% solution of methylamine in water (11 mL, 129 mmol). The reaction mixture was stirred for 22 h and concentrated under vacuum. The residue was partitioned between EtOAc and a (4:1) mixture of brine and 10% NaOH. The organic layer was washed with brine (2×) and dried over anhydrous MgSO₄. Removal of the solvent under reduced pressure afforded 1.84 g (11.1 mmol, 86% yield for the last two steps) of a yellow oil that was used in the following reaction without further purification.

(S)-tert-Butyl 3-hydroxy-3-phenylpropyl(methyl)carbamate

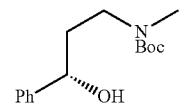

(S)-3-(Methylamino)-1-phenylpropan-1-ol (1.84 g, 11.1 mmol) was dissolved in 40 mL of THF and cooled to 0° C. Et₃N (2.2 mL, 15.5 mmol) and Boc₂O (2.67 g, 12.3 mmol) were successively added and the mixture was stirred at room temperature for 22 h. Then, the reaction mixture was diluted in EtOAc and successively washed with sat. aq. NH₄Cl solution (3×) and brine (3×). The organic layer was then dried over anhydrous MgSO₄ and evaporated to dryness to afford 2.86 g (10.8 mmol, 97% yield) of a colorless oil identified by ¹H-NMR as (S)-tert-butyl 3-hydroxy-3-phenylpropyl(methyl)carbamate which was used in the next step without further purification.

(R)-Methyl 2-[4-[3-[tert-butoxycarbonyl(methyl)amino]-1-phenylpropoxy]phenyl]acetate

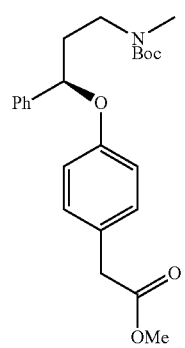 [SMILES: COC(=O)Cc1ccc(O[C@H](CCN(C)C(=O)OC(C)(C)C)c2ccccc2)cc1]

Triphenylphosphine (750 mg, 2.84 mmol), methyl 2-(4-hydroxy-phenyl)acetate (273 mg, 1.64 mmol) and (S)-tert-butyl 3-hydroxy-3-phenylpropyl(methyl) carbamate (522 mg, 1.97 mmol) were dissolved in toluene (8 mL). A solution of DEAD (~40% in toluene, 1.3 mL, 2.84 mmol) was added dropwise at room temperature. The mixture was stirred at 80° C. for 21 h. Then, it was cooled to room temperature, diluted with EtOAc and washed with 10% HCl (3×), dried over anhydrous MgSO₄ and concentrated under vacuum. The resulting crude was purified by flash chromatography (SiO₂, from 100% hexane to 50% EtOAc in hexane) to afford 460 mg (1.11 mmol, 68% yield) of a colorless oil identified by ¹H-NMR as methyl (R)-2-[4-[3-[tert-butoxycarbonyl(methyl)amino]-1-phenylpropoxy]phenyl]acetate.

35
(R)-tert-Butyl 3-[4-(2-hydroxyethyl)phenoxy]-3-phenylpropyl(methyl)carbamate

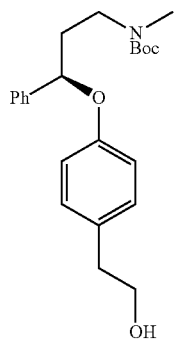 [SMILES: CN(CC[C@@H](Oc1ccc(CCO)cc1)c1ccccc1)C(=O)OC(C)(C)C]

Methyl (R)-2-[4-[3-[tert-butoxycarbonyl(methyl)amino]-1-phenylpropoxy]phenyl]acetate (2.01 g, 4.86 mmol) was dissolved in dry THF (60 mL) under nitrogen and cooled to 0° C. Lithium aluminum hydride (555 mg, 14.6 mmol) was added portionwise and the resulting suspension was vigorously stirred at 0° C. for 30 min and at room temperature for 3 h. Then, it was cooled to 0° C. and carefully quenched with ice and 0.5 mL of 10% NaOH solution, diluted with EtOAc and stirred for 20 min at 0° C. in the presence of anhydrous $MgSO_4$. The suspension was filtered through a Celite pad and concentrated under vacuum to afford 1.75 g (4.54 mmol, 93% yield) of colorless oil that was employed in the next reaction without further purification.

(R)-2-[4-[3-(Methylamino)-1-phenylpropoxy]phenyl]ethanol

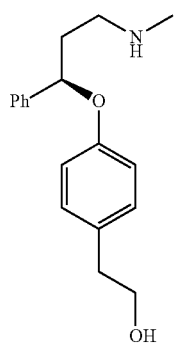 [SMILES: CNCC[C@@H](Oc1ccc(CCO)cc1)c1ccccc1]

(R)-tert-Butyl 3-[4-(2-hydroxyethyl)phenoxy]-3-phenylpropyl(methyl)carbamate (1.75 g, 4.54 mmol) was dissolved in dichloromethane (35 mL) and cooled to 0° C. TFA (3.36 mL, 45.4 mmol) was added dropwise and the mixture was stirred for 60 min at room temperature. Then, the solution was cooled again and quenched by the dropwise addition of a 5% NaOH aqueous solution. The organic layer was consecutively washed with 5% NaOH (3×) and brine (2×). The combined aqueous layers were extracted with dichloromethane (6×). The combined organic layers were dried over anhydrous $MgSO_4$ and evaporated to dryness to furnish 1.28 g (4.49 mmol, 98% yield) of a colorless paste that was used in the next step without further purification.

36
(R)-2-[4-[3-(Methylamino)-1-phenylpropoxy]phenyl]ethanol hydrochloride

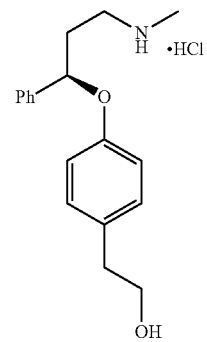 [SMILES: CNCC[C@@H](Oc1ccc(CCO)cc1)c1ccccc1 ; Cl]

(R)-2-[4-[3-(Methylamino)-1-phenylpropoxy]phenyl]ethanol (1.28 g, 4.49 mmol) was treated with 4M HCl in dioxane (3.4 mL) at room temperature for 15 min. The resulting suspension was filtered and washed with EtOAc. The solid was digested in refluxing EtOAc for 1 h and filtered again to afford 790 mg (2.45 mmol, 56% yield) of (R)-2-[4-[3-(methylamino)-1-phenylpropoxy]phenyl]ethanol hydrochloride as a white powder.

Example 4

(S)-2-[4-[3-(Methylamino)-1-phenylpropoxy]phenyl]ethanol hydrochloride

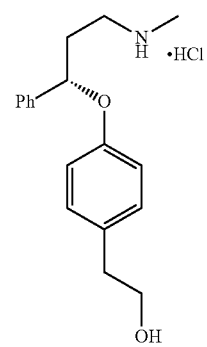

(R)-3-Iodo-1-phenylpropan-1-ol [Robertson, D. W. et al. *J. Med. Chem.* 1988, 31 (7), 1412-1417]

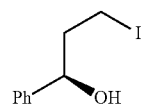

(R)-3-Iodo-1-phenylpropan-1-ol was prepared following the same procedure described for (S)-3-iodo-1-phenylpropan-1-ol (see Example 3).

37

(R)-3-(Methylamino)-1-phenylpropan-1-ol [Robertson, D. W. et al. *J. Med. Chem.* 1988, 31 (7), 1412-1417]

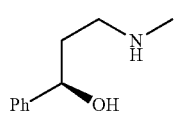

(R)-3-(Methylamino)-1-phenylpropan-1-ol was prepared following the same procedure described for (S)-3-(methylamino)-1-phenylpropan-1-ol (see Example 3).

(R)-tert-Butyl 3-hydroxy-3-phenylpropyl(methyl)carbamate

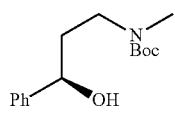 [SMILES: CN(CC[C@@H](O)c1ccccc1)C(=O)OC(C)(C)C]

(R)-tert-Butyl 3-hydroxy-3-phenylpropyl(methyl)carbamate was prepared following the same procedure described for (S)-tert-butyl 3-hydroxy-3-phenylpropyl(methyl)carbamate (see Example 3).

(S)-Methyl 2-[4-[3-[tert-butoxycarbonyl(methyl)amino]-1-phenylpropoxy]phenyl]acetate

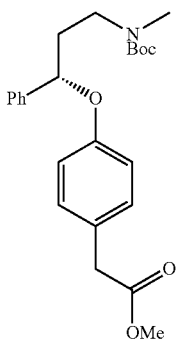 [SMILES: COC(=O)Cc1ccc(O[C@@H](CCN(C)C(=O)OC(C)(C)C)c2ccccc2)cc1]

(S)-Methyl 2-[4-[3-[tert-butoxycarbonyl(methyl)amino]-1-phenylpropoxy]phenyl]acetate was prepared following the same procedure described for (R)-Methyl 2-5 [4-[3-[tert-butoxycarbonyl(methyl)amino]-1-phenylpropoxy]phenyl]acetate (see Example 3).

38

(S)-tert-Butyl 3-[4-(2-hydroxyethyl)phenoxy]-3-phenylpropyl(methyl)carbamate

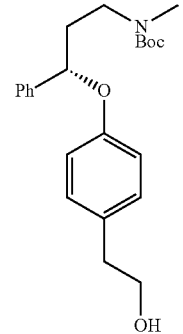

(S)-tert-Butyl 3-[4-(2-hydroxyethyl)phenoxy]-3-phenylpropyl(methyl)carbamate was prepared following the same procedure described for (R)-tert-butyl 3-[4-(2-hydroxyethyl)phenoxy]-3-phenylpropyl(methyl)carbamate (See Example 3).

(S)-2-[4-[3-(Methylamino)-1-phenylpropoxy]phenyl]ethanol

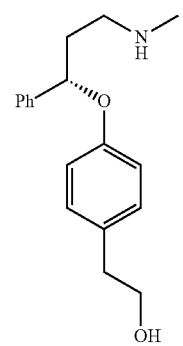

(S)-2-[4-[3-(Methylamino)-1-phenylpropoxy]phenyl]ethanol was prepared following the same procedure described for (R)-2-[4-[3-(methylamino)-1-phenylpropoxy]phenyl]ethanol (see Example 3).

(S)-2-[4-[3-(Methylamino)-1-phenylpropoxy]phenyl]ethanol hydrochloride

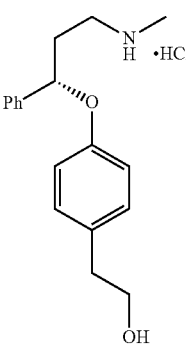

(S)-2-[4-[3-(Methylamino)-1-phenylpropoxy]phenyl] ethanol (190 mg, 0.67 mmol) was dissolved in Et$_2$O (0.5 mL), cooled to 0° C. and treated with 4M HCl in dioxane (0.8 mL). The mixture was stirred at room temperature for 1 h and concentrated under vacuum. The resulting residue was purified by flash chromatography (SiO$_2$, from 100% EtOAc to 30% MeOH in EtOAc) to afford 130 mg (0.40 mmol, 61% yield) of a paste that, once lyophilized, turned into an amorphous off-white solid identified as (S)-2-[4-[3-(methylamino)-1-phenylpropoxy]phenyl]ethanol hydrochloride.

Example 5

2-[4-[3-Methylamino)-1-phenylpropoxy]phenyl] ethanol L-ascorbic acid salt

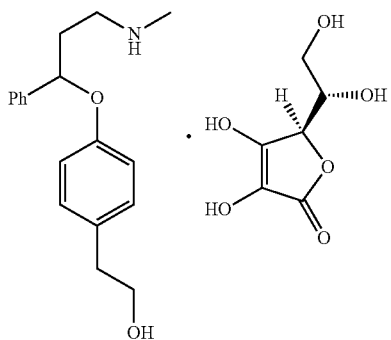 [SMILES: CNCCC(Oc1ccc(CCO)cc1)c1ccccc1 ; O=C1O[C@H]([C@@H](O)CO)C(O)=C1O]

2-[4-[3-(Methylamino)-1-phenylpropoxy]phenyl]ethanol (77 mg, 0.27 mmol) was dissolved in MeOH (2 mL), cooled to 0° C. and L-ascorbic acid (48 mg, 0.27 mmol) was added. The solution was stirred at room temperature for 4 h and evaporated to dryness to afford 125 mg (0.27 mmol, 100% yield) of 2-[4-[3-(methylamino)-1-phenylpropoxy]phenyl] ethanol L-ascorbic acid salt as an off-white solid (m.p.: 134-137° C.).

$^1$H NMR (400 MHz, CD$_3$OD) δ 7.43-7.22 (m, 5H), 7.04 (ddd, J=8.8, 2.8, 1.8 Hz, 2H), 6.81 (ddd, J=8.8, 3.0, 2.0 Hz, 2H), 5.39 (dd, J=8.4, 4.1 Hz, 1H), 4.41 (d, J=2.9 Hz, 1H), 3.89 (td, J=6.6, 2.9 Hz, 1H), 3.72-3.61 (m, 4H), 3.35 (s, 2H), 3.28-3.14 (m, 2H), 2.72 (s, 3H), 2.69 (t, J=7.0 Hz, 2H), 2.37-2.18 (m, 2H).

Example 6

2-[4-[3-(Methylamino)-1-phenylpropoxy]phenyl] ethanol ferulic acid salt

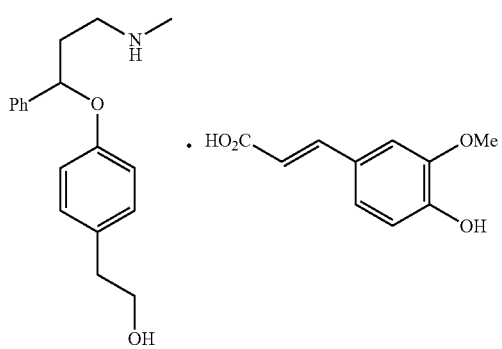 [SMILES: CNCCC(Oc1ccc(CCO)cc1)c1ccccc1 ; COc1cc(/C=C/C(=O)O)ccc1O]

2-[4-[3-(Methylamino)-1-phenylpropoxy]phenyl]ethanol ferulic acid salt was obtained as a white solid (m.p.: 100-104° C.) following the same procedure described for Example 5.

$^1$H NMR (400 MHz, CD$_3$OD) δ 7.40-7.21 (m, 6H), 7.10 (s, 1H), 7.04-6.95 (m, 3H), 6.80-6.75 (m, 3H), 6.34 (d, J=15.9 Hz, 1H), 5.36-5.30 (m, 1H), 3.86 (s, 3H), 3.65-3.58 (m, 2H), 3.20-3.05 (m, 2H), 2.72-2.65 (m, 5H), 2.34-2.13 (m, 2H).

Example 7

2-[4-[3-(Methylamino)-1-phenylpropoxy]phenyl] ethanol caffeic acid salt

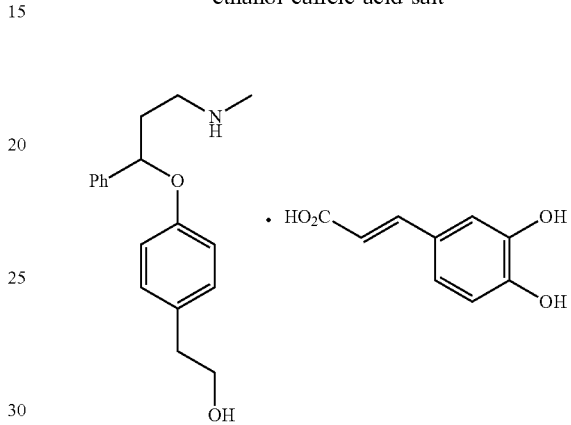

2-[4-[3-(Methylamino)-1-phenylpropoxy]phenyl]ethanol caffeic acid salt was obtained as a white solid (m.p.: 120-122° C.) following the same procedure described for Example 5.

$^1$H NMR (400 MHz, CD$_3$OD) δ 7.37-7.25 (m, 6H), 7.04 (ddd, J=8.8, 2.8, 1.8 Hz, 2H), 6.99 (d, J=2.0 Hz, 1H), 6.86 (dd, J=8.1, 2.0 Hz, 1H), 6.80 (ddd, J=8.8, 3.0, 2.0 Hz, 2H), 6.74 (d, J=8.1 Hz, 1H), 6.27 (d, J=15.9 Hz, 1H), 5.39 (dd, J=8.4, 4.1 Hz, 1H), 3.64 (t, J=7.0 Hz, 2H), 3.28-3.14 (m, 2H), 2.72 (s, 3H), 2.69 (t, J=7.0 Hz, 2H), 2.37-2.18 (m, 2H).

Example 8

2-[4-[3-(Methylamino)-1-phenylpropoxy]phenyl] ethanol valproic acid salt

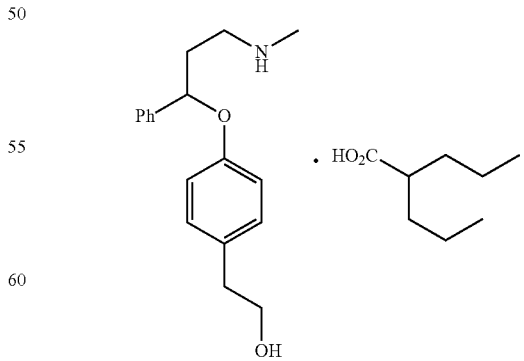

2-[4-[3-(Methylamino)-1-phenylpropoxy]phenyl]ethanol valproic acid salt was obtained as a colorless oil following the same procedure described for Example 5.

¹H NMR (400 MHz, CD₃OD) δ 7.42-7.22 (m, 5H), 7.04 (ddd, J=8.8, 2.8, 1.8 Hz, 2H), 6.81 (ddd, J=8.8, 3.0, 2.0 Hz, 2H), 5.35 (dd, J=8.4, 4.2 Hz, 1H), 3.65 (t, J=7.0 2H), 3.26-3.11 (m, 2H), 2.74-2.61 (m, 5H), 2.35-2.13 (m, 3H), 1.61-1.48 (m, 2H), 1.43-1.24 (m, 6H), 0.92-0.87 (m, 6H).

Example 9

2-[4-[3-(Methylamino)-1-phenylpropoxy]phenyl] ethanol (R)-lipoic acid salt

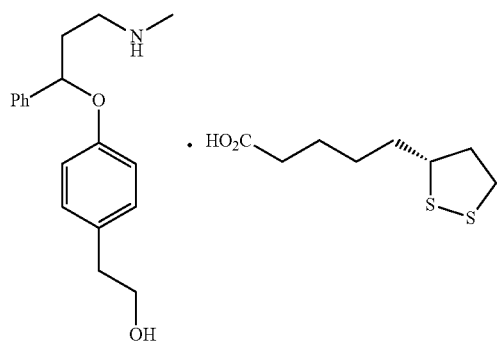 [SMILES: CNCCC(Oc1ccc(CCO)cc1)c1ccccc1 ; O=C(O)CCCC[C@@H]1CCSS1]

2-[4-[3-(Methylamino)-1-phenylpropoxy]phenyl]ethanol (R)-lipoic acid salt was obtained as a colorless oil following the same procedure described for Example 5.

¹H NMR (400 MHz, CD₃OD) δ 7.43-7.24 (m, 5H), 7.04 (ddd, J=8.8, 2.8, 1.8 Hz, 2H), 6.81 (ddd, J=8.8, 3.0, 2.0 Hz, 2H), 5.37 (dd, J=8.4, 4.1 Hz, 1H), 3.65 (t, J=7.1 Hz, 2H), 3.60-3.52 (m, 1H), 3.26-3.04 (m, 4H), 2.71-2.65 (m, 5H), 2.49-2.39 (m, 1H), 2.36-2.25 (m, 1H), 2.25-2.16 (m, 3H), 1.93-1.82 (m, 1H), 1.76-1.55 (m, 4H), 1.51-1.39 (m, 2H).

Example 10

4-[3-(Methylamino)-1-phenylpropoxy]phenethyl acetate hydrochloride

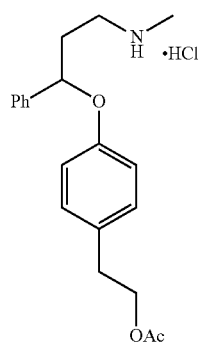 [SMILES: CNCCC(Oc1ccc(CCOC(C)=O)cc1)c1ccccc1 ; Cl]

4-[3-[tert-Butoxycarbonyl(methyl)amino]-1-phenylpropoxy]phenethyl acetate

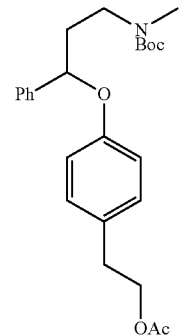 [SMILES: CC(=O)OCCc1ccc(OC(CCN(C)C(=O)OC(C)(C)C)c2ccccc2)cc1]

tert-Butyl 3-[4-(2-hydroxyethyl)phenoxy]-3-phenylpropyl(methyl)carbamate (262 mg, 0.68 mmol) was dissolved in 5 mL of DCM and cooled to 0° C. Et₃N (141 μL, 1.02 mmol) and Ac₂O (77 μL, 0.82 mmol) were successively added and the mixture was stirred at room temperature for 19 h. Then, the reaction mixture was diluted in EtOAc and successively washed with sat. aq. NH₄Cl solution (3×) and brine (3×). The organic layer was then dried over anhydrous MgSO₄ and evaporated to dryness under vacuum to afford 281 mg (0.66 mmol, 97% yield) of a colorless oil identified by ¹H-NMR as 4-[3-[tert-butoxycarbonyl(methyl)amino]-1-phenylpropoxy]phenethyl acetate which was used in the next step without further purification.

4-[3-(Methylamino)-1-phenylpropoxy]phenethyl acetate

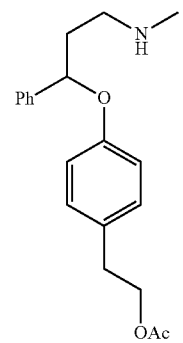

4-[3-(Methylamino)-1-phenylpropoxy]phenethyl acetate was prepared in a 85% yield following the same procedure described for 2-[4-[3-(methylamino)-1-phenylpropoxy]phenyl]ethanol (see Example 2).

4-[3-(Methylamino)-1-phenylpropoxy]phenethyl acetate hydrochloride

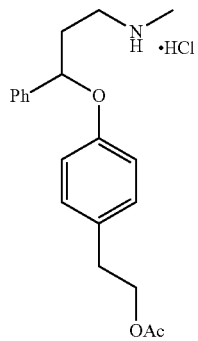 [SMILES: CNCCC(Oc1ccc(CCOC(C)=O)cc1)c1ccccc1 ; Cl]

4-[3-(Methylamino)-1-phenylpropoxy]phenethyl acetate (182 mg, 0.56 mmol) was treated with 4M HCl in dioxane (2 mL). The mixture was stirred at room temperature for 3 h and concentrated under vacuum. The resulting residue was purified by flash chromatography (SiO$_2$, from 100% EtOAc to 30% MeOH in EtOAc) to afford 140 mg (0.38 mmol, 69% yield) of a pale orange oil identified as 4-[3-(methylamino)-1-phenylpropoxy]phenethyl acetate hydrochloride.

$^1$H NMR (400 MHz, CDCl$_3$) δ 7.36-7.20 (m, 5H), 7.00 (ddd, J=8.4, 2.8, 2.0, 2H), 6.75 (ddd, J=8.4, 2.8, 2.0, 2H), 5.29 (dd, J=8.2, 4.3 Hz, 1H), 4.16 (t, J=7.2 Hz, 2H), 3.12 (t, J=7.6 Hz, 2H), 2.79 (t, J=7.1 Hz, 2H), 2.61 (s, 3H), 2.50-2.33 (m, 2H), 2.00 (s, 3H).

$^{13}$C NMR (101 MHz, CDCl$_3$) δ 170.96, 156.05, 139.97, 130.43, 129.76, 128.85, 128.05, 125.79, 115.85, 76.94, 64.98, 46.29, 34.64, 34.11, 32.97, 20.95.

Example 11

N-[3-[4-(2-Hydroxyethyl)phenoxy]-3-phenylpropyl]-N-methyl-2-propylpentanamide

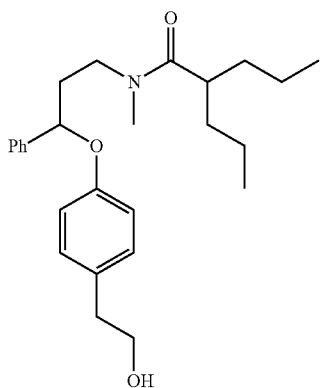 [SMILES: CCCC(CCC)C(=O)N(C)CCC(Oc1ccc(CCO)cc1)c1ccccc1]

2-[4-[3-(Methylamino)-1-phenylpropoxy]phenyl]ethanol (213 mg, 0.75 mmol) was dissolved in 2 mL of DCM and cooled to 0° C. Et$_3$N (209 μL, 1.50 mmol) and freshly prepared valproyl chloride (0.82 mmol) were successively added and the mixture was stirred at room temperature for 48 h. Then, the reaction mixture was diluted with EtOAc, quenched with water and successively washed with 5% HCl aqueous solution (2×), 5% NaOH aqueous solution (2×) and brine (2×). The organic layer was dried over anhydrous MgSO$_4$ and evaporated to dryness under vacuum. The resulting crude was purified by flash chromatography (SiO$_2$, from 100% hexane to 50% EtOAc in hexane) to afford 185 mg (0.45 mmol, 60% yield) of a colorless oil identified by $^1$H-NMR as N-[3-[4-(2-hydroxyethyl)phenoxy]-3-phenylpropyl]-N-methyl-2-propylpentanamide (mixture of rotamers).

$^1$H NMR (400 MHz, CDCl$_3$) δ 7.37-7.21 (m, 5H), 7.06-7.00 (m, 2H), 6.79-6.75 (m, 2H), 5.10 (dd, J=8.3, 4.4 Hz, 1H), 3.81-3.74 (m, 2H), 3.62-3.50 (m, 2H), 3.03 (s, 1.7H), 2.93 (s, 1.3H), 2.77-2.72 (m, 2H), 2.68-2.60 (m, 0.4H), 2.55-2.50 (m, 0.6H), 2.20-2.05 (m, 2H), 1.69-1.48 (m, 2H), 1.43-1.08 (m, 6H), 0.92-0.78 (m, 6H).

$^{13}$C NMR (101 MHz, CDCl$_3$) δ 176.45, 176.20, 156.35, 156.01, 141.48, 140.83, 131.04, 130.67, 129.70, 129.62, 128.64, 128.43, 127.64, 127.35, 125.58, 125.37, 115.65, 115.49, 77.83, 76.91, 63.41, 63.39, 46.13, 45.61, 40.80, 40.74, 38.09, 38.07, 38.00, 36.38, 36.12, 35.12, 35.10, 35.05, 35.04, 33.74, 20.71, 20.61, 20.57, 14.12, 14.11, 14.07.

Example 12

2-[4-(3-Amino-1-phenylpropoxy)phenyl]ethanol hydrochloride

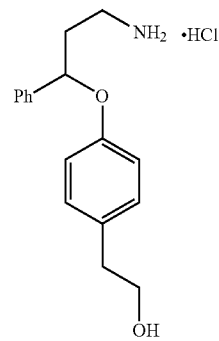

3-Amino-1-phenylpropan-1-ol [WO 2006011837]

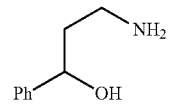

Benzoylacetonitrile (3.3 g, 22.7 mmol) was dissolved in dry THF (120 mL) under nitrogen and cooled to 0° C. Lithium aluminum hydride (4.3 g, 113.6 mmol) was carefully added portionwise and the resulting suspension was vigorously stirred at 0° C. for 30 min and progressively heated to reflux for 3.5 h. Then, it was cooled to 0° C. and carefully quenched with ice and 8 mL of 10% NaOH solution, diluted with EtOAc and stirred for 20 min at 0° C. The suspension was filtered through a Celite pad and concentrated under vacuum to afford 2.7 g (17.9 mmol, 79% yield) of brown oil that was employed in the next reaction without further purification.

tert-Butyl 3-hydroxy-3-phenylpropylcarbamate

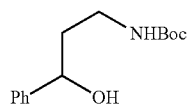

tert-Butyl 3-hydroxy-3-phenylpropylcarbamate was prepared in a 95% yield following the same procedure described for tert-butyl 3-hydroxy-3-phenyl propyl(methyl)carbamate (see Example 2).

Methyl 2-[4-[3-(tert-butoxycarbonylamino)-1-phenylpropoxy]phenyl]acetate

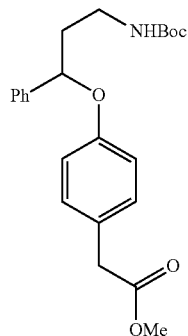

Methyl 2-[4-[3-(tert-butoxycarbonylamino)-1-phenylpropoxy]phenyl]acetate was prepared in a 32% yield following the same procedure described for methyl 2-[4-[3-[tert-butoxycarbonyl(methyl)amino]-1-phenylpropoxy]phenyl]acetate (see Example 2).

tert-Butyl 3-[4-(2-hydroxyethyl)phenoxy]-3-phenylpropylcarbamate

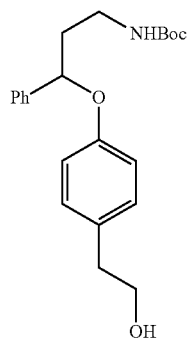

tert-Butyl 3-[4-(2-hydroxyethyl)phenoxy]-3-phenylpropylcarbamate was prepared in a 75% yield following the same procedure described for tert-butyl 3-[4-(2-hydroxyethyl)phenoxy]-3-phenylpropyl(methyl)carbamate (see Example 2).

2-[4-(3-Amino-1-phenylpropoxy)phenyl]ethanol

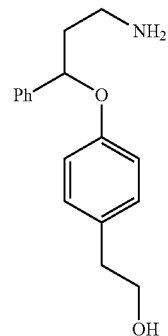

2-[4-(3-Amino-1-phenylpropoxy)phenyl]ethanol was prepared in a 91% yield following the same procedure described for 2-[4-[3-(methylamino)-1-phenylpropoxy]phenyl]ethanol (see Example 2).

2-[4-(3-Amino-1-phenylpropoxy)phenyl]ethanol hydrochloride

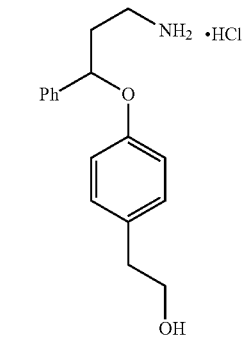 [SMILES: NCCC(Oc1ccc(CCO)cc1)c1ccccc1 ; Cl]

2-[4-(3-Amino-1-phenylpropoxy)phenyl]ethanol (850 mg, 3.13 mmol) was treated with 4M HCl in dioxane (2 mL). The mixture was stirred at room temperature for 1.5 h and concentrated under vacuum. The resulting residue was purified by flash chromatography (SiO$_2$, from 100% EtOAc to 30% MeOH in EtOAc) to afford 400 mg (1.30 mmol, 42% yield) of a white solid identified as 2-[4-(3-amino-1-phenylpropoxy)phenyl]ethanol hydrochloride.

m.p.: 68-70° C.

$^1$H NMR (400 MHz, CD$_3$OD) δ 7.45-7.22 (m, 5H), 7.02 (ddd, J=8.8, 2.8, 2.0 Hz, 2H), 6.81 (ddd, J=8.8, 2.8, 2.0 Hz, 2H), 5.39 (dd, J=8.3, 4.2 Hz, 1H), 3.65 (t, J=7.1 Hz, 2H), 3.21-3.03 (m, 2H), 2.69 (t, J=7.1 Hz, 2H), 2.35-2.14 (m, 2H).

$^{13}$C NMR (101 MHz, CD$_3$OD) δ 157.25, 142.01, 133.04, 130.80, 129.79, 129.03, 127.07, 117.03, 78.54, 64.25, 39.23, 38.00, 37.24.

Example 13

(R)-2-[4-[3-(Methylamino)-1-(thiophen-2-yl)propoxy]phenyl]ethanol

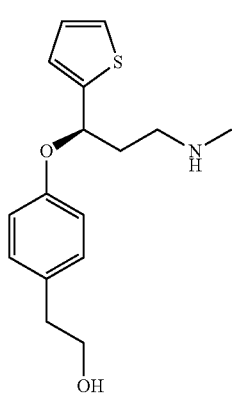 [SMILES: CNCC[C@@H](Oc1ccc(CCO)cc1)c1cccs1]

(R)-3-[4-[2-(tert-Butyldimethylsilyloxy)ethyl]phenoxy]-N-methyl-3-(thiophen-2-yl)propan-1-amine

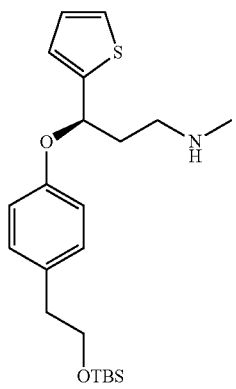 [SMILES: CNCC[C@@H](Oc1ccc(CCO[Si](C)(C)C(C)(C)C)cc1)c1cccs1]

Triphenylphosphine (2.34 g, 8.92 mmol), 4-[2-(tert-butyldimethylsilyloxy)ethyl]phenol (1.5 g, 5.94 mmol) and (S)-3-(methylamino)-1-(2-thienyl)-1-propanol (1.22 g, 7.12 mmol) were dissolved in toluene (60 mL). A solution of DEAD (~40% in toluene, 4.1 mL, 8.9 mmol) was added dropwise at room temperature during 15 min and the mixture was stirred for 18 h. The crude was then evaporated to dryness under vacuum and purified by flash chromatography (SiO$_2$, from 100% EtOAc to 30% MeOH in EtOAc) to afford (R)-3-[4-[2-(tert-butyldi-methylsilyloxy)ethyl]phenoxy]-N-methyl-3-(thiophen-2-yl)propan-1-amine as a pale yellow oil in 52% yield (0.746 g, 3.55 mmol).

$^1$H NMR (400 MHz, CDCl$_3$) δ 7.22-7.16 (m, 1H), 7.06-7.01 (m, 2H), 6.99-6.95 (m, 1H), 6.94-6.90 (m, 1H), 6.86-6.81 (m, 2H), 5.50 (dd, J=7.7, 5.3 Hz, 1H), 3.72 (t, J=7.2 Hz, 2H), 2.79-2.58 (m, 4H), 2.43 (s, 3H), 2.33-2.22 (m, 1H), 2.14-2.05 (m, 1H), 0.85 (s, 9H), −0.04 (s, 3H), −0.05 (s, 3H).

(R)-2-[4-[3-(Methylamino)-1-(thiophen-2-yl)propoxy]phenyl]ethanol

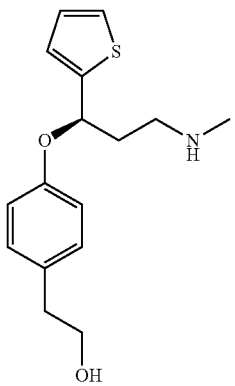 [SMILES: CNCC[C@@H](Oc1ccc(CCO)cc1)c1cccs1]

(R)-3-[4-[2-(tert-Butyldimethylsilyloxy)ethyl]phenoxy]-N-methyl-3-(thiophen-2-yl)propan-1-amine (0.480 g, 1.18 mmol) was dissolved in THF (10 mL) and 1M TBAF solution in THF (2.36 mL, 2.36 mmol) was added. After stirring at room temperature for 2 h the solvent was evaporated under vacuum. The residue was extracted with EtOAc/water and the aqueous phase was washed with EtOAc (×3). The combined organic fractions were washed with water (×3), dried over anhydrous MgSO$_4$ and evaporated to dryness under vacuum. The crude was purified by column chromatography (from EtOAc/MeOH 10% to EtOAc/MeOH 30%) to obtain (R)-2-[4-[3-(Methylamino)-1-(thiophen-2-yl)propoxy]phenyl]ethanol as an orange oil in 71% yield (0.243 g, 0.834 mmol).

$^1$H NMR (400 MHz, CDCl$_3$) δ 7.22 (dd, J=5.0, 1.2 Hz, 1H), 7.09-7.04 (m, 2H), 7.00-6.91 (m, 2H), 6.90-6.85 (m, 2H), 5.51 (dd, J=7.8, 5.3 Hz, 1H), 3.79 (t, J=6.5 Hz, 2H), 2.79-2.72 (m, 4H), 2.42 (s, 3H), 2.33-2.23 (m, 1H), 2.14-2.06 (m, 1H).

Example 14

4-[4-[3-(Methylamino)-1-phenylpropoxy]phenyl]butan-1-ol hydrochloride

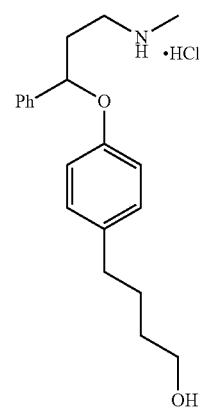 [SMILES: CNCCC(Oc1ccc(CCCCO)cc1)c1ccccc1 ; Cl]

4-(4-Methoxyphenyl)butyl acetate

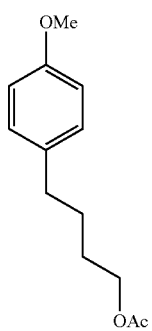 [SMILES: COc1ccc(CCCCOC(C)=O)cc1]

4-(4-Methoxyphenyl)butyl acetate was prepared in a 99% yield following the same procedure described for 4-[3-[tert-butoxycarbonyl(methyl)amino]-1-phenylpropoxy]phenethyl acetate (see Example 10).

$^1$H NMR (400 MHz, CDCl$_3$) δ 7.09 (ddd, J=8.8, 2.8, 2.0 Hz, 2H), 6.83 (ddd, J=8.8, 2.8, 2.0 Hz, 2H), 4.09-4.05 (m, 2H), 3.79 (s, 3H), 2.63-2.50 (m, 2H), 2.04 (s, 3H), 1.70-1.59 (m, 4H).

4-(4-Hydroxyphenyl)butyl acetate

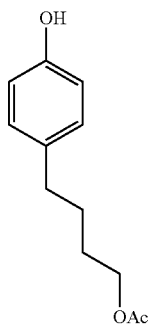 [SMILES: CC(=O)OCCCCc1ccc(O)cc1]

4-(4-Methoxyphenyl)butyl acetate (2.50 g, 11.2 mmol) was dissolved in dichloromethane (30 mL) and cooled to −78° C. under nitrogen. A BBr$_3$ solution (1M) in dichloromethane (24 mL, 24 mmol) was added dropwise and the solution was allowed to slowly warm to 0° C. during 5.5 h. The mixture was carefully quenched with water and concentrated under vacuum. The residue was diluted with EtOAc and successively washed with sat. solution of NaHCO$_3$ (3×) and brine (3×). The organic layer was then dried over anhydrous MgSO$_4$ and evaporated to dryness under vacuum to afford 2.11 g (10.1 mmol, 90% yield) of a pale green oil identified as 4-(4-hydroxyphenyl)butyl acetate which was used in the next reaction without further purification.

4-[4-[3-[tert-Butoxycarbonyl(methyl)amino]-1-phenylpropoxy]phenyl]butyl acetate

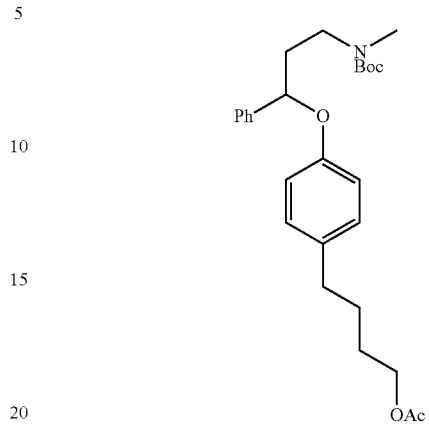

4-[4-[3-[tert-Butoxycarbonyl(methyl)amino]-1-phenylpropoxy]phenyl]butyl acetate was prepared in a 53% yield following the same procedure described for methyl 2-[4-[3-[tert-butoxycarbonyl(methyl)amino]-1-phenylpropoxy]phenyl]acetate (see Example 2).

$^1$H NMR (400 MHz, CDCl$_3$) δ 7.37-7.24 (m, 5H), 6.96 (d, J=8.5 Hz, 2H), 6.73 (d, J=8.5 Hz, 2H), 5.08-5.03 (m, 1H), 4.04 (t, J=6.3 Hz, 2H), 3.48-3.30 (m, 2H), 2.84 (s, 3H), 2.50 (t, J=7.0 Hz, 2H), 2.13-1.99 (m, 5H), 1.65-1.56 (m, 4H), 1.41 (br s, 9H).

tert-Butyl 3-[4-(4-hydroxybutyl)phenoxy]-3-phenylpropyl(methyl)carbamate

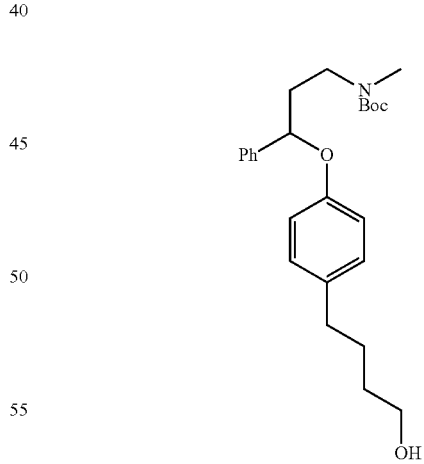

4-[4-[3-[tert-Butoxycarbonyl(methyl)amino]-1-phenylpropoxy]phenyl]butyl acetate (1.37 g, 3.00 mmol) was dissolved in MeOH (30 mL) and catalytic MeONa (10 mg) was added. The solution was stirred for 3 h and concentrated under vacuum to afford 1.25 g of a colorless oil that was used in the next reaction without further purification.

4-[4-[3-(Methylamino)-1-phenylpropoxy]phenyl]butan-1-ol

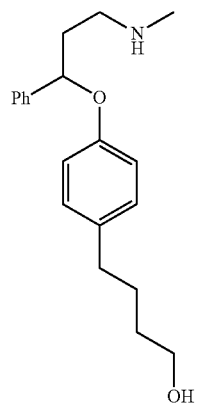 [SMILES: CNCCC(Oc1ccc(CCCCO)cc1)c1ccccc1]

4-[4-[3-(Methylamino)-1-phenylpropoxy]phenyl]butan-1-ol was prepared following the same procedure described for 2-[4-[3-(methylamino)-1-phenyl propoxy]phenyl]ethanol (see Example 2).

4-[4-[3-(Methylamino)-1-phenylpropoxy]phenyl]butan-1-ol hydrochloride

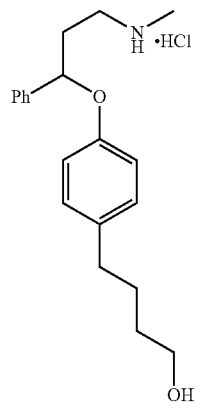 [SMILES: CNCCC(Oc1ccc(CCCCO)cc1)c1ccccc1 ; Cl]

4-[4-[3-(Methylamino)-1-phenylpropoxy]phenyl]butan-1-ol hydrochloride was obtained as a white solid in a 61% yield (last three steps) following the same procedure described for 4-[3-(methylamino)-1-phenylpropoxy]phenethyl acetate hydrochloride (see Example 10).

$^1$H NMR (400 MHz, CD$_3$OD) δ 7.49-7.22 (m, 5H), 7.01 (ddd, J=8.8, 2.8, 2.0 Hz, 2H), 6.79 (ddd, J=8.8, 2.8, 2.0 Hz, 2H), 5.37 (dd, J=8.4, 4.1 Hz, 1H), 3.52 (t, J=6.4 Hz, 2H), 3.28-3.13 (m, 2H), 2.72 (s, 3H), 2.52 (t, J=6.6 Hz, 2H), 2.37-2.15 (m, 2H), 1.63-1.54 (m, 2H), 1.53-1.44 (m, 2H).

$^1$H NMR (101 MHz, CD$_3$OD) δ 156.89, 141.97, 136.59, 130.21, 129.83, 129.09, 127.08, 117.00, 78.54, 62.75, 47.70, 36.04, 35.69, 33.87, 33.10, 29.01.

Example 15

(E)-tert-Butyl [3-[4-(3-hydroxyprop-1-enyl)phenoxy]-3-phenylpropyl](methyl)carbamate

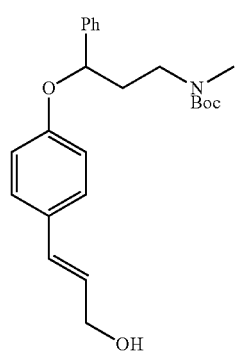 [SMILES: CN(CCC(Oc1ccc(/C=C/CO)cc1)c1ccccc1)C(=O)OC(C)(C)C]

(E)-Methyl 3-(4-hydroxyphenyl)acrylate

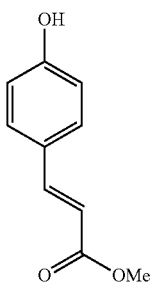 [SMILES: COC(=O)/C=C/c1ccc(O)cc1]

p-Coumaric acid (3.0 g, 18.3 mmol) was suspended in MeOH (12 mL) and treated with 3 drops of conc. H$_2$SO$_4$. The mixture was refluxed for 21 h. The resulting clear solution was cooled to rt and concentrated under vacuum to yield a white solid that was dissolved in EtOAc and successively washed with sat. NaHCO$_3$ solution (3×) and brine (3×). The organic layer was dried over anhydrous MgSO$_4$ and evaporated to dryness under vacuum to afford 3.22 g (18.1 mmol, 99% yield) of a white solid identified by NMR as (E)-methyl 3-(4-hydroxyphenyl)acrylate.

$^1$H NMR (400 MHz, CDCl$_3$) δ 7.64 (d, J=16.0 Hz, 1H), 7.43 (ddd, J=8.8, 2.8, 2.0 Hz, 2H), 6.86 (ddd, J=8.8, 2.8, 2.0 Hz, 2H), 6.30 (d, J=16.0 Hz, 1H), 5.47 (br s, 1H), 3.80 (s, 3H).

(E)-Methyl 3-[4-[3-[tert-butoxycarbonyl(methyl)amino]-1-phenylpropoxy]phenyl]acrylate

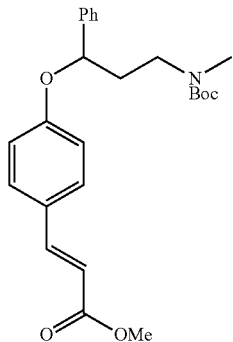 [SMILES: COC(=O)/C=C/c1ccc(OC(CCN(C)C(=O)OC(C)(C)C)c2ccccc2)cc1]

(E)-methyl 3-[4-[3-[tert-butoxycarbonyl(methyl)amino]-1-phenylpropoxy]phenyl]acrylate was prepared in a 67% yield following the same procedure described for methyl 2-(4-(3-(tert-butoxycarbonyl(methyl)amino)-1-phenylpropoxy) phenyl) acetate (see Example 2).

$^1$H NMR (400 MHz, CDCl$_3$) δ 7.57 (d, J=16.0 Hz, 1H), 7.38-7.28 (m, 7H), 6.82 (ddd, J=8.8, 2.8, 2.0 Hz, 2H), 6.24 (d, J=16.0 Hz, 1H), 5.18-5.12 (m, 1H), 3.77 (s, 3H), 3.52-3.28 (m, 2H), 2.85 (s, 3H), 2.24-2.06 (m, 2H), 1.39 (br s, 9H).

(E)-tert-Butyl [3-[4-(3-hydroxyprop-1-en-1-yl)phenoxy]-3-phenylpropyl](methyl) carbamate

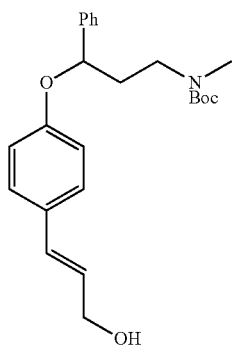 [SMILES: CN(CCC(Oc1ccc(/C=C/CO)cc1)c1ccccc1)C(=O)OC(C)(C)C]

(E)-Methyl 3-[4-[3-[tert-butoxycarbonyl(methyl)amino]-1-phenylpropoxy]phenyl]acrylate (1.61 g, 3.79 mmol) was dissolved in dry THF (40 mL) under nitrogen and cooled to 0° C. DIBALH solution (1M) in toluene (22.7 mL, 22.7 mmol) was added dropwise and the resulting solution was allowed to slowly warm to 10° C. for 3 h. Then, it was quenched with a sat. NH$_4$Cl solution, diluted with EtOAc and filtered. The filtrate was washed with brine (3x), dried over anhydrous MgSO$_4$ and concentrated under vacuum. The residue was purified by flash chromatography (from hexane to 40% EtOAc in hexane) to afford 1.37 g (3.45 mmol, 91%) of a colorless oil identified as (E)-tert-butyl [3-[4-(3-hydroxyprop-1-en-1-yl)phenoxy]-3-phenylpropyl](methyl)carbamate.

$^1$H NMR (400 MHz, CDCl$_3$) δ 7.39-7.15 (m, 7H), 6.81-6.76 (m, 2H), 6.48 (d, J=16.0 Hz, 1H), 6.17 (dt, J=16.0, 6.0 Hz, 1H), 5.15-5.09 (m, 1H), 4.26 (d, J=5.4 Hz, 2H), 3.50-3.28 (m, 2H), 2.84 (s, 3H), 2.21-1.99 (m, 2H), 1.39 (br s, 9H).

Example 16

3-[4-[3-Methylamino)-1-phenylpropoxy]phenyl]propan-1-ol hydrochloride

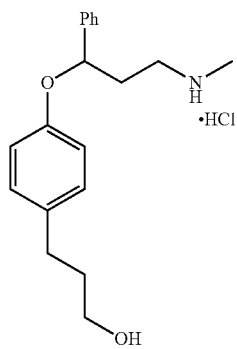 [SMILES: CNCCC(Oc1ccc(CCCO)cc1)c1ccccc1 ; Cl]

Methyl 3-(4-hydroxyphenyl)propanoate

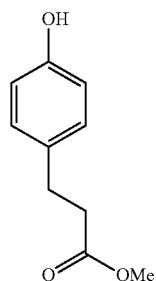 [SMILES: COC(=O)CCc1ccc(O)cc1]

To a solution of (E)-methyl 3-(4-hydroxyphenyl)acrylate (1.0 g, 5.6 mmol) in EtOH (20 mL), Pd/C (0.1 g) was added. The reaction mixture was vigorously stirred under hydrogen atmosphere (1 bar) at room temperature for 21 h. The suspension was filtered through a Celite pad and evaporated to dryness under vacuum to afford 1.0 g (5.6 mmol, 99% yield) of an oil identified as methyl 3-(4-hydroxyphenyl)propanoate.

$^1$H NMR (400 MHz, CDCl$_3$) δ 7.07 (ddd, J=8.8, 2.8, 2.0 Hz, 2H), 6.76 (ddd, J=8.8, 2.8, 2.0 Hz, 2H), 4.72 (br s, 1H), 3.67 (s, 3H), 2.88 (t, J=7.8 Hz, 2H), 2.60 (t, J=7.8 Hz, 2H).

Methyl 3-[4-[3-[tert-butoxycarbonyl(methyl)amino]-1-phenylpropoxy]phenyl]propanoate

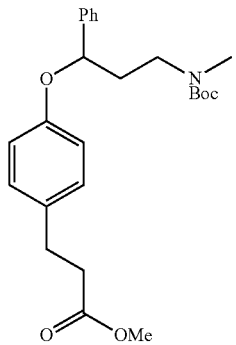 [SMILES: COC(=O)CCc1ccc(OC(CCN(C)C(=O)OC(C)(C)C)c2ccccc2)cc1]

Methyl 3-[4-[3-[tert-butoxycarbonyl(methyl)amino]-1-phenylpropoxy]phenyl] propanoate was prepared in a 63% yield following the same procedure described for methyl 2-[4-[3-[tert-butoxycarbonyl(methyl)amino]-1-phenylpropoxy]phenyl]acetate (see Example 2).

$^1$H NMR (400 MHz, CDCl$_3$) δ 7.34-7.22 (m, 5H), 6.98 (ddd, J=8.8, 2.8, 2.0 Hz, 2H), 6.73 (ddd, J=8.8, 2.8, 2.0 Hz, 2H), 5.06 (dd, J=8.4, 4.0 Hz, 1H), 3.64 (s, 3H), 3.48-3.27 (m, 2H), 2.85-2.79 (m, 5H), 2.53 (t, J=7.8 Hz, 2H), 2.18-2.00 (m, 2H), 1.39 (br s, 9H).

tert-Butyl 3-[4-(3-hydroxypropyl)phenoxy]-3-phenylpropyl(methyl)carbamate

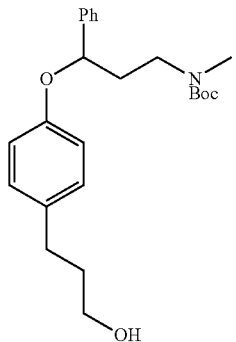 [SMILES: CN(CCC(Oc1ccc(CCCO)cc1)c1ccccc1)C(=O)OC(C)(C)C]

tert-Butyl 3-[4-(3-hydroxypropyl)phenoxy]-3-phenylpropyl(methyl)carbamate was prepared in a 90% yield following the same procedure described for tert-butyl 3-[4-(2-hydroxyethyl)phenoxy]-3-phenylpropyl(methyl)carbamate (see Example 2).

3-[4-[3-(Methylamino)-1-phenylpropoxy]phenyl]propan-1-ol

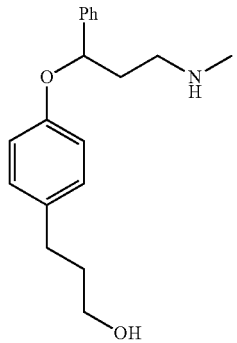 [SMILES: CNCCC(Oc1ccc(CCCO)cc1)c1ccccc1]

3-[4-[3-(Methylamino)-1-phenylpropoxy]phenyl]propan-1-ol was prepared in a 95% yield following the same procedure described for 2-[4-[3-(methylamino)-1-phenylpropoxy]phenyl]etanol (See Example 2).

3-[4-[3-(Methylamino)-1-phenylpropoxy]phenyl]propan-1-ol hydrochloride

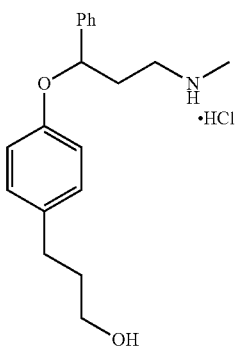 [SMILES: CNCCC(Oc1ccc(CCCO)cc1)c1ccccc1 ; Cl]

3-[4-[3-(Methylamino)-1-phenylpropoxy]phenyl]propan-1-ol hydrochloride was obtained as a white solid in a 48% yield following the same procedure described for 4-[3-(methylamino)-1-phenylpropoxy]phenethyl acetate hydrochloride (see Example 10).

$^1$H NMR (400 MHz, CD$_3$OD) δ 7.45-7.24 (m, 5H), 7.02 (ddd, J=8.8, 2.8, 2.0 Hz, 2H), 6.80 (ddd, J=8.8, 2.8, 2.0 Hz, 2H), 5.36 (dd, J=8.3, 4.1 Hz, 1H), 3.50 (t, J=6.5 Hz, 2H), 3.27-3.14 (m, 2H), 2.72 (s, 3H), 2.57-2.51 (m, 2H), 2.38-2.16 (m, 2H), 1.77-1.69 (m, 2H).

$^{13}$C NMR (101 MHz, CD$_3$OD) δ 156.91, 141.94, 136.17, 130.22, 129.82, 129.09, 127.09, 117.06, 78.54, 62.14, 47.69, 36.02, 35.55, 33.87, 32.09.

Example 17

[4-[3-(Methylamino)-1-phenylpropoxy]phenyl]methanol hydrochloride

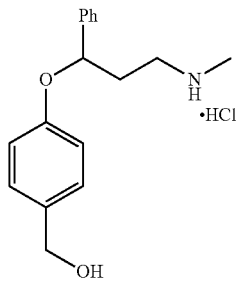 [SMILES: CNCCC(Oc1ccc(CO)cc1)c1ccccc1 ; Cl]

Methyl 4-[3-[tert-butoxycarbonyl(methyl)amino]-1-phenylpropoxy]benzoate

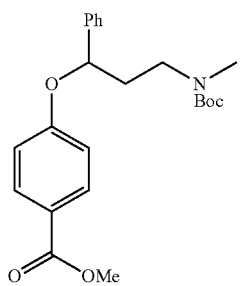 [SMILES: CNCCC(Oc1ccc(C(=O)OC)cc1)c1ccccc1]

Methyl 4-[3-[tert-butoxycarbonyl(methyl)amino]-1-phenylpropoxy]benzoate was prepared in a 62% yield following the same procedure described for methyl 2-[4-[3-[tert-butoxycarbonyl(methyl)amino]-1-phenylpropoxy]phenyl]acetate (see Example 2).

$^1$H NMR (400 MHz, CDCl$_3$) δ 7.90-7.84 (m, 2H), 7.37-7.23 (m, 5H), 6.86-6.81 (m, 2H), 5.21-5.18 (m, 1H), 3.84 (s, 3H), 3.54-3.29 (s, 1H), 2.85 (br s, 3H), 2.25-2.05 (m, 2H), 1.48-1.32 (br s, 9H).

tert-Butyl 3-[4-(hydroxymethyl)phenoxy]-3-phenylpropyl(methyl)carbamate

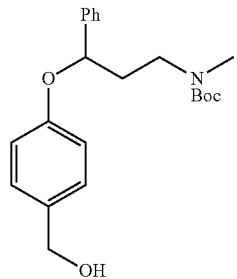 [SMILES: CNCCC(Oc1ccc(CO)cc1)c1ccccc1]

tert-Butyl 3-[4-(hydroxymethyl)phenoxy]-3-phenylpropyl(methyl)carbamate was prepared in a 90% yield following the same procedure described for tert-butyl 3-[4-(2-hydroxyethyl)phenoxy]-3-phenylpropyl(methyl)carbamate (see Example 2).

[4-[3-(Methylamino)-1-phenylpropoxy]phenyl]methanol

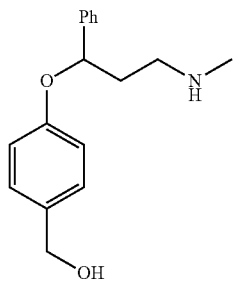 [SMILES: CNCCC(Oc1ccc(CO)cc1)c1ccccc1]

[4-[3-(Methylamino)-1-phenylpropoxy]phenyl]methanol was prepared following the same procedure described for 2-[4-[3-(methylamino)-1-phenylpropoxy]phenyl]ethanol (see Example 2).

[4-[3-(Methylamino)-1-phenylpropoxy]phenyl]methanol hydrochloride

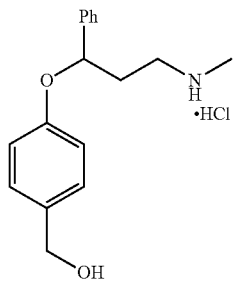 [SMILES: CNCCC(Oc1ccc(CO)cc1)c1ccccc1 ; Cl]

[4-[3-(Methylamino)-1-phenylpropoxy]phenyl]methanol hydrochloride was obtained as a white solid in a 24% yield for the last two steps following the same procedure described for 4-[3-(methylamino)-1-phenylpropoxy]phenethyl acetate hydrochloride (see Example 10).

$^1$H NMR (400 MHz, CD$_3$OD) δ 7.41-7.31 (m, 4H), 7.29-7.24 (m, 1H), 7.16 (ddd, J=8.8, 2.8, 2.0 Hz, 2H), 6.85 (ddd, J=8.8, 2.8, 2.0 Hz, 2H), 5.41 (dd, J=8.4, 4.1 Hz, 1H), 4.45 (s, 2H), 3.28-3.13 (m, 2H), 2.72 (s, 3H), 2.38-2.17 (m, 2H).

$^{13}$C NMR (101 MHz, CD$_3$OD) δ 158.10, 141.67, 135.53, 129.84, 129.48, 129.18, 127.21, 117.09, 78.36, 64.72, 56.26, 43.70, 34.55.

Example 18

2-[4-Morpholin-2-ylmethoxy)phenyl]ethanol hydrochloride

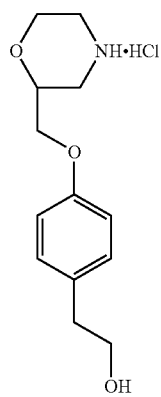

2-[4-[(4-Benzylmorpholin-2-yl)methoxy]phenyl]ethanol

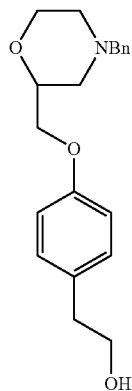

NaH (670 mg, 16.8 mmol) was suspended in dry DMF (8 mL) under nitrogen atmosphere. After cooling the mixture to 0° C., a solution of 4-(2-hydroxyethyl)phenol (1.86 g, 13.5 mmol) in dry DMF (8 mL) was added dropwise. The resulting suspension was kept at 0° C. for 10 minutes and stirred at 70° C. for 1 h. Then, it was cooled to room temperature and 4-benzyl-2-(chloromethyl)morpholine (1.52 g, 6.73 mmol) was added dropwise. The reaction mixture was stirred at 80° C. for 65 h and, after cooling to rt, was diluted with EtOAc and carefully quenched with water. The two layers were separated and the aqueous phase was extracted with EtOAc (6×). The combined organic fractions were washed with brine (3×) and water (3×), dried over anhydrous $Na_2SO_4$ and evaporated to dryness under vacuum. The resulting oil (3.34 g) was purified by flash chromatography (from hexane to 60% EtOAc in hexane) to afford 1.13 g (3.45 mmol, 51%) of a colorless oil identified as 2-[4-[(4-benzylmorpholin-2-yl)methoxy]phenyl]ethanol.

$^1$H NMR (400 MHz, $CDCl_3$) δ 7.34-7.24 (m, 5H), 7.10 (d, J=8.6, 2H), 6.86-6.80 (m, 2H), 4.00-3.84 (m, 4H), 3.79 (t, J=6.6, 2H), 3.72 (m, 1H), 3.56-3.47 (m, 2H), 2.86 (d, J=11.2, 1H), 2.78 (t, J=6.6, 2H), 2.67 (d, J=11.4, 1H), 2.21 (td, J=11.4, 3.3, 1 H), 2.11-2.02 (m, 1H).

2-[4-(Morpholin-2-ylmethoxy)phenyl]ethanol hydrochloride

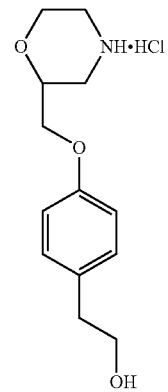

To a solution of 2-[4-[(4-benzylmorpholin-2-yl)methoxy]phenyl]ethanol (1.1 g, 3.45 mmol) in MeOH (100 mL) in a pressure reactor, concentrated HCl (350 μl, 4.2 mmol) and Pd/C (0.1 g) were added. The reaction mixture was vigorously stirred under a hydrogen atmosphere (5 bar) at room temperature for 24 h. The suspension was filtered through a Celite pad and evaporated to dryness under vacuum to afford 0.85 g of a pale yellow solid. Recrystallization of this solid in hot isopropyl alcohol furnished 0.60 g (2.42 mmol, 70% yield) of a white solid identified as 2-[4-(morpholin-2-ylmethoxy)phenyl]ethanol hydrochloride.

m.p.: 163-169° C.

$^1$H NMR (400 MHz, $D_2O$) δ 7.29 (d, J=8.3, 2H), 7.01 (d, J=8.3, 2H), 4.24 (m, 3H), 4.19-4.10 (m, 1H), 3.98 (t, J=11.8, 1H), 3.83 (t, J=6.6, 2H), 3.52 (d, J=12.9, 1H), 3.43 (d, J=13.0, 1H), 3.29 (m, 2H), 2.84 (t, J=6.6, 2H).

$^{13}$C NMR (101 MHz, $D_2O$) δ 156.4, 132.6, 130.4, 115.1, 72.1, 68.1, 63.7, 62.8, 43.9, 42.7, 37.0.

Example 19

[5-[3-(Methylamino)-1-phenylpropoxy]-1,3-phenylene]dimethanol hydrochloride

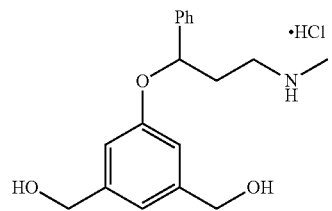 [SMILES: CNCCC(Oc1cc(CO)cc(CO)c1)c1ccccc1 ; Cl]

Dimethyl 5-hydroxyisophthalate

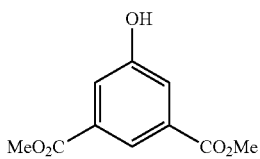

Dimethyl 5-hydroxyisophthalate was prepared in a 80% yield following the same procedure described for (E)-methyl 3-(4-hydroxyphenyl)acrylate (see Example 15).

$^1$H NMR (400 MHz, CDCl$_3$) δ 8.27-8.25 (m, 1H), 7.77-7.70 (m, 2H), 5.51 (br s, 1H), 3.94 (s, 6H).

Dimethyl 5-[3-[tert-butoxycarbonyl(methyl)amino]-1-phenylpropoxy]isophthalate

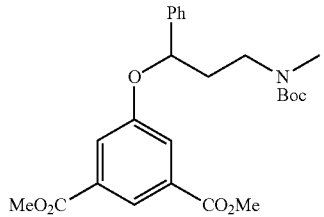

Dimethyl 5-[3-[tert-butoxycarbonyl(methyl)amino]-1-phenylpropoxy]isophthalate was prepared in a 86% yield following the same procedure described for methyl 2-[4-[3-[tert-butoxycarbonyl(methyl)amino]-1-phenylpropoxy]phenyl]acetate (see Example 2).

$^1$H NMR (400 MHz, CDCl$_3$) δ 8.19-8.17 (m, 1H), 7.70-7.68 (m, 2H), 7.37-7.29 (m, 5H), 5.23 (dd, J=7.6, 3.6 Hz, 1H), 3.89 (s, 6H), 3.50-3.28 (m, 2H), 2.85 (s, 3H), 2.25-2.14 (m, 1H), 2.14-2.06 (m, 1H), 1.35 (br s, 9H).

tert-Butyl 3-[3,5-bis(hydroxymethyl)phenoxy]-3-phenylpropyl(methyl)carbamate

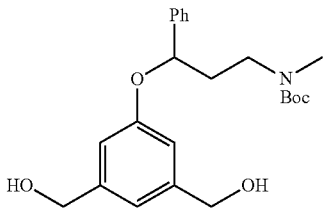 [SMILES: CNCCC(Oc1cc(CO)cc(CO)c1)c1ccccc1]

Dimethyl 5-[3-[tert-butoxycarbonyl(methyl)amino]-1-phenylpropoxy]isophthalate (1.0 g, 2.2 mmol) was dissolved in dry THF (30 mL) under nitrogen and cooled to 0° C. Lithium aluminum hydride (380 mg, 10.0 mmol) was added portionwise and the resulting suspension was vigorously stirred at 0° C. for 2 h and at room temperature for 45 min. Then, it was cooled to 0° C. and carefully quenched with ice and 0.3 mL of 10% NaOH solution, diluted with EtOAc and stirred for 10 min at 0° C. The suspension was filtered through a Celite pad and concentrated under vacuum to afford 0.86 g (2.1 mmol, 96% yield) of a colorless paste identified as tert-butyl 3-[3,5-bis(hydroxymethyl)phenoxy]-3-phenylpropyl (methyl)carbamate that was used in the next reaction without further purification.

[5-[3-(Methylamino)-1-phenylpropoxy]-1,3-phenylene]dimethanol

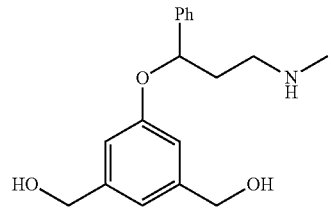 [SMILES: CNCCC(Oc1cc(CO)cc(CO)c1)c1ccccc1]

[5-[3-(Methylamino)-1-phenylpropoxy]-1,3-phenylene]dimethanol was prepared following the same procedure described for intermediate 2-[4-[3-(methylamino)-1-phenylpropoxy]phenyl]ethanol (see Example 2).

[5-[3-(Methylamino)-1-phenylpropoxy]-1,3-phenylene]dimethanol hydrochloride

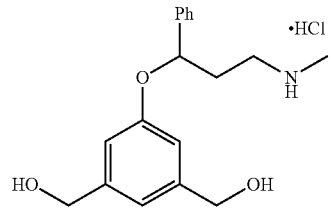 [SMILES: CNCCC(Oc1cc(CO)cc(CO)c1)c1ccccc1 ; Cl]

[5-[3-(Methylamino)-1-phenylpropoxy]-1,3-phenylene] dimethanol hydrochloride was obtained in 40% yield (last two steps) prepared following the same procedure described for 4-[3-(methylamino)-1-phenylpropoxy]phenethyl acetate hydrochloride (see Example 10).

$^1$H NMR (400 MHz, CD$_3$OD) δ 7.44-7.40 (m, 2H), 7.36-7.31 (m, 2H), 7.28-7.22 (m, 1H), 6.87 (s, 1H), 6.84 (s, 2H), 5.46 (dd, J=8.4, 4.2 Hz, 1H), 4.48 (s, 4H), 3.27-3.11 (m, 2H), 2.69 (s, 3H), 2.39-2.19 (m, 2H).

$^{13}$C NMR (101 MHz, CD$_3$OD) δ 159.03, 144.33, 141.77, 129.81, 129.10, 127.11, 119.18, 114.36, 78.30, 64.84, 47.59, 35.95, 33.85.

The compounds of Examples 20 to 35 are presented in Table 1. These compounds are prepared employing the procedures of reaction schemes 1 to 6 above. The starting materials for these compounds are either commercially available or can be synthesized using general methods.

TABLE 1

| Example | Structure |
|---|---|
| 20 | 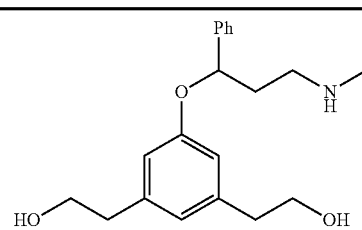 |

TABLE 1-continued
| Example | Structure |
|---|---|
| 21 | 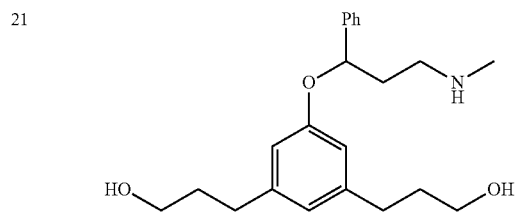 |
| 22 | 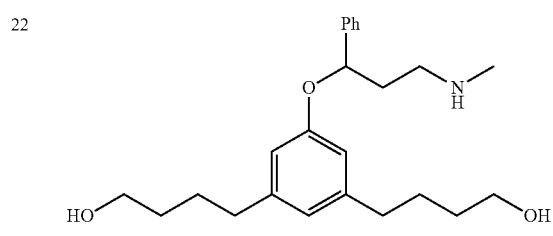 |
| 23 | 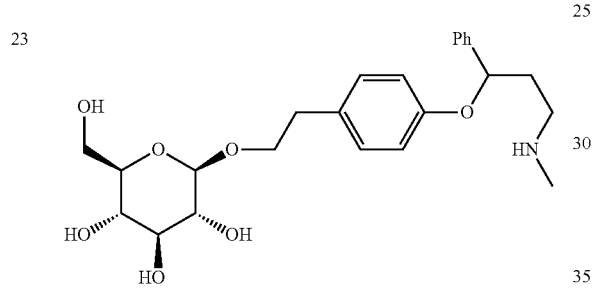 |
| 24 | 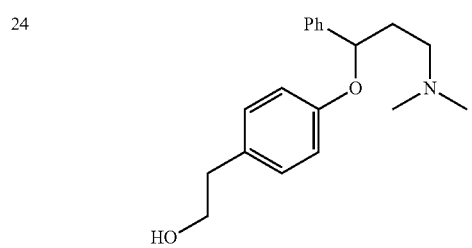 |
| 25 | 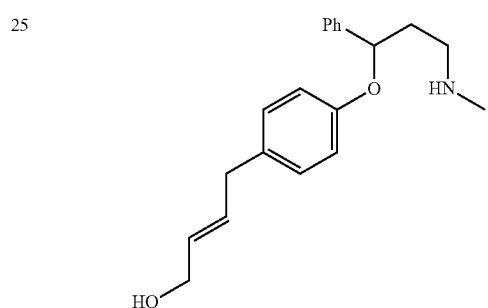 |
| 26 |  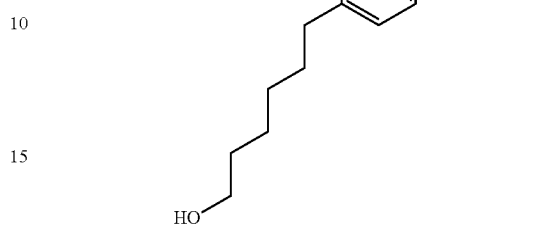 |
| 27 | 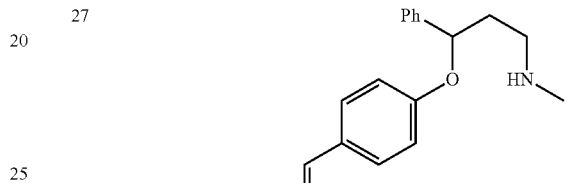 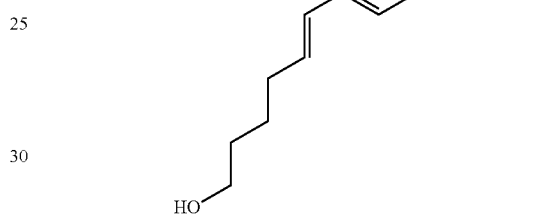 |
| 28 | 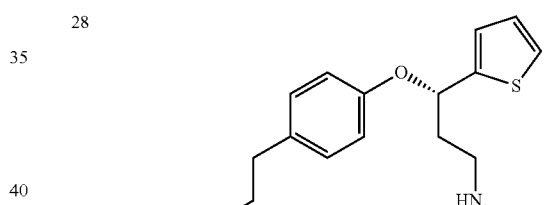 |
| 29 | 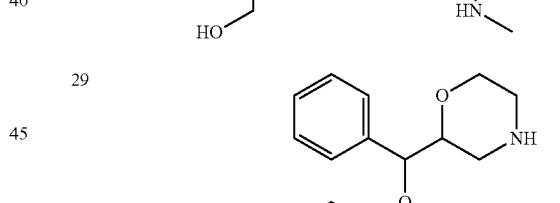 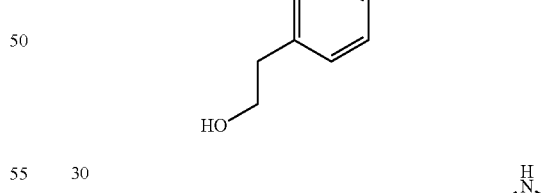 |
| 30 | 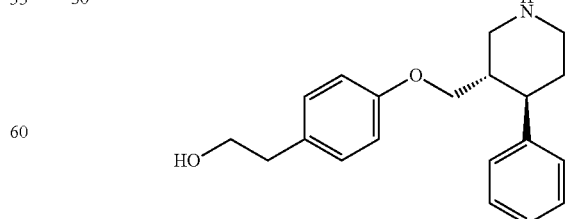   |

TABLE 1-continued

| Example | Structure |
|---|---|
| 31 | (structure) |
| 32 | (structure) |
| 33 | (structure) |
| 34 | (structure) |
| 35 | (structure) |

Biological Assays

The following examples illustrate the biological activity of compounds of formula (I) and should not be considered as limiting the scope of the invention.

Norepinephrine Transporter Binding Radioligand Inhibition

The norepinephrine (NE) transporter removes NE from the synaptic cleft. The NE transporter terminates the effects of serotonin, enabling its reuse by the presynaptic neuron. The in vitro binding of the compounds of the invention to the NE transporter and the percent inhibition of control-specific binding ([$^3$H]-nisoxetine in human recombinant CHO cells) is determined following the method described in Pacholczyk et al., (Nature 1991, 350(6316): 350-4.

The percentage inhibition of Examples 2, 12, 13, 14, 16, 17 and 19 is shown in Table 2).

TABLE 2

| Examples | concentration (μM) | norepinephrine binding inhibition |
|---|---|---|
| 2 | 5 | 95% |
| 12 | 10 | 79% |
| 13 | 10 | 80% |
| 14 | 10 | 85% |
| 16 | 10 | 90% |
| 17 | 10 | 94% |
| 19 | 10 | 75% |

The percentage inhibition for compounds 1, 3-11, 15, 18 and 20-32 at 10 μM were between 65 and 90% in this assay.

Serotonin Transporter Binding Radioligand Inhibition

The serotonin transporter removes serotonin from the synaptic deft. The serotonin transporter terminates the effects of serotonin, enabling its reuse by the presynaptic neuron. The binding of the compounds of the invention to the serotonin transporter and the percent inhibition of control-specific binding ([$^3$H-]-imipramine in human recombinant CHO cells) is determined following the method described in Tatsumi et al. Eur J Pharmacol 1999, 368(2-3): 277-83).

The percentage inhibition of Examples 12, 13, 14, 16, 17 and 19 is shown in Table 3.

TABLE 3

| Examples | Concentration (µM) | serotonin binding inhibition |
|---|---|---|
| 2 | 5 | 82% |
| 12 | 10 | 78% |
| 13 | 10 | 79% |
| 14 | 10 | 89% |
| 16 | 10 | 78% |
| 17 | 10 | 97% |
| 19 | 10 | 79% |

The percentage inhibition for compounds 1, 3-11, 15, 18 and 20-32 at 10 µM were between 68 and 82% in this assay.

Uptake Inhibition of Serotonin and Norepinephrine

The effect of the compounds of the present invention as inhibitors of the uptake of norepinephrine and serotonin in cellular assays at concentrations that range from 10 mM to 1 nM is determined following the methods described in Galli, A. et al. J Exp Biol 1995, 198(Pt. 10): 2197-212 and Gu, H. et al. J Biol Chem. 1994, 269(10):7124-30.

The percentage inhibition of Examples 2, 12, 13, 14, 16, 17 and 19 is shown in Table 4.

TABLE 4

| Examples | Norepinephrine reuptake inhibition (IC50 µM) | Serotonin reuptake inhibition (IC50 µM) |
|---|---|---|
| 2 | 0.086 | 0.348 |
| 12 | 2.7 | 1.00 |
| 13 | 2.8 | 2.6 |
| 14 | 0.740 | 0.32 |
| 16 | 0.46 | 2.36 |
| 17 | 0.13 | 0.42 |
| 19 | 1.59 | 4.35 |

In the case of the product of Example 2, significant inhibition was noted in the uptake of norepinephrine, with an $IC_{50}$ of 0.0864 µM, and in the uptake of serotonin, with an $IC_{50}$ of 0.328 µM.

Norepinephrine reuptake inhibitory activity for compounds 1, 3-11, 15, 18 and 20-32 was determined to be in the IC50 (µM) range of 1.6 to 2.9.

Serotonine reuptake inhibitory activity for compounds 1, 3-11, 15, 18 and 20-32 was determined to be in the IC50 (µM) range of 2.5 to 4.8.

Antidepressant Activity in the Forced Swimming Test in Mice

The antidepressant activity was determined using the forced swimming test described in Porsolt, R.-D. et al. Arch Int Pharmacodyn 1977, 229(2): 327-36.

Reduction in the duration of immobility by 50% or more relative to the control group indicates possible antidepressant activity. Also, one-way ANOVA followed by Dunnett's test was applied to compare the test compound-treated and vehicle control groups. Significance was considered to be P<0.05. The compound of Example 2 at a dose of 30 mg/kg administered by intraperitoneal injection was associated with significant antidepressant activity at 60 minutes post-dosing (P<0.05, one-way ANOVA followed by Dunnett's test). In addition, the compound of Example 2 when administered p.o. at a dose of 90 mg/kg also showed significant activity in this test, suggesting antidepressant activity for the compound.

Antidepressant Activity in the Tail Suspension Assay

Another method of measuring antidepressant activity that may be used to evaluate the compounds of the present invention is the tail suspension test in mice described in Vogel, H. G. and Vogel, W. H. (Eds.) Drug Discovery and Evaluation, Springer-Verlag Berlin Heidelberg, 1997) pp. 304-3059). The mouse tail suspension assay was conducted 60 minutes after dosing. The duration of immobility was recorded for a period of 5 minutes after tail suspension was initiated, and reduction in the duration of immobility by ≥50% relative to the control group indicated antidepressant activity. Statistical analysis was also performed by using one-way ANOVA followed by Dunnett's test to compare the data of test compound-treated and vehicle control groups. Significance was considered to be P<0.05.

The compound of Example 2 at a dose of 30 mg/kg administered intraperitoneally was associated with a significant effect (reduction in the duration of immobility by ≥50%) relative to the control group) in the mouse tail suspension assay. Desipramine (30 mg/kg), the positive standard, elicited a significant effect at 60 minutes after oral dosing (P<0.05 vs. vehicle control; one-way ANOVA followed by Dunnett's test). Additionally, the compound of Example 2 administered at 90 mg/kg showed significant activity in this test, suggesting an antidepressant effect for the compound. The compounds of Examples 3 and 4 were active at 90 mg/kg p.o. Additionally, Example 4 showed significant activity at 30 mg/kg p.o.

Analgesic Activity in the Mouse Formalin Assay

The analgesic activity of the compounds of the present invention is determined making use of the mouse formalin test described in Hunskaar, S. J Neurosci Methods 1985, 14(1): 69-76. The hind paw licking time was measured at 5-minute intervals for 30 minutes following subplantar injection of formalin (0.02 mL, 2%). Statistical analysis using one-way ANOVA followed by Dunnett's test was applied for comparison between the test substance-treated and vehicle control groups. P<0.05 was considered significant.

Intraperitoneal administration of the compound of Example 2 at a dose of 30 mg/kg and oral administration of 90, 30 and 3 mg/kg demonstrated significant analgesic activity following formalin challenge in mice compared to the vehicle control group. The compound of Example 3 was also active when administered by the oral route at 90 mg/kg, whereas the compound of Example 4 was active at 90 and 30 mg/kg after oral intake. The compound of Example 18 demonstrated analgesic activity at 90 mg/kg administered by the oral route in this model.

Binding to the Dopamine Transporter (DAT)

$Na^+/Cl^-$-dependent neurotransmitters, which constitute a gene superfamily, are crucial for limiting neurotransmitter activity. The action of dopamine is terminated, in part, through its uptake into presynaptic dopaminergic neurons by the plasma membrane norepinephrine transporter (NET). The monoamine transporters, such as DAT, are high-affinity targets for psychostimulants and antidepressants. These agents, by blocking transporters and consequently preventing neuronal uptake, elevate levels of extracellular neurotransmitter concentrations in both the central and peripheral nervous system, contributing to their behavioral and autonomic effects.

Human dopamine transporters expressed in CHO—K1 cells are used in modified Tris-HCl buffer at pH 7.4. A 40-$mg^+$ aliquot is incubated with 0.15 nM of the DAP ligand ($[^{125}I]$-RTI-55) for 3 hours at 4° C. Non-specific binding is estimated in the presence of 10 mM nomifensine. Membranes are filtered and washed, the filters are then counted to determine specifically bound $[^{125}I]$-RTI-55 (Gu, H. et al. J Biol Chem 1994, 269(10): 7124-30 and Giros, B. and Caron, M. G. Trends Pharmacol Sci 1993, 14(2): 43-9). Nomifensine and reserpine were used as reference compounds, giving IC$_{50}$ values of 65 nM and 1.3 µM, respectively. Incubation of Example 2 at 10 µM demonstrated an inhibitory effect of 88% of [$^{125}$I]-RTI-55 binding.

In Vitro MTT Toxicity Screen

The toxicity of the compounds of the present invention at a concentration of 10 µM has been explored using the tetrazolium salt (MTT) method in CHO cells. The MTT method involving conversion of MTT to colored formazan by cells serves as an indirect measurement of cell growth/cell kill, as reported by several groups (Paimela, T. et al. Mol Vis 2012; 18: 1189-96; Hansen, M. B. et al. J Immunol Methods 1989, 119(2): 203-10).

In the MTT assay, cytotoxicity is correlated with the color of MTT and is measured with a spectrophotometer at the wavelength of 570 nm. Briefly, fresh MTT solution (10 mg/mL in 1×PBS) was added (1:20 volume of medium) and the cells were incubated for 1.5 hours. The cells were lysed and purple formazan was dissolved into the solution by overnight incubation with MTT lysis buffer (20% SDS, 50% N,N-dimethylformamide, 2% acetic acid, 25 mM HCl; the volume of medium+volume of MTT salt solution).

The compounds of Examples 2, 3, 4 and 18 showed 100% cell viability compared to the positive control group (10% DMSO), suggesting that these compounds are non-toxic at the concentration studied.

Maximum Tolerated Doses Evaluated in C57BL6 Mice

An alternative evaluation of the toxicity of the compounds of the present invention may be conducted using the method described in Branch, D. R. Exp Toxicol Pathol 2009, 61(2): 133-6 and Emmenegger, U. et al. Neoplasia 2011, 13(1): 40-8. The objective of the assay was to determine the non-toxic dose after 5 days oral administration by evaluating the toxicity of the compounds of the invention at escalating doses starting from 1 g/kg.

The compound of Example 2 was evaluated for oral toxicity in the mouse after oral administration for 5 days and did not show any toxic effect when administered at doses up to 100 mg/kg/day during 5 days.

Passive Avoidance Test

The passive avoidance task is a fear-aggravated test used to evaluate learning and memory in rodent models of CNS disorders. In this test, subjects learn to avoid an environment in which an aversive stimulus (such as a footshock) was previously delivered.

The animals can freely explore the light and dark compartments of the chamber and a mild footshock is delivered in one side of the compartment. Animals eventually learn to associate certain properties of the chamber with the footshock. The latency to pass the gate in order to avoid the stimulus is used as an indicator of learning and memory. The passive avoidance task is useful for evaluating the effect of novel chemical entities on learning and memory, as well as studying the mechanisms involved in cognition (Cappon, G. D. Eur J Pharmacol. 2008 579(1-3): 225-8).

A passive avoidance test with Example 2 administered i.p. at 30 mg/kg was conducted to assess the formation of recent and long-term memory (consolidation) using a negative reinforcement (0.6 mA footshock; 2 s). In the test phase 24 hours later, mice treated with Example 2 remained a significantly longer time on the platform than the saline-treated group (one way ANOVA F=8.7231; P=0.006), indicating a significant enhancement of recent memory formation.

Novel Object Recognition Test

The novel object recognition task is used to evaluate cognition, particularly memory recognition, in rodent models of CNS disorders. This test is based on the spontaneous tendency of rodents to spend more time exploring a novel object than a familiar one. The choice to explore the novel object reflects the use of learning and memory recognition.

The novel object recognition test provides a measure of activity in a novel environment allowing tests for emotional reactivity and also for novel object recognition, a cognitive domain that depends on hippocampal functional integrity. Animals were habituated to the presence of two identical objects (LEGO® pieces) during a single session of 5 minutes (training) and sniffing (exploration of an object was defined as pointing the nose to the object at a distance of <1 cm and/or touching it with the nose). Mice were injected with saline or with the compound to be tested and returned to their home cages. At 24 hours the animals were introduced in the same open field again with the same two items (familiarization), and again exploration in each of them for 5 minutes was registered. One hour later, the mice were retested in the open field for 3 minutes, but this time with one of the "familiar" objects replaced by a new one (test). To analyze cognitive performance, a discrimination index was calculated as the difference in time exploring the novel and familiar object, expressed as the ratio of the total time spent exploring both objects, which made it possible to adjust for any differences in total exploration time. This test is useful for assessing impaired cognitive ability in transgenic strains of mice and evaluating novel chemical entities for their effect on cognition (Zhang, R. J Alzheimers Dis 2012, 31(4): 801-12). Drugs such as fluoxetine, a reference agent among the selective serotonin inhibitors, have been described as cognitive enhancers in this animal model after chronic but not acute administration (Alme, M. et al. Neuroplasticity 2007, 26496).

Mice treated with Example 2 also increased their interest in the new object, but they were significantly more competent as compared to the saline group (Example 2: time familiar object=24.4%; time new object=75.5%), suggesting that the administration of the compound enhances memory recognition. Mice treated with example 2 discriminated the two objects better (one-way ANOVA F=5.433; P=0.03), suggesting a clear improvement in cognitive ability in treated mice under acute conditions. Fluoxetine (30 mg/kg i.p.), the monoamine oxidase inhibitor rasagiline (3 mg/kg i.p.) and the norepinephrine and serotonin reuptake inhibitor milnacipran (30 mg/kg i.p.) were also assessed and showed an absence of cognitive improvement in the same experimental conditions.

Morris Water Maze Test

Familial Alzheimer's disease (AD) is associated with mutations that lead to the production of the β-amyloid 42 (Aβ42) peptide, a constituent of the characteristic amyloid plaques diagnostic of AD. These mutations occur at the proteolytic cleavage sites in the gene encoding the amyloid precursor protein (APP), and in the genes for presenilins 1 and 2 (PSEN1 and PSEN2), enzymes involved in APP cleavage. The APP-mutant mouse strain J20 (B6.Cg-Tg (PDGFB-APPSwind)20 Lms/2J) develops amyloid peptide deposits by 5 to 7 months of age, with higher deposition in the dentate gyrus of the hippocampus and neocortex, and shows an abnormal, hippocampal functionally-dependent cognitive profile. The J20 mouse model is a suitable experimental animal model for testing the activity of drugs on cognitive performance because these mice show robust impairment in spatial learning and spatial reference memory (Karl, T. et al. Behav Brain Res 2012, 228(2): 392-97; Garcia-Barroso, C. et al. Neuropharmacology 2013, 64: 114-23). The effects of Example 2 on spatial memory and learning in the J20 mouse model using the Morris water maze test (Vorhees, Ch. V. and Williams, M. T. Nat Protoc 2006, 1(2): 848-58) were investigated in our laboratory.

The Morris water maze test was applied to 45 old male mice. Twenty wild-type and 25 J20 mice (n=10-11 for each group of treatment/genotype; 10-14 months of age) were treated with vehicle or Example 2 at 30 mg/kg i.p. Percent times in quadrants, escape latencies, distance to goal and other parameters were recorded and compared between groups to assess the compound's activity. Example 2 showed an increase in visuospatial memory and learning in old wild type mice, and a positive effect in some sessions in J20.

Biochemical Survey on Neurotrophin Plasticity Signaling in Mice

Acute biochemical neuronal changes in neurotrophin and synaptic plasticity signaling after the administration of the compounds to be tested may be studied by Western blot assessment of ERK, Akt, phospholipase C (PLC), Trk-B, glucagon receptor and CAMK II phosphorylation assays in the hippocampus, striatum and cortex at 1 hour post-administration.

Two groups of animals were used: C57BL control mice and mice treated by i.p. administration of a dose of 30 mg/kg of the compound to be tested diluted in saline solution or control saline (n=6 per group).

Animals were sacrificed by cervical dislocation at the corresponding time and different brain regions were dissected (frontal cortex, striatum, hippocampus, cerebellum) after 3.5-4 hours of having administered the compounds. Samples were retrieved and immediately frozen at −80° C., tissue was homogenized in lysis buffer (50 mM Tris-HCl [pH 7.5], 150 mM NaCl, 10% glycerol, 1% Triton X-100, 100 mM NaF, 5 µm $ZnCl_2$ and 10 mM EGTA) plus protease inhibitors (phenylmethylsulfonyl fluoride [2 mm], aprotinin [1 µg/mL], leupeptin [1 µg/mL] and sodium orthovanadate [1 mm]) and centrifuged at 13,200 g for 15 minutes. The supernatants were collected and the protein concentration was measured using the Dc protein assay kit (Bio-Rad, Hercules, Calif., USA) read in a 96-well plate.

Proteins were denatured in 62.5 mM Tris-HCl (pH 6.8), 2% (w/v) SDS, 10% glycerol, 140 mM R-mercaptoethanol and 0.1% (w/v) bromophenol blue, heated at 100° C. for 5 minutes (except for vesicular glutamate transporter 1 [VGLUT1] blotting: 10 minutes 60° C.) and resolved in denaturing polyacrylamide gels (8% acrylamide); proteins were transferred to a nitrocellulose membrane and washed twice in Tris-buffered saline containing 0.1% Tween-20 (TBS-T). After blocking (TBS-T solution plus 5% bovine serum albumin and 5% skimmed milk) at room temperature for 1 hour, membranes were blotted overnight at 4° C. with the following primary antibodies: anti-Trk-B (1:1000), anti-phospho-Trk-B (Y515 1:1000), anti-ERK (1:1000), anti-Akt (1:1000), anti-phospho-ERK (1:1000), anti-phospho-Akt (1:1000), anti-PLCγ1 (1:1000) and anti-phospho-PLCγ1 (1:1000).

After primary antibody incubation, membranes were washed with TBS-T and incubated for 1 hour at room temperature with the appropriate horseradish peroxidase-conjugated secondary antibody (1:2000; Promega, Madison, Wis., USA), and the reaction was finally visualized with the Western Blotting Luminol Reagent (Santa Cruz Biotechnology, Santa Cruz, Calif., USA). Western blot replicates were scanned and quantified using a computer-assisted densitometric analysis.

Figure 2:
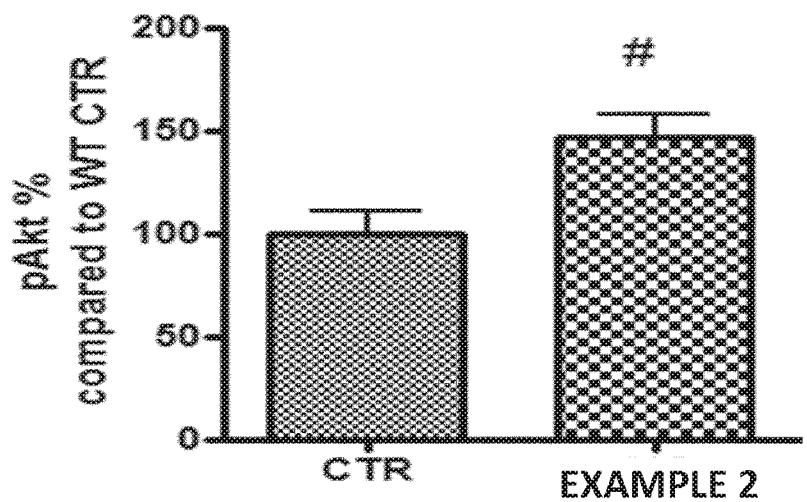
FIG. 2 shows the levels of p-Akt at the hippocampus of mice after intraperitoneal administration of the compound of Example 2 at a dose of 30 mg/kg compared to a control wherein the level of the control mice have been taken as reference value (100% p-Akt phosphorylation).

In the case of the compound of Example 2 administered intraperitoneally at a dose of 30 mg/kg, a positive significant increase in p-ERK and p-Akt levels specific for hippocampus at 1 hour after administration was seen, as shown in FIG. 1 (p-ERK) and FIG. 2 (p-Akt). No significant change was observed on p-PLCγ1; this suggests a possible activation of plasticity pathways, most likely not specific for Trk-B activation, since the three major pathways downstream of Trk-B are the aforementioned ERK, Akt and PLCγ1.

Thus, after treatment with the compound of Example 2, an increase in Akt phosphorylation in the hippocampus and a trend for an increase in ERK1/2 phosphorylation were observed. Although the results did not identify the compound of Example 2 as a Trk-B agonist, Akt signaling changes and the p-ERK trend 1 hour after administration support the cognitive-enhancing effect of compound of Example 2 observed in vivo.

In Vitro Study on Neurotrophin Plasticity Signaling in SN56 and T48 Cell Lines

The purpose of the study was to assess the acute biochemical neuronal changes in neurotrophin and synaptic plasticity signaling in vitro after the incubation in SN56 (fusion of mouse septal area cells and neuroblastoma cells with no TRKB expression) and T48 (SN56 stable transfected to express TrkB) cell lines the Examples 3 and 4. These changes were studied with a western blot assessment of Erk, Akt, PLC, Trkb, BDNF and CREB (cAMP response element-binding protein) phosphorilation assays.

Proteins were denatured in 62.5 mM Tris-HCl (pH 6.8), 2% (w/v) SDS, 10% glycerol, 140 mM β-mercaptoethanol and 0.1% (w/v) bromophenol blue, heated at 100° C. for 5 min (except for VGLUT1 blotting: 10 minutes 60° C.) and resolved in denaturing polyacrylamide gels (8% acrylamide); proteins were transferred to a nitrocellulose membrane), and washed twice in Tris-buffered saline containing 0.1% Tween-20 (TBS-T). After blocking (TBS-T solution plus 5% bovine serum albumin and 5% skimmed milk) at room temperature for 1 h, membranes were blotted overnight at 4° C. with the following primary antibodies: anti-TrkB, anti-phosphotrkB, anti-Erk, anti-Akt, anti-phosphoErk, anti-phosphoAkt, antiPLCγ1, anti-phosphoPLCγ1, anti-BDNF, anti-CREB and anti-phosphoCREB.

After primary antibody incubation, membranes were washed with TBS-T and incubated for 1 h at room temperature with the appropriated horseradish peroxidase-conjugated secondary antibody (Promega, Madison, Wis., USA), and the reaction was finally visualized with the Western Blotting Luminol Reagent (Santa Cruz Biotechnology, Santa Cruz, Calif., USA). Western blot replicates were scanned and quantified using a computer-assisted densitometric analysis.

Statistical analysis was performed using the one-way analysis of variance (ANOVA) followed by Tuker's multiple comparison post hoc test.

Figure 3:
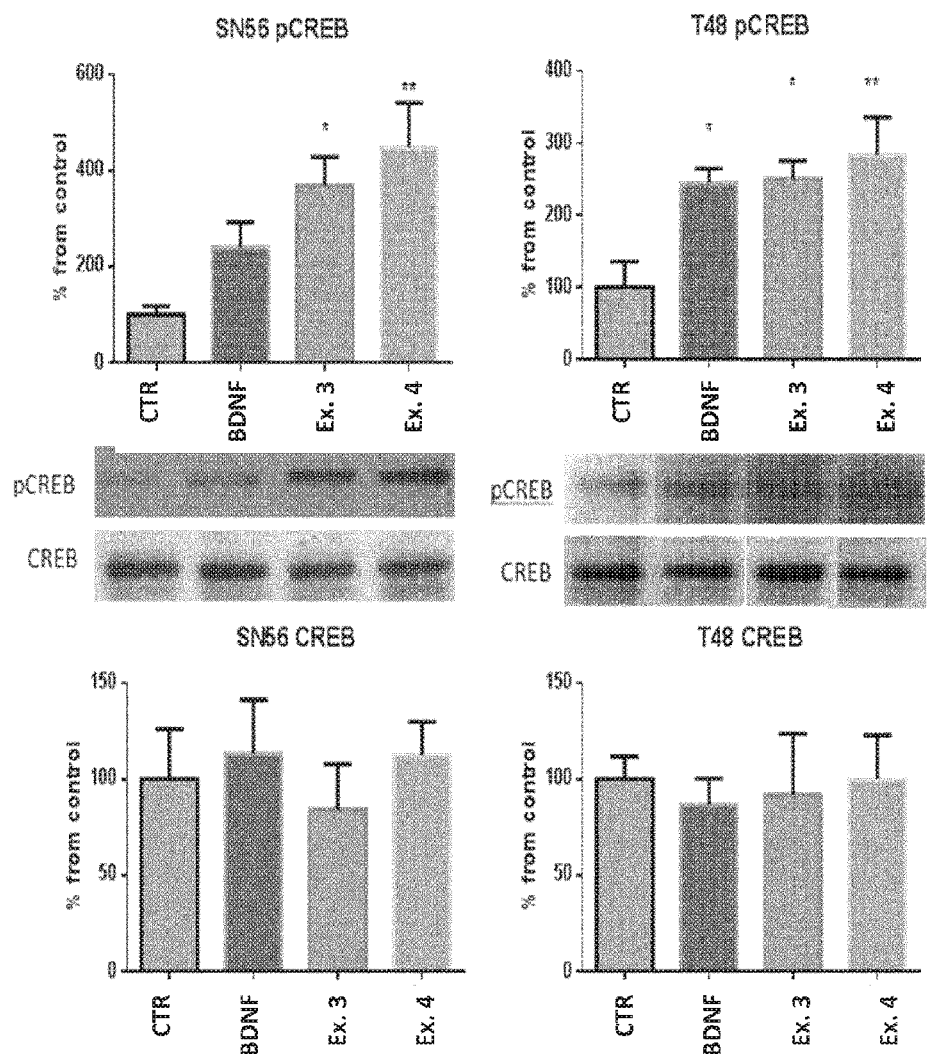
FIG. 3 shows the expression levels of CREB and phosphorylated CREB (pCREB) in SN56 and T48 cell lines after incubation with BDNF (Brain derived neurotrophic factor) and the compounds of examples 3 and 4 compared to a control (CTR) wherein the level of expression of the control mice has been taken as reference value (100%).

After additional screening on the membranes by staining against pCREB and CREB, Example 3 and example 4 increase significantly the phosphorylation of CREB in both cell lines (see FIG. 3), which strongly suggest that it is not in a BDNF-dependent mechanism.

Taking into account the previous In vivo cognitive results and the delayed Erk and Akt activation in the acute assay, we cannot discard other main pathways that might be reflected by neuronal plasticity improvements (for example, via other trophic factors, neurotransmitter receptors or biochemical subcellular pathways activation), it is notable that CREB phosphorylation might play an important role on the described In Vivo effects but it is a main target of multiple important pathways which can be regulated in many ways.

Chronic Effects of the Compound of Example 2 (3 Month Treatment) for Defects of Cognition in Wild Type Old Mice The effects of chronic administration of the compound of Example 2 administered by oral intake (10 mg/kg/day during 3 months through access to inverted graduated 25 mL filled with tap water) on cognition in wild type old mice were studied.

To examine the effect of chronic treatment for 3 months with the compound of Example 2, the novel objet recognition and the Y maze tests were used.

The treatment with the compound of Example 2 for 3 months was able to restore the discrimination index in control mice (Bonferroni post hoc comparisons Wild Type control vs. Wild Type Example 2 p=0.055). Importantly, the compound of Example 2 had a positive effect on recognition memory in old WT mice which showed poor discriminative abilities. These results suggest that the compound of Example 2 has potential cognitive-enhancing properties in old mice and this may be extraordinary relevant to target cognitive dysfunction associated to ageing.

Acute Effects of the Compound of Example 2 in Fragile X Mouse Model Defects of Cognition.

Fragile X syndrome (FXS) is a common inherited cause of human mental retardation. Behavioral features of the disorder include cognitive impairment, hyperactivity, attention deficits, sensory hypersensitivity, social isolation and anxiety behavior. FXS results from expansion of a CGG repeat region of the fragile X mental retardation (FMR1) gene located on the X chromosome. As consequence, the gene is hypermethylated and its transcription into mRNA inactivated. In brain, the protein product of FMR1 gene (FMRP) has important role in synaptic function and synaptic plasticity (Brown, Jin et al. 2001 Cell 107(4): 477-487.), and the loss of the protein may explain the behavioral and physical abnormalities in FXS patients.

Mouse models for the disease have been generated by deleting the FMR1 gene (knockout, KO mice) (Bakker C E 1994 Cell 78(1): 23-33). Fmr1 KO mice are able to recapitulate some of the physical and behavioral characteristics of the human syndrome. These mice show hyperactivity and have spatial learning impairment in the Morris water maze, altered anxiety-like responses, and abnormal social behavior.

Example 2 effects on social disability in a model of Fmr1 KO was performed. Social behavior was examined on an open-field that consisted of an arena (70 cm long×70 cm wide×30 cm high) made of Plexiglas. An overhead camera connected to the video-tracking software SMART (Panlab, Spain) was used to monitor the animal's behavior. The experimental design included three sessions:

1) Habituation session Animals were habituated for 10 min to an arena containing two empty transparent cylinders (30 cm diameter×40 cm high) made of Plexiglas. The cylinders were perforated to have interaction points and were located on two corners of the open field. Time exploring the cylinders was registered along the 10 min duration. After the habituation session mice received an acute injection of either saline or Example 2 (30 mg/kg i.p.) and replaced on their cages.

2) Social interaction 24 h later, animals were replaced to the arena containing the two cylinders, one cylinder was empty and the other one contained a stranger individual (stimulus). The time exploring the two cylinders was registered for 10 minutes. The stimulus individual was always a juvenile mouse (less than two months of age), to avoid the group hierarchy and aggressiveness towards non familiar individuals that show adult male mice. In addition, the stimulus individual was genotype matched with the testing mouse. The position of the stimulus individual was counterbalanced between animals. After the sociability session mice received an acute injection of either saline or Example 2 (30 mg/kg i.p.).

3) Social recognition 24 h later, animals were replaced to the arena containing the two cylinders, one cylinder contained the same stimulus individual presented during the social interaction session (familiar) and the other contained a novel stimulus individual. Both stimuli were juvenile animals and genotype matched. The position of the familiar stimulus remained the same as it was in the social interaction session, and counterbalanced between animals. Once the subject mice finished the test they remained individually housed in a separate cage until the other cage partner finalized the test, to avoid exposition to olfactory cues from stimuli mice. In all cases, those mice from the same cage were never exposed to the same stimuli, either familiar or novel. The time exploring the two cylinders was registered for 10 minutes. The discrimination index was calculated as time exploring the novel stimulus mouse–time exploring the familiar stimulus mouse/total time of exploration×100. The arena and cylinders were deeply cleaned between animals to avoid olfactory cues. All measures of exploration were manually registered by the experimenter blind to genotype and treatment. Exploratory behavior was defined as the animal directing its nose towards the cylinder at a distance of <2 cm. A proximal zone of 14 cm from the cylinders was defined as interaction zone and the time spent in these zones was registered as index of exploratory behavior.

Figure 4A:
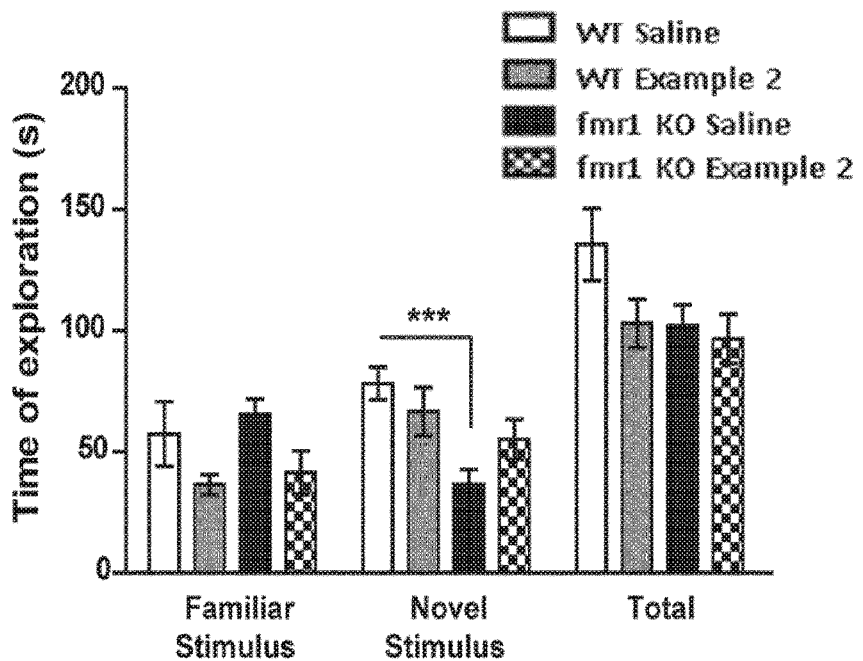
FIG. 4A plots the time (s) that the test mouse devotes to exploring two cylinders: a first cylinder containing a familiar genotype-matched juvenile stimulus mouse and a second cylinder containing a novel stimulus mouse and the total time of exploration (both cylinders) during a 10 min session.
Figure 4B:
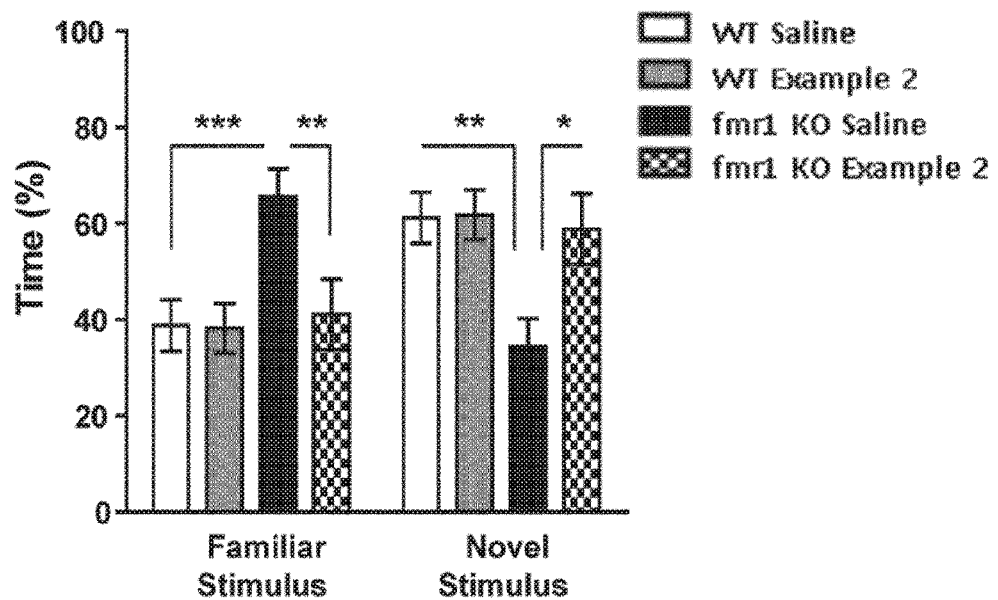
FIG. 4B Plots the percentage of time spent near the two cylinders during the 10 min session.

Acute Example 2 administration significantly reduced the time that WT and fmr1 KO mice spent exploring the familiar stimulus (FIG. 4A, Two way ANOVA, Treatment effect F 1.47=6.478, p=0.015). Interestingly, Example 2 completely restored the social behavior alteration detected in fmr1 KO mice. Acute Example 2 exposition significantly increased the time fmr1 KO mice spent near the novel stimulus (FIG. 4B, Bonferroni as post hoc KO saline vs. KO Example 2 p=0.003) while reducing the time spent near the familiar individual (FIG. 4B, Bonferroni as post hoc KO saline vs. KO Example 2 p=0.038). Additionally, administration of example totally compensated the deficit in social recognition detected in fmr1 KO mice (FIG. 4C, Bonferroni as post hoc KO saline vs. KO Example 2 p=0.006).

Acute administration of Example 2 completely restored the social abnormalities of fmr1 KO mice. After treatment with example 2, the reduced time fmr1 KO mice spent exploring the novel stimulus mouse rose at levels comparable to those detected in wild type animals. In contrast, example 2 did not modify the social recognition in wild type mice.

Neuroplasticity and Precognitive Activity Relationship

Neuroplasticity is the capacity of the nervous system to respond to noxious stimuli by reorganizing its structure and function. It plays a crucial role in physiological and pathological conditions, as cerebral injury and stroke, mental and addictive disorders, pediatric developmental disorders, neurodegeneration and aging. Neural plasticity must be viewed as a gain in function, or with negative consequences such as loss of function or increased injury. Thus, in this context, the molecular mechanisms that support neural plasticity also have pharmacological vulnerabilities. For example, plasticity-promoting pharmacological interventions can be lost with NMDA blockade (dextromethorphan) or increased GABAergic tone (lorazepam).

On the contrary, some authors have suggested that cognitive therapy and antidepressant medication probably engage similar neural mechanisms promoting neural plasticity. The inhibition of cerebral neurotransmitters such as serotonin and norepinephrine after chronic administration could promote neural plasticity via the increase in brain-derived neurotrophic factor (BDNF) and the activation of the Trk-B receptors in the amygdala and hippocampal cells. Other neuropharmacological interventions have been proposed to increase neuroplasticity, such as histone deacetylase (HDAC) inhibitors or mTOR inhibitors.

The compounds of the invention are designed for the treatment of substantia nigra part compacta (SNC) disorders with cognitive impairment. In vitro studies with some of these compounds show a balanced reuptake inhibition of norepinephrine and serotonin. In addition, in vivo studies in behavioral rodent models show that the administration of the compounds of the invention does not affect exploration (activity cages and habituation-deshabituation tests) and increase short- and long-term memory (passive avoidance and object recognition tests). The psychoactive effect determined in the previous hippocampal and cortico-hippocampal tests with the compounds of the invention indicates a procognitive action. Ex vivo studies assessing Akt and ERK pathways after administration of the compounds of the invention (increase of p-Akt and p-ERK) and the in vitro increase of CREB phosphorilation (cMAP Responsive Element Binding protein), a transcription factor involved in learning, cognition and neurite outgrowth suggest that the molecular mechanisms involved in the precognitive effects observed in vivo are related to an increase in neuroplasticity.

The in vitro and in vivo results taken together suggest a neuroplasticity-mediated cognitive increase and make the compounds of the invention potentially useful precognitive drugs for the treatment not only of neurodegenerative diseases such as Alzheimer's disease, Parkinson's disease or Huntington's disease, but also for those diseases with impairment of learning and memory (autistic disorders, fragile X syndrome, Down syndrome, Rett syndrome, etc.).

Pharmaceutical Compositions

The present invention also includes pharmaceutically active compositions comprising compounds of formula (I) and a physiological carrier. The active compositions can be administered either orally, subcutaneously, parenterally, locally (ointments, creams, powders), as drops or as a nasal or buccal.

The following examples of pharmaceutical compositions are offered with the understanding that they are in no way limiting of the invention.

Formulation Example 1: Compositions for Parenteral Administration

These compositions may comprise physiologically acceptable sterile aqueous or non-aqueous solutions, emulsions, suspensions and powders for reconstitution as injectable solutions.

The compounds of the invention in powder form may be diluted in phosphate buffered saline consisting of polysorbate 80, potassium chloride, monobasic phosphate, sodium chloride, dibasic sodium phosphate and water for injection prepared to the desired volume.

Liposome injections for intrathecal use may be prepared in a sterile, injectable suspension of compounds of formula (I), encapsulated in multi-vesicular lipid-based particles.

Formulation Example 2: Tablets and Capsules for Oral Administration

Tablets may be prepared containing as inactive ingredients lactose, magnesium stearate, hydroxypropylmethylcellulose, polyethylene glycol, povidone, sodium starch glycolate and titanium dioxide.

Capsules may be prepared containing as inactive ingredients talcum, sodium lauryl sulfate, celluloid silicon dioxide, magnesium stearate, titanium dioxide (E171), hard gelatin capsule, black ink, propyleneglycol and shellac.

The invention claimed is:

1. A method of increasing neuroplasticity in a subject in need thereof, said subject being affected by at least one disorder selected from the group consisting of depression and fragile X syndrome, said method comprising administering to said subject a compound having formula (I)

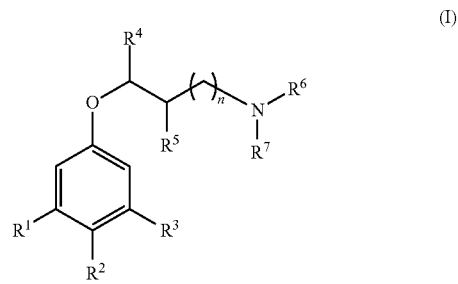

(I)

wherein, $R^1$ and $R^3$ represent hydrogen atoms;

$R^2$ is a group $A\text{-}OR^8$, wherein $R^8$ is selected from the group consisting of H; glycosyl; acetyl; valproyl and lipoyl;

A is a biradical selected from the group consisting of $C_1\text{-}C_6$ alkylene and $C_2\text{-}C_6$ alkenylene $R^4$ is selected from the group consisting of:
H;
a $C_5\text{-}C_7$ cycloalkyl, optionally substituted by at least one group selected from the group consisting of halogen, —OH, $C_1\text{-}C_8$ alkyl, $C_1\text{-}C_8$ alkoxy, —CN, —$NO_2$, —COOH, and —$NH_2$;
a $C_6\text{-}C_{10}$ aryl, optionally substituted by at least one group selected from the group consisting of halogen, —OH, $C_1\text{-}C_8$ alkyl, $C_1\text{-}C_8$ alkoxy, —CN, —$NO_2$, —COOH, and —$NH_2$; and
a 5- or 6-membered monocyclic heteroaryl containing 1 or 2 heteroatoms, said heteroatoms being independently selected from the group consisting of N, O and S; said heteroaryl being optionally substituted by at least one group selected from the group consisting of halogen, —OH, $C_1\text{-}C_8$ alkyl, $C_1\text{-}C_8$ alkoxy, —CN, —$NO_2$, —COOH, and —$NH_2$;

wherein:

a) $R^5$ is selected from the group consisting of H and an 8-, 9- or 10-membered bicyclic heteroaryl containing 1 or 2 heteroatoms, said heteroatoms being independently selected from the group consisting of N, O and S; said heteroaryl being optionally substituted by at least one group selected from the group consisting of halogen, —OH, $C_1\text{-}C_8$ alkyl, $C_1\text{-}C_8$ alkoxy, —CN, —$NO_2$, —COOH, and —$NH_2$;

$R^6$ is selected from the group consisting of H; $C_1\text{-}C_3$ alkyl and $C_1\text{-}C_8$ acyl; and $R^7$ is selected from the group consisting of H and $C_1\text{-}C_3$ alkyl; or b) $R^5$ and $R^6$ taken together form a group selected from the group consisting of —O—$CH_2$—$CH_2$— and —$CH(R^{11})$—$CH_2$—$CH_2$—, wherein $R^{11}$ is a phenyl group optionally substituted by at least one substituent selected from the group consisting of halogen; —OH and —NH$_2$; and
  $R^7$ is H; or
c) $R^5$ is H; and
  $R^6$ and $R^7$ taken together form a group —(CH$_2$)$_m$—CO—;
n is an integer selected from 0, 1 and 2;
m is an integer selected from 2, 3 and 4;
with the proviso that when $R^4$ and $R^5$ are both H, then $R^6$ and $R^7$ taken together form a group —(CH$_2$)$_m$—CO—; or
a pharmaceutically acceptable salt or stereoisomer thereof.

2. The method of claim 1, wherein the subject in need thereof is affected by fragile X syndrome.

3. The method of claim 1, wherein in the compound of formula (I) or the pharmaceutically acceptable salt or stereoisomer thereof,
A is a biradical selected from the group consisting of C$_1$-C$_6$ alkylene; and
a) $R^5$ is selected from the group consisting of H and an 8-, 9- or 10-membered bicyclic heteroaryl containing 1 or 2 heteroatoms, said heteroatoms being independently selected from the group consisting of N, O and S; said heteroaryl being optionally substituted by at least one group selected from the group consisting of halogen, —OH, C$_1$-C$_8$alkyl;
  $R^6$ is selected from the group consisting of H; C$_1$-C$_3$ alkyl and C$_1$-C$_8$acyl; and
  $R^7$ is selected from the group consisting of H and C$_1$-C$_3$ alkyl; or
b) $R^5$ and $R^6$ taken together form a group selected from the group consisting of —O—CH$_2$—CH$_2$— and —CH(R$^{11}$)—CH$_2$—CH$_2$—; and
  $R^7$ is H; or
c) $R^5$ is H; and
  $R^6$ and $R^7$ taken together form a group —(CH$_2$)$_m$—CO—.

4. The method of claim 3, wherein in the compound of formula (I) or the pharmaceutically acceptable salt or stereoisomer thereof,
$R^4$ is selected from the group consisting of:
  H;
  a C$_6$-C$_{10}$ aryl, optionally substituted by at least one group selected from the group consisting of halogen, —OH, and C$_1$-C$_8$alkyl; and
  a 5- or 6-membered monocyclic heteroaryl containing 1 or 2 heteroatoms, said heteroatoms being independently selected from the group consisting of N, O and S; said heteroaryl being optionally substituted by at least one group selected from the group consisting of halogen, —OH, and C$_1$-C$_8$alkyl;
a) $R^5$ is selected from the group consisting of H and an 8-, 9- or 10-membered bicyclic heteroaryl containing 1 or 2 heteroatoms, said heteroatoms being independently selected from the group consisting of N, O and S; said heteroaryl being optionally substituted by at least one group selected from the group consisting of halogen, —OH, C$_1$-C$_8$alkyl;
  $R^6$ is selected from the group consisting of H and C$_1$-C$_3$ alkyl; and
  $R^7$ is selected from the group consisting of H and C$_1$-C$_3$ alkyl; or b) $R^5$ and $R^6$ taken together form a group selected from the group consisting of —O—CH$_2$—CH$_2$— and —CH(R$^{11}$)—CH$_2$—CH$_2$—; and
  $R^7$ is H; or
c) $R^5$ is H; and
  $R^6$ and $R^7$ taken together form a group —(CH$_2$)$_m$—CO—;
$R^8$ is selected from the group consisting of H; acetyl; valproyl and lipoyl;
$R^{11}$ is a phenyl group, optionally substituted by at least one substituent selected from the group consisting of halogen and —OH; and
m is an integer selected from the group consisting of 3 and 4.

5. The method of claim 4, wherein in the compound of formula (I) or the pharmaceutically acceptable salt or stereoisomer thereof,
$R^1$ and $R^3$ represent hydrogen atoms;
$R^2$ is a group A-OR$^8$, wherein A represents a C$_1$-C$_6$ alkylene biradical;
$R^4$ is selected from the group consisting of H; a C$_6$-C$_{10}$ aryl; and a 5- or 6-membered monocyclic heteroaryl containing 1 or 2 heteroatoms, said heteroatoms being independently selected from the group consisting of N, O and S; and:
a) $R^5$ is H; $R^6$ is selected from the group consisting of H and C$_1$-C$_3$ alkyl; and $R^7$ is selected from the group consisting of H and methyl; or
b) $R^5$ and $R^6$ taken together form a group selected from the group consisting of —O—CH$_2$—CH$_2$— and —CH(R$^{11}$)—CH$_2$—CH$_2$—; and $R^7$ is H; or
c) $R^5$ is H; and $R^6$ and $R^7$ taken together form a group —(CH$_2$)$_m$—CO—;
$R^8$ is H; and
$R^{11}$ is a phenyl group optionally substituted by at least one halogen atom.

6. The method of claim 5, wherein in the compound of formula (I) or the pharmaceutically acceptable salt or stereoisomer thereof,
$R^2$ is a group A-OR$^8$; wherein A represents an ethylene biradical and $R^8$ represents a hydrogen atom;
$R^4$ represents a phenyl group;
$R^5$ and $R^6$ represent hydrogen atoms;
$R^7$ represents a methyl group; and
n has a value of 1.

7. The method of claim 1, wherein the compound of formula (I) is selected from the group consisting of:
a) 1-[2-[4-(2-Hydroxyethyl)phenoxy]ethyl]pyrrolidin-2-one;
b) 2-[4-[3-(Methylamino)-1-phenylpropoxy]phenyl]ethanol hydrochloride;
c) (R)-2-[4-[3-(Methylamino)-1-phenylpropoxy]phenyl]ethanol hydrochloride;
d) (S)-2-[4-[3-(Methylamino)-1-phenylpropoxy]phenyl]ethanol hydrochloride;
e) 2-[4-[3-(Methylamino)-1-phenylpropoxy]phenyl]ethanol L-ascorbic acid salt;
f) 2-[4-[3-(Methylamino)-1-phenylpropoxy]phenyl]ethanol ferulic acid salt;
g) 2-[4-[3-(Methylamino)-1-phenylpropoxy]phenyl]ethanol caffeic acid salt;
h) 2-[4-[3-(Methylamino)-1-phenylpropoxy]phenyl]ethanol valproic acid salt;
i) 2-[4-[3-(Methylamino)-1-phenylpropoxy]phenyl]ethanol (R)-lipoic acid salt;
j) 4-[3-(Methylamino)-1-phenylpropoxy]phenethyl acetate hydrochloride;

k) N-[3-[4-(2-Hydroxyethyl)phenoxy]-3-phenylpropyl]-N-methyl-2-propylpentanamide;
l) 2-[4-(3-Amino-1-phenylpropoxy)phenyl]ethanol hydrochloride;
m) (R)-2-[4-[3-(Methylamino)-1-(thiophen-2-yl)propoxy]phenyl]ethanol;
n) 4-[4-[3-(Methylamino)-1-phenylpropoxy]phenyl]butan-1-ol hydrochloride;
o) (E)-tert-Butyl [3-[4-(3-hydroxyprop-1-enyl)phenoxy]-3-phenylpropyl](methyl) carbamate;
p) 3-[4-[3-(Methylamino)-1-phenylpropoxy]phenyl]propan-1-ol hydrochloride;
q) [4-[3-(Methylamino)-1-phenylpropoxy]phenyl]methanol hydrochloride;
r) 2-[4-(Morpholin-2-ylmethoxy)phenyl]ethanol hydrochloride;
s) [5-[3-(Methylamino)-1-phenylpropoxy]-1,3-phenylene]dimethanol hydrochloride;
t) 2,2'-[5-[3-(Methylamino)-1-phenylpropoxy]-1,3-phenylene]diethanol;
u) 3,3'-[5-[3-(Methylamino)-1-phenylpropoxy]-1,3-phenylene]dipropan-1-ol;
v) 4,4'-[5-[3-(Methylamino)-1-phenylpropoxy]-1,3-phenylene]dibutan-1-ol;
w) (2R,3S,4S,5R,6R)-2-(Hydroxymethyl)-6-[4-[3-(methylamino)-1-phenylpropoxy]phenethoxy]tetrahydro-2H-pyran-3,4,5-triol;
x) 2-[4-(3-Dimethylamino-1-phenylpropoxy)phenyl]ethanol;
y) 4-[4-(3-Methylamino-1-phenylpropoxy)phenyl]but-2-en-1-ol;
z) 6-[4-(3-Methylamino-1-phenylpropoxy)phenyl]hexan-1-ol;
aa) 6-[4-(3-Methylamino-1-phenylpropoxy) phenyl]hex-5-en-1-ol;
bb) (S)-2-[4-(3-Methylamino-1-thiophen-2-ylpropoxy)phenyl]ethanol;
cc) 2-[4-(Morpholin-2-yl(phenyl)methoxy)phenyl]ethanol;
dd) 2-[4-[[(3S,4R)-4-(4-Fluorophenyl)piperidin-3-yl]methoxy]phenyl]ethanol;
ee) 2-[2-Dimethylamino-1-[4-(2-hydroxyethyl)phenoxy]ethyl]cyclohexanol;
ff) 1-[2-Dimethylamino-1-[4-(2-hydroxyethyl)phenoxy]ethyl]cyclohexanol;
gg) 2-[4-[2-(4-Fluoroindol-1-yl)-4-methylaminobutoxy]phenyl]ethanol;
hh) 2-Propylpentanoic acid 2-[4-(3-methylamino-1-phenylpropoxy) phenyl] ethyl ester;
ii) 5(R)-[1,2]Dithiolan-3-ylpentanoic acid 2-[4-(3-methylamino-1-phenylpropoxy)phenyl]ethyl ester;
salts thereof; and
stereoisomers thereof.

8. The method of claim 7, wherein the compound of formula (I) is 2-[4-[3-(Methylamino)-1-phenylpropoxy]phenyl]ethanol, a salt thereof, or a stereoisomer thereof.

9. The method of claim 7, wherein the compound of formula (I) is 2-[4-[3-(Methylamino)-1-phenylpropoxy]phenyl]ethanol hydrochloride or a stereoisomer thereof.

10. The method of claim 7, wherein the compound of formula (I) is (R)-2-[4-[3-(Methylamino)-1-phenylpropoxy]phenyl]ethanol hydrochloride.

11. The method of claim 7, wherein the compound of formula (I) is (S)-2-[4-[3-(Methylamino)-1-phenylpropoxy]phenyl]ethanol hydrochloride.

12. A method of treating a subject suffering from a neurological disorder, said method comprising administering to said subject a compound having formula (I)

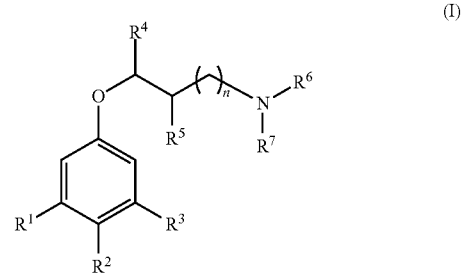

wherein,
$R^1$ and $R^3$ represent hydrogen atoms;
$R^2$ is a group A-$OR^8$, wherein $R^8$ is selected from the group consisting of H; glycosyl; acetyl; valproyl and lipoyl;
A is a biradical selected from the group consisting of $C_1$-$C_6$ alkylene and $C_2$-$C_6$ alkenylene
$R^4$ is selected from the group consisting of:
H;
a $C_5$-$C_7$ cycloalkyl, optionally substituted by at least one group selected from the group consisting of halogen, —OH, $C_1$-$C_8$ alkyl, $C_1$-$C_8$ alkoxy, —CN, —$NO_2$, —COOH, and —$NH_2$;
a $C_6$-$C_{10}$ aryl, optionally substituted by at least one group selected from the group consisting of halogen, —OH, $C_1$-$C_8$alkyl, $C_1$-$C_8$alkoxy, —CN, —$NO_2$, —COOH, and —$NH_2$; and
a 5- or 6-membered monocyclic heteroaryl containing 1 or 2 heteroatoms, said heteroatoms being independently selected from the group consisting of N, O and S; said heteroaryl being optionally substituted by at least one group selected from the group consisting of halogen, —OH, $C_1$-$C_8$ alkyl, $C_1$-$C_8$ alkoxy, —CN, —$NO_2$, —COOH, and —$NH_2$;
wherein:
d) $R^5$ is selected from the group consisting of H and an 8-, 9- or 10-membered bicyclic heteroaryl containing 1 or 2 heteroatoms, said heteroatoms being independently selected from the group consisting of N, O and S; said heteroaryl being optionally substituted by at least one group selected from the group consisting of halogen, —OH, $C_1$-$C_8$ alkyl, $C_1$-$C_8$ alkoxy, —CN, —$NO_2$, —COOH, and —$NH_2$;
$R^6$ is selected from the group consisting of H; $C_1$-$C_3$ alkyl and $C_1$-$C_8$ acyl; and
$R^7$ is selected from the group consisting of H and $C_1$-$C_3$ alkyl; or
e) $R^5$ and $R^6$ taken together form a group selected from the group consisting of —O—$CH_2$—$CH_2$— and —CH($R^{11}$)—$CH_2$—$CH_2$—, wherein $R^{11}$ is a phenyl group optionally substituted by at least one substituent selected from the group consisting of halogen; —OH and —$NH_2$; and
$R^7$ is H; or
f) $R^5$ is H; and
$R^6$ and $R^7$ taken together form a group —$(CH_2)_m$—CO—;
n is an integer selected from 0, 1 and 2;
m is an integer selected from 2, 3 and 4;

with the proviso that when $R^4$ and $R^5$ are both H, then $R^6$ and $R^7$ taken together form a group $-(CH_2)_m-CO-$;
or
a pharmaceutically acceptable salt or stereoisomer thereof
said neurological disorder being at least one condition selected from the group consisting of depression and fragile X syndrome.

13. The method of claim 12, wherein said neurological disorder is depression.

14. The method of claim 12, wherein said neurological disorder is fragile X syndrome.

15. The method of claim 1, wherein the subject in need thereof is affected by depression.

\* \* \* \* \*